United States Patent
Hirai et al.

(10) Patent No.: US 8,021,845 B2
(45) Date of Patent: Sep. 20, 2011

(54) PROBES FOR DETECTING OBESITY GENE

(75) Inventors: Mitsuharu Hirai, Kyoto (JP); Satoshi Majima, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 130 days.

(21) Appl. No.: 12/306,417

(22) PCT Filed: Nov. 30, 2007

(86) PCT No.: PCT/JP2007/073207
§ 371 (c)(1),
(2), (4) Date: Dec. 23, 2008

(87) PCT Pub. No.: WO2008/066164
PCT Pub. Date: Jun. 5, 2008

(65) Prior Publication Data
US 2010/0112559 A1 May 6, 2010

(30) Foreign Application Priority Data

Nov. 30, 2006 (JP) ................................ 2006-322960
Nov. 30, 2006 (JP) ................................ 2006-322961
Sep. 7, 2007 (JP) ................................ 2007-232614

(51) Int. Cl.
*C12Q 1/68* (2006.01)
*C07H 21/04* (2006.01)

(52) U.S. Cl. ...................... 435/6.12; 536/22.1; 536/24.3

(58) Field of Classification Search ............. 435/6, 6.12; 536/22.1, 24.3
See application file for complete search history.

(56) References Cited

U.S. PATENT DOCUMENTS

| | | | |
|---|---|---|---|
| 6,861,217 B1 * | 3/2005 | Liggett | ............... 435/6 |
| 2001/0051712 A1 | 12/2001 | Drysdale et al. | |
| 2002/0137069 A1 * | 9/2002 | Yu et al. | ............... 435/6 |
| 2003/0202937 A1 | 10/2003 | Sabbadini et al. | |
| 2004/0091864 A1 * | 5/2004 | French et al. | ............... 435/6 |
| 2007/0003932 A1 | 1/2007 | Hirai | |

FOREIGN PATENT DOCUMENTS

| | | |
|---|---|---|
| JP | 2005/058107 A | 3/2005 |
| JP | 2005-287447 | 10/2005 |
| WO | 99/37761 | 7/1999 |
| WO | WO 02/24905 A1 | 3/2002 |
| WO | 02/072882 | 9/2002 |
| WO | WO 2004/092385 A1 | 10/2004 |
| WO | 2005/106488 | 11/2005 |
| WO | WO 2006/031181 A1 | 3/2006 |
| WO | WO 2006/075254 A2 | 7/2006 |
| WO | WO 2006/123943 A1 | 11/2006 |

OTHER PUBLICATIONS

Lowe et al. Nucleic Acid Research, 1990, vol. 18(7), p. 1757-1761.*
The nucleic acid sequence search reports for SEQ ID No. 1, 72 and 114.*
European Patent Office, Supplementary Partial European Search Report issued in European Application No. 07832872.1 and mailed Oct. 23, 2009—17 pages.
Database Geneseq [Online], WPI; 2003-900614/82, Retrieved from EBI accession No. GSN: ADG25423, Feb. 2004 XP002549039.
Database EMBL [Online], Retrieved from EBI accession No. EMBL: DD235411, Apr. 2006—XP002549040.
Database EMBL [Online], Retrieved from EBI accession No. EMBL: AX608994, Feb. 2003—XP002549058.
International Search Report of PCT/JP2007/073207, dated Feb. 19, 2008.
Martinez et al. "Association between Genetic Polymorphisms of the $\beta_2$-Adrenoceptor and Response to Albuterol in Children with and without a history of Wheezing." The Journal of Clinical Investigation, vol. 100(12), Dec. 1997, pp. 3184-3188.
Sakane et al. "$\beta_3$-adrenergic-receptor polymorphism: a genetic marker for viceral fat obesity and the insulin resistance syndrome." Diabetologia, vol. 40(2), 1997, pp. 200-204.
Valve et al. "Synergistic effect of polymorphisms in uncoupling protein 1 and $\beta_3$-adrenergic receptor genes on basal metabolis rate in obese Finns." Diabetologia, vol. 41(3), 1998, pp. 357-361.
Large et al. "Human $\beta_2$-Adrenoceptor Gene Polymorphisms Are Highly Frequent in Obesity and Associate with Altered Adipocyte $\beta_2$-Adrenoceptor Function." The Journal of Clinical Investigation, vol. 100(12), Dec. 1997, pp. 3005-3013.
Kirstein et al., "Autonomic Nervous System Pharmacogenomics: A Progress Report," Pharmacological Reviews, vol. 56, No. 1, pp. 31-52, 2004.
Akagi et al., Development of a ligation-based impedimetric DNA sensor for single-nucleotide polymorphism associated with metabolic syndrome, Electrochim. Acta, 51:6367-6372 (2006).

* cited by examiner

*Primary Examiner* — Kenneth R. Horlick
*Assistant Examiner* — Joyce Tung
(74) *Attorney, Agent, or Firm* — Morgan, Lewis & Bockius LLP

(57) ABSTRACT

Primer sets for amplifying target regions containing sites to be detected in the obesity gene (the β2AR gene, the β3AR gene, and the UCP1 gene) by a gene amplification method are provided, wherein the primer sets can amplify the regions specifically. Three pairs of primer sets are used including forward primers composed of the base sequences of SEQ ID NO: 9 or SEQ ID NO: 109, SEQ ID NO: 25, and SEQ ID NO:43 as well as reverse primers composed of the base sequences of SEQ ID NO: 18, SEQ ID NO: 30, and SEQ ID NO: 63, respectively. The use of these primer sets makes it possible to specifically amplify a target region including a site where a polymorphism to be detected is generated in the β2AR gene, the β3AR gene, and the UCP1 gene, in the same reaction solution at the same time.

21 Claims, 5 Drawing Sheets

SEQUENCE LISTING

```
<160> NUMBER OF SEQ ID NOS: 166

<210> SEQ ID NO 1
<211> LENGTH: 9968
<212> TYPE: DNA
<213> ORGANISM: Homo sapiens

<400> SEQUENCE: 1
tgcaaaagac atgaagtcat cctttttat ggctgcacag tattccatgg tgtatatgtg      60
ccacattttc tttatcaagt ctattcttga tgggcatttg ggttggttcc aagtctttgc     120
tattgtgaac agtgctgcaa taaacataca tgtccatgtg tcttatagt agaatgattt     180
```

```
ataatcctta gggtatatac caggtaatgg gattgctggg tcaaatggta tttcttgttc      240
tagatccttg agggattgcc acactgtctt ccacaatgtt tgaactaatt tacattccta      300
ccaacagtgt aaaagtgttc ctatttctcc acatcctttc cagcatctgt tgtttcctga      360
cttcctgttt ttttttttgag acggagtctc actgtgtcac cccggatgga gtgcagtggc     420
acaatctcgg ctcactgcaa cctccacctc ccaggttcaa gcgattctcc tgtttcagcc      480
cccagagtag gtgagactac aggcatgcca caacttctgg ctaattttttg tatttttatt     540 agagacgaag tttcaccatg ttggtcaggc tgctctcgaa gtcctgacct caggtgatcc      600
acccacctca gcctcccaaa gtgctgggat tacaggcatg agccactgcg cccggtctgt     660
ttcctgatgt gttaatgatc gccattgtat ctggtgtgag atggtatttc attgtggttt      720
tgatttgcat ttcactaata accagtgctg atgatctttt cttcatatgt ttgttggctg      780
cattaatgtc ttctttttgag aagtgtctgt tcatatcctt tgcccacttt ttcatggggc     840
tgtttgtttt tccttgtaaa tttgtttaag ttctttgtag attctggata ttagcccttt      900
gtcagatgga tagattgcaa aattttttctc ccattctgta ggttgcctgt tcaccctgat    960 gatagttttct tttgctgtgc agaaactctt tagtttaatt agatcccatt tgtcaattttt   1020 ggcttttgtt gccattgctt ttgatgtttt agtcatgaag tctttgccca tgcctatgtc     1080
ctggatgtta ttgcctagat tttcttctag ggttttttatg gttttaggtc ttacgttttaa   1140 gtctttaatt catcttgagt taattcttgt ataaggtgta aggaaggggt ccagtttcag     1200 tttttctgcat atggctagcc agtccttctt gatttagtat ttgtgggttt taaaaaagga    1260
gtttcccaaa atattcagtt aaacttttaa gtgacttacg tgtatatcta aatacatgat    1320 cagtaatat ttgtcttaaa ggggttttct ttgttcttttt cttattatag gaaggttaaa    1380
caatatgctt atttatgcca tagcttcaca aacaggaagg aggttttaaa tggtttagtt     1440
ccacaatttg agtagatgca tatttaaaga aacgttgttg cataataaat actgcctctt    1500
cctaaaatgc atcatgccac agccaatttt ggaaaacaca aatatgaggt gagtgtatttt    1560 tgaaaactat gtgaatataa tagatccctta attcatatttt gtggattttta tgggaaatac   1620 ttgttttcta aggcatctgt cttgcaaaaa gtcagtttct gctatgaagg atgttaaagg     1680
ggatatgtag gttaaattct gtttctgagc tttgcttcca gagtaaacac ccaacttact   1740
tttgccctaa agtattttat tgttctagta gagaagacta acaacatatt ctaaaccact   1800
aagtaattta tgtaaacttc gcttacaaac tatacttgtg tgacacttat atgagcaaaa    1860
gcattttcat atttcttact atatcattca attcttgctt accccaatgg aagtgacttt    1920
atgccccttt agagacaatg gaaatcaggt acttcgtgat ttctcttaaa aaaaaaaaaa    1980
atgaactaga aagctccaag tttggtgaat ctggaacctg ggtattccag ttccagttgt      2040
agcccttcct ccctatccat cactcctgtc tgcatgtaat tatgcaatac attgaaaaga   2100
ttaaaagatg ggtcttggac tcaggcagac ctgggtcaaa tccagattct ggcactgccc    2160
agccattgcc cctgggcaag ccatttttcct ctttgaacct catttgtgaa ttaagctaaa   2220
aatagtcccc accccatgg gactgtggga aggattaaat agaataatgc atgaaaagca     2280
aatagcagaa tggtccataa atgttaacca ttgttatgtt attatgtaat ctacaaagta    2340
cgtttagtta cacttcatga aatactttca gtttttcaaa gacaccacta atacatggga   2400
aatcaaaccc tgaaaattaa tttcacttta gcagtaaagt cacatgccag atggaaagga    2460
tagtatttca tgaacaaaga tcttactttt gagatttggt cttactttttt tctttttctt   2520 aagggagaat tatcttgtgt ttttttgtttt gttttgtttt gagatgggagt cttgttctgt  2580
```

```
cacccaggct ggagcgcagt gacgtgatct cggctcactg caaccttcac ctcccgggtt    2640
caagagattc tcctgtctca gcctcccgag tagctgggac tacaggtacg tgccaccaca    2700
cctggctaat ttttgtattt ttagtagaga caagagttac accatattgg ccaggatctt    2760
ttgctttcta tagcttcaaa atgttcttaa tgttaagaca ttcttaatac tctgaaccat    2820
atgaatttgc cattttggta agtcacagac gccagatggt ggcaatttca catggcgcaa    2880
cccgaaagat taacaaacta tccagcagat gaaaggattt tttttagttt cattgggttt    2940
actgaagaaa ttgtttgaat tctcattgca tctccagttc aacagataat gagtgagtga    3000
tgccacactc tcaagagtta aaacaaaac aacaaaaaaa ttaaaacaaa agcacacaac     3060
tttctctctc tgtcccaaaa tacatacttg catacccccg ctccagataa aatccaaagg    3120
gtaaaactgt cttcatgcct gcaaattcct aaggagggca cctaaagtac ttgacagcga    3180
gtgtgctgag gaaatcggca gctgttgaag tcacctcctg tgctcttgcc aaatgtttga    3240
aagggaatac actgggttac cgggtgtatg ttggaggggg agcattatca gtgctcgggt    3300
gaggcaagtt cggagtaccc agatggagac atccgtgtct gtgtcgctct ggatgcctcc    3360
aagccagcgt gtgtttactt tctgtgtgtg tcaccatgtc tttgtgcttc tgggtgcttc    3420
tgtgtttgtt tctggccgcg tttctgtgtt ggacaggggt gactttgtgc cggatggctt    3480
ctgtgtgaga gcgcgcgcga gtgtgcatgt cggtgagctg ggagggtgtg tctcagtgtc    3540
tatggctgtg gttcggtata agtctgagca tgtctgccag ggtgtatttg tgcctgtatg    3600
tgcgtgcctc ggtgggcact ctcgtttcct tccgaatgtg gggcagtgcc ggtgtgctgc    3660
cctctgcctt gagacctcaa gccgcgcagg cgcccagggc aggcaggtag cggccacaga    3720
agagccaaaa gctcccgggt tggctggtaa gcacaccacc tccagcttta gccctctggg    3780
gccagccagg gtagccggga agcagtggtg gcccgccctc cagggagcag ttgggccccg    3840
cccgggccag cctcaggaga aggagggcga gggagggga gggaaagggg aggagtgcct     3900
cgccccttcg cggctgccgg cgtgccattg gccgaaagtt cccgtacgtc acggcgaggg    3960
cagttcccct aaagtcctgt gcacataacg ggcagaacgc actgcgaagc ggcttcttca    4020
gagcacgggc tggaactggc aggcaccgcg agccctagc acccgacaag ctgagtgtgc     4080
aggacgagtc cccaccacac ccacaccaca gccgctgaat gaggcttcca ggcgtccgct    4140
cgcggcccgc agagcccgc cgtgggtccg cctgctgagg cgcccccagc cagtgcgctt     4200
acctgccaga ctgcgcgcca tggggcaacc cgggaacggc agcgccttct tgctggcacc    4260
caatggaagc catgcgccgg accacgacgt cacgcagcaa agggacgagg tgtgggtggt    4320
gggcatgggc atcgtcatgt ctctcatcgt cctggccatc gtgtttggca atgtgctggt    4380
catcacagcc attgccaagt tcgagcgtct gcagacggtc accaactact tcatcacttc    4440
actggcctgt gctgatctgg tcatgggcct ggcagtggtg ccctttgggg ccgcccatat    4500
tcttatgaaa atgtggactt ttggcaactt ctggtgcgag ttttggactt ccattgatgt    4560
gctgtgcgtc acggccagca ttgagaccct gtgcgtgatc gcagtggatc gctactttgc    4620
cattacttca ccttcaagt accagagcct gctgaccaag aataaggccc gggtgatcat     4680
tctgatggtg tggattgtgt caggccttac ctccttcttg cccattcaga tgcactggta    4740
ccgggccacc caccaggaag ccatcaactg ctatgccaat gagacctgct gtgacttctt    4800
cacgaaccaa gcctatgcca ttgcctcttc catcgtgtcc ttctacgttc cctggtgat     4860 catggtcttc gtctactcca gggtcttca ggaggccaaa aggcagctcc agaagattga     4920
caaatctgag ggccgcttcc atgtccagaa ccttagccag gtggagcagg atgggcggac    4980
```

```
ggggcatgga ctccgcagat cttccaagtt ctgcttgaag gagcacaaag ccctcaagac     5040
gttaggcatc atcatgggca cttcaccct ctgctggctg cccttcttca tcgttaacat      5100
tgtgcatgtg atccaggata acctcatccg taaggaagtt tacatcctcc taaattggat    5160
aggctatgtc aattctggtt tcaatcccct tatctactgc cggagcccag atttcaggat    5220
tgccttccag gagcttctgt gcctgcgcag gtcttctttg aaggcctatg gaatggcta     5280 ctccagcaac ggcaacacag gggagcagag tggatatcac gtggaacagg agaaagaaaa   5340
taaactgctg tgtgaagacc tcccaggcac ggaagacttt gtgggccatc aaggtactgt    5400
gcctagcgat aacattgatt cacaagggag gaattgtagt acaaatgact cactgctgta    5460
aagcagtttt tctactttta aagacccccc cccgcccaac agaacactaa acagactatt    5520
taacttgagg gtaataaact tagaataaaa ttgtaaaatt gtatagagat atgcagaagg    5580
aagggcatcc ttctgccttt tttatttttt taagctgtaa aaagagagaa aacttatttg    5640
agtgattatt tgttatttgt acagttcagt tcctctttgc atggaatttg taagtttatg    5700
tctaaagagc tttagtccta gaggacctga gtctgctata ttttcatgac ttttccatgt    5760
atctacctca ctattcaagt attaggggta atatattgct gctggtaatt tgtatctgaa    5820
ggagattttc cttcctacac ccttggactt gaggattttg agtatctcgg acctttcagc   5880
tgtgaacatg gactcttccc ccactcctct tatttgctca cacggggtat tttaggcagg    5940
gatttgagga gcagcttcag ttgttttccc gagcaaagtc taaagtttac agtaaataaa    6000
ttgtttgacc atgccttcat tgcacctgtt tctccaaaac cccttgactg gagtgctgtt    6060
gcctccccca ctggaaaccg caggtaacta cttgtaatta ctgcccatga cttaatgtag    6120
aatgatacaa gaatgacatg cacagattgc ttaacccttt catttgcctt tgagtctgct    6180
gctgcaaagc tgcatctctc ctgacacttg tgccccaaat cagttctgcc tgctcttagt    6240
atagctcaac tctccctatg gttattgttc tgtgttgtta cctcagaaac actgactcac    6300
agaagcggag ttaaggggat atgtttttt ctctccacgt gcacccacca cccaccttcc     6360
agttctactt gtttcaaaac tgtttatatt tctgtcttgg ccatgtgtta cagtggagct    6420 cttttgtactg catcagggct tggcatttta gggataagga agatgttctt atgaggaagc   6480
tactcagaca tggccccgta attctgaggg aaaattcaaa aggcattggt catggggaga    6540
aaagctggag aacacataac tgatggatac ctcatgaact agaaacagaa ttttaacccc   6600 tttttccttct ttccttttggt ccctgttttc ttctcccact gactctcctc gattcagtgt  6660
aaaccaaggt tctgagtctt agcactgtta gcattttgga ccagataact ctttgttatg    6720
ggggctgcat cattgtatgt gtagcacctc tggcctctgt tcattagatg ccaatagcac    6780
cccctgctta taacaagcaa aaatgtttcc agacattgca aaagagcccc tgaggtgcga    6840
attagcccct ggttgagagt cactggtaga aactgtaaaa atctcagcag atacatacat    6900
tctttctaat gcaagcgctt gattgtgcag agccttagag agggattttc acagttcacc   6960
taggcagtaa cagaccctca ccagcactct ttccattcca tcatgctgcc ttctaaactt    7020
gttttctagc tgcccaaata gtgatcatga aatgttaaga aggctttaag tctgtacatg    7080
aattgtttga gagggtttat caatggaggt gaggcctgtg ggccatgact cctgtttgtg    7140
aagagattat aatactgtca agaggcacgt taggggaaat cacaaaagta aacacatttc    7200
ttctcccagc ccctttctat ttttgcctgt gtgtctgagc cagagcttgg cccaggtttg    7260
atgaagtgga tcgtcctcct tggcaacgcc aggctagagc agatcagcct gcagggttca    7320
ttgccattcc actggctcat gaagctgact ccactcccct cttcctttct gttgcagcca    7380
```

```
aggtccccaa ccagaaaagc attggccttc tctgcttcct gtcaactcaa tgatgggatg   7440
tttgggtgag caccgagcta tcaggagaag gttaggcgcc tgtgattttg aacatgcca    7500
tggcaaattg gagaatgtgt gtcattcagt gcttttactt ttttccaagg gttttcatac   7560
ctattgaaaa cccttattac acattatcac cttctctttc tactgctatt atcacattct   7620
ctttctactg ctctggtctc cacactcaga gatttgggca gcttctttgg ctaatattca   7680
tgctccctgt agcctcataa gatctcagac atggaagagc ccatagaaag tatttaacat   7740
ctgatgagac tgaaacgctg tgaggtgaag ggcttgccca aggtaagcag ccaaggatgt   7800
cagagtggga ctcaagccag ggaacccaac tgctattcca ggaactgctg cattctctcc   7860
accacattag cattgcgttc tttcctcacc ctcaactggg gctataacat aacacattca   7920
tttcagccaa tatattttc ttttgtcctt aacacaaaat ttagagcata aacaaataat    7980
ctgcaataga gacaaaagaa ataattgttc atttaactca acaagcatcc actaggatat   8040
cttctgcatt tagggaagct gggagattcc ttagctcttt ataaccagat gtcggtgttg   8100
tatatatact cttttgccta aaggaatgtc taatgtaatt tctgttaaaa ttcaggtatt   8160
aatgttaatt cagattccca gctaaaagga gagtttaacc atattcacgt tcctttagga   8220
atactgtaga cacaagaacc ttgattagtt ttaagggtcc tgataagcaa gagcattcta   8280
ggcatatctt aatcctttgc tttctacctc tttggtgtgt tgctttgttt cttttgaggg   8340
gttggctttt gtcagtgtcc cttcgtctct ctgtttgctg acatgctggc cacctaaggt   8400
ttgtgttgta ttcctcatcg tgagttttt ttttgcctgg acagcaagtt ctcagagtct    8460
gtcaaataag aagaactttt ttctaagatg caagctgaga ggtgtgaaca gtggcaggac   8520
agggtgagcc tccccactgc aataattaat gggataagga atctggagaa aggggagctt   8580
gagaatagga actgtcttta catgattctt agaatgtttc ttatggtgaa cctattgcca   8640
aatggagcct aaaccagaat cagtcagaaa gtatttatgg agcacctact gtatgcagca   8700
tgagaaaagt ataggtttcc atttctgcct tttggatcat gatattaagg atactaagca   8760
gataccttt atggaatctt actaaaagtt agtgactatg ttagacacct gttaggcgtt    8820
atgtcctcac aactgtatga tgtaggtagc ataattgtcc tcatctaaca aatgagggag   8880
ctgaggctca gaaagcttca gtaactttcc aaagccatac aaccaactag ttgcagagtc   8940
aggacgagaa cccaggtctc tgtgattcca ggatccatgg agcctagcac ccaggcaaac   9000
caggaagcag cacgaggtag cttagaatct gtgccagaac aagtgtaaga actggaaatg   9060
caatactttg ttgagagaag acggagactg ctgtgggttg aggcagggag gaatgttccc   9120
ttccaagcat gtgactgcag ggtttctggg gactgacaca aaaaccaat cactgaagtg    9180
cctagtttgc ttctccaagt ctttgttttg tcttctcatc agagaatcag accaaaatgg   9240
aaagaggata tgaaactcta aaacgaacac agcagagtaa agcagaaaca caggctgccc   9300
tacgtcctgg cactctttct cagctccaaa gttgggaagg cctcctaaat tgagtgggta   9360
gccagacctt atgaaatttt gataggcctg ggtagccata taggtatgtt ttccatcttg   9420
agctagcatt ctagatcaaa ggagatgatt ttctgacagc agagagcaag gaagcttaat   9480
atgctttgaa tgatactttc cattgacagt ataacctcta ctaaattcag tctgtgctaa   9540
tccatacttc actgacagtg caaatataat ttgaaggagg attttttcta aatgcgtaag   9600
agaacaaact tcctaagcac tttcaagaac ttgagaaatt ctggtgtttt gtgaataata   9660
ggaggcaggg tgaggtgaaa agagccccc tccaacctcc cacccaccac cccactctct    9720
ctctctctga agttgggtga ggcggttttc ttcagccgac ttccgtttac tcatctgtaa   9780
```

```
tttgaggcca gtacaggtgg tatctaagct ctgctcccct ctgaatttat acagttgtta    9840
atttacaggc tagagataat catttatatt tctaattaga gttgatgaca tttgccatat    9900
aaacaatggt tgaatattct gaaggttgtc agcctgcaga agagaatgct gtgaagtact    9960
atttggtg                                                             9968
```

<210> SEQ ID NO 2
<211> LENGTH: 11265
<212> TYPE: DNA
<213> ORGANISM: Homo sapiens

<400> SEQUENCE: 2

```
acttttgtat atctatctgg aaggatcaca gatacatagt caaattaaaa taagcaaggt      60
gcagaacagt gggtatatat gactgctatt tgtatagaaa agaaaggata aagaatata     120 tatatttgta ttgacttgta tctatataaa atatgagccg agggataaac cagagactaa    180
tggtagttac ctgctaggga gatgaaaact gggatgaagg caagtctcta ttatatgcat    240
ttgttatatt ttgatggttg aataatgtgc acgtataatc tattcaaaat attaagttat    300
aaaacacaaa atcacaaaag agacccaata gtctatagac taaggtggca aaagagggag    360
cccattcccc ctgccatctg cttgggcggg ggaaaaccag actgaggaat gagagcaggg    420
atgagttggc agaggaggaa gaagccaagt gtctcaacat tgatggattt gctcataaaa    480
ccatccctaa ccggagtcag aaatttctct tcttacagtg tcgtttggtt attggcctaa    540
tcattcccca aactcaggca cactcaggtg gtttgagaaa tcctgtcttt tttgaaaatg    600
ttaaacattt ttacacactt cttccaaatt acaaggtcac ccctaaggca ttgacatcat    660
tgaggttgct tcactttccg gcaccccttt cccttcccc tccaatgctg atgtcctgga    720
aaaaaattgc tgaatggcat gcattgattt tggagattac ttttggaa tcttatgata     780 tcccttgag ataactggca acaacactct ggggtgctgc aaaaccctac ttgggagtga    840
ctgccttgct ggtcaacagg aagccacagc caagactctg tgcccagtgg ggcctgcacc    900
actctgtcat gacttgagtg ggggcagtaa gaggtggaag gggccagagg ctgcctcttc    960
actttcaccc ccatggattt ccatggatcc aaaggcctgc ttggggttct tcatgggcat   1020
agaagtcact tgcttgggag cccaagacaa accctgctca tgggtgagca gctgggtccc   1080
tgggagacga ggctggttct ttttccttgg ggataatttt aggttctgaa ttcccctgca   1140
accttcctaa ctcccagccc ccagctcagc ctcccagagg gattgttcat accagtgact   1200
ataaagtgtt ctctcgaaat atagagctgt tcagagacct gccagggcat agccctggag   1260
gcatttccca tgataatttt tcccccttttg tcccattgtt tcagaggagg aagcatgata   1320
gctcaagaat caggtcctga tagtccctga taaggtgtca catcttcctg cctctccact   1380
tgaaccctgg ggctttattt tccagcgccc ccctcccgt acgcaatctg agaggaactg    1440
gtttagagat tgagagagca ggggctggaa aaaggaagcc ttgcaagtct tgagtgaggg   1500
cagggagaag ggaagaggaa gagggaagcc tctggtggaa ccgcctaaga gacttcagag   1560
gctttgaaac accaggcctg ccaccacaca cgctcaaaaa tgaacgcatg aattcctcaa   1620
ctcaacgcct tctagttttt aaaagttaat gaatgaaatc cttaaggaag tccggacacg   1680
gtgactcaca cctgtaatcc cagcattctg ggaggccgag gcgggtggat catctgaggt   1740
caggagtttg agaccagcct ggccaacatg tgaaacccc gtctctacta aaaatacaaa    1800
aatttgctgg gcttggtggc acatgctcat cccagctact gggtggctg ggaggcttgg    1860 gaggctgagg cagaagaatt gcttgaacct gggaagtgga ggttgcagtg agcagagatt   1920
```

```
gtgccactgc actccagcct gggcaacaag agcaaaattt catctcaaaa aacaaataaa    1980
caaacaaaaa acctaaagga agtggagcga acacttacca ttggggagat ggcaatggaa    2040
gagttgtgta tagtttgggg ggatggtgga cctgcctcat acccagtcac ccatttaccc    2100 atttttttt ttaaaatagg gtcttgcttc ttgccgtctt ccaagctgga gtgcagtagt    2160
agcatgatca cagatcactg taaccttgaa ctcctgggct caagcgatcc tctcctctca    2220
gcctcttgat tcatcctttc tttttttttt tttttttttt ttttctgata tggagtttcg    2280
ctcttgttgc caaggctgga gtgccatggt gtgatctcgg ctcactgcaa cctctgcctc    2340
ccaggttcaa gagattctcc tgcctcagcc tcttgagtag ctgggattac aggcatgcgc    2400
caccacacct ggctaatttt tttttttttt ttttgtattt ttagtagaga cagggtttct    2460
ccttgttgtt caggctggtc ttgaactcct gacctcaggt gatctgccca cctcgacctc    2520
ccaaagtgct gggattacag gcgtgagcca ccgcgcccac ctgttgattc atccattttt    2580
aatatgtctt tatagcagaa agattttaag agaaggggc atctagaaaa tctctaggtg    2640 gaaggtgca tggaaggggc agtgcagagt ggggaagatg gagaaattga aattcttcag    2700
catcccagac tacatagtgc caaatccaaa tgcaaatcca gagctagcaa tgaaaaagac    2760
tcctggccgg gcgcgatggc tcacgcctgt aatcccagca ctttgggagg ccgaggcggg    2820
cggatcacga ggtcaggaga tcgagaccat cctggccaac atggtgaaac cccgtctcta    2880
ctaaaaatat aaaaattagt tgggcatgct ggcgggtgcc tgcagtccca gctacttggg    2940
aggctgaggc aggagaagcg cttgaacccg ggaggtggag attgcagtga gcagacatca    3000
catcattgca ctccagcctc agcctgggt gacagagcga acgccgtct caaaaaaaaa    3060 aaaaaaaaga aaagaaaaag aaaaagactc ctgagcctcc tagtggttca cgcctgcaat    3120
tccaactact caggaggctg ggacaggagg gtggcttgag cccgggagtt caaagccagc    3180
ctgggaaaaa tagagagaga gagagagact tgaaatatgg taaatttcct cagtacctga    3240
aaatattaaa aaaaacaaaa agctagaagg aaagagaagg taactgaaac agaagggaaa    3300
ggggacagat ctcaccaagc tgaggtcttg ggagaggaga tactggctga gccctattac    3360
ttaatttaaa ataccttagg ggaggccacc caagtggatg cggggctcct gtgaatcctt    3420
tgcttgactc cagcgggtta cctttgcctc tgatacataa agggtgggga tgggagcgct    3480
ctcctctctc cttcccctgc cttgctgtgg gaacttctgg gaaaggaggt gcagggctcc    3540
aggaagccag tgcccaggga gtgctatgct gagtccagga gcctggccac ggcaggggtg    3600
gacagatggt ggcagaggaa ccacggtgtc ccttcctcca gatttaagct aaaggaaacg    3660
tggagcatcc cattggccat cctccccact ctccaattcg gctccagagg cccctccaga    3720
ctataggcag ctgcccctt aagcgtcgct actcctcccc caagagcggt ggcaccgagg    3780 gagtggggt gggggaggc tgagcgctct ggctgggaca gctagagaag atggcccagg    3840
ctggggaagt cgctctcatg ccttgctgtc ccctcccctg agccaggtga tttgggagac    3900
cccctccttc cttctttccc taccgcccca cgcgcgaccc ggggatggct ccgtggcctc    3960
acgagaacag ctctcttgcc ccatggccgg acctccccac cctggcgccc aataccgcca    4020
acaccagtgg gctgccaggg gttccgtggg aggcggccct agccggggcc ctgctggcgc    4080
tggcggtgct ggccaccgtg ggaggcaacc tgctggtcat cgtggccatc gcctggactc    4140
cgagactcca gaccatgacc aacgtgttcg tgacttcgct ggccgcagcc gacctggtga    4200
tgggactcct ggtggtgccg ccggcggcca ccttggcgct gactggccac tggcgttgg    4260 gcgccactgg ctgcgagctg tggacctcgg tggacgtgct gtgtgtgacc gccagcatcg    4320
```

```
aaaccctgtg cgccctggcc gtggaccgct acctggctgt gaccaacccg ctgcgttacg   4380
gcgcactggt caccaagcgc tgcgcccgga cagctgtggt cctggtgtgg gtcgtgtcgg   4440
ccgcggtgtc gtttgcgccc atcatgagcc agtggtggcg cgtagggggcc gacgccgagg   4500
cgcagcgctg ccactccaac ccgcgctgct gtgccttcgc ctccaacatg ccctacgtgc   4560
tgctgtcctc ctccgtctcc ttctacctcc ctcttctcgt gatgctcttc gtctacgcgc   4620
gggttttcgt ggtggctacg cgccagctgc gcttgctgcg cggggagctg ggccgctttc   4680
cgcccgagga gtctccgccg gcgccgtcgc gctctctggc cccggccccg gtggggacgt   4740
gcgctccgcc cgaagggggtg cccgcctgcg gccggcggcc cgcgcgcctc ctgcctctcc   4800
gggaacaccg ggccctgtgc accttgggtc tcatcatggg caccttcact ctctgctggt   4860
tgcccttctt tctggccaac gtgctgcgcg ccctgggggg cccctctcta gtcccgggcc   4920
cggctttcct tgccctgaac tggctaggtt atgccaattc tgccttcaac ccgctcatct   4980
actgccgcag cccggacttt cgcagcgcct tccgccgtct tctgtgccgc tgcggccgtc   5040
gcctgcctcc ggagccctgc gccgccgcc gcccggccct cttcccctcg ggcgttcctg   5100
cggcccggag cagcccagcg cagcccaggc tttgccaacg gctcgacggg taggtaaccg   5160
gggcagaggg accggcggct cagggtcggg aagcatgcga tgtgtccgtg ggtcaacttt   5220
ttgagtgtga agtttattaa gagaaggtgg gatggctttg cttggagaga aaagggaacg   5280
aggagtagcg aaccaaaatg ggacccaggg tccttttctt tccggatcca gtcactaggg   5340
tagaagcaaa ggagggcgag cgggccgtcg ttcctcaccc aaggacccaa ggtgcgccac   5400
cggaaagcgc tgcggtgtcc cgaggactct cgcctcgcct ggtcggcttt agggattttt   5460
ttttttttta aatagagaca gggtttcgtc tctgtcgccc acgcgggaat gcagtggcgc   5520
gatctcagct cactgcagtc ttgaactcct ggctcctggg ctcaagcgat cctcccacct   5580
cagcctcctg agtatctggg actacaggcg agccccacca atcccagcta tttttaaaat   5640
ttcttgtaga gatggggtct tgctatgttg cccaggcttg tcttgaactt ctggcctcaa   5700
gtgatccttc tgcctcagcc ttccaaagca ttaggattac aggccggagc cagggcgccg   5760
ggtcggctct agttttggtt ttccagctca gttctttgcc cccctcccccc gatttcttgc   5820
catcactaga cctggctcgg acttgaaggc agggctagtg ccccccccacc cgccccccaa   5880
gccctcggcc tcagttctgg gttttctcaa aggtttgaca gctgtggagg tgagaatcca   5940
cttccggtat gaagtacagt tgtgagtgag gagcctgtga gtgcagatgt gtgccctccc   6000
gctccctggg ctgggttgga gtagggatgg ggtggggcgt gtgtggctgg gtggtgccct   6060
ggcgttttg tgtaactaaa tatgcgttcc agggtctctg atctctgtca ttcccctcag   6120
tgcacctgtt gctcctttca ccccagggtc tattatctcc actttttttc ccagggcttc   6180
ttggggagtt tcttaggcct gaaggacaag aagcaacaac tctgttgatc agaacctgtg   6240
gaaaacctct ggcctctgtt cagaatgagt cccatgggat tccccggctg tgacactcta   6300
ccctccagaa cctgacgact gggccatgtg acccaaggag ggatccttac caagtgggtt   6360
ttcaccatcc tcttgctctc tgtctgagag atgttttcta aacccagcc ttgaacttca   6420
ctcctccctc agtggtagtg tccaggtgcc gtggagcagc aggctggctt tggtagggc   6480
acccatcacc cggcttgcct gtgcagtcag tgagtgctta gggcaaagag agctcccctg   6540
gttccattcc ttctgccacc caaaccctga tgagaccta gtgttctcca ggctctgtgg   6600
cccaggctga gagcagcagg gtagaaaaga ccaagatttg gggttttatc tctggttccc   6660
ttattactgc tctcaagcag tggcctctct cactttagcc atggaatggc tccgatctac   6720
```

```
ctcacagcag tgtcagaagg acttcgccag ggttttggga gctccagggt tcataagaag    6780
gtgaaccatt agaacagatc ccttcttttc cttttgcaat cagataaata aatatcactg    6840
aatgcagttc atcctcggcc ccctttccct ccgtttgttt tcttttcata atccacttac    6900
tcccttccct tctactctgc gctggctttt gacagaggca gtaaattagg cctaatcctc    6960
actcttttct tcctaatctt catcaaacaa aaaatgaaaa gtctgtctgg acgaagggga    7020
gtgagcttga gcctttgata tcttgctccc ccacccttcc tgaaactctt gaaatccagt    7080
tgccattgag tagcaaagcc acgctcccca caggacttgg acagagggcc cacaggggga    7140
tgggctggct gtggccaggt ttagggcagg gggcatttgt cccctccatg ctataatcca    7200
gtggtgcctt acatggtgtg tgtgtgtgtg tgtgcgtgtg tgtgtgtgtg tgtgtgtctg    7260
gaggcacagg cacaaagcat tgcttgggtt ggtcaaatgt cttgtgtcat aaatatattc    7320 tgatgttttcc cagcctttcc acaacctcta ccttcccact caccttcccc agctacaaaa    7380
atctgtatta tcctcttaaa gtaaaactgg agttacaaat ttgagcctgt tgatgcagtt    7440
ttctcttatt tccattttat gaatcttatc agccaggttt cctatgtaaa gaaaatttct    7500
aaggaaatca ttagatcatt ttgtgagttt ctatttaaac tctatgagcc aagactattg    7560
tccaggatga tttatggaat gcccggtaaa tcacagatgt tttgcgtgtt tgtgatgtag    7620
tgcgcaatgt gttgtcttgg ttcaggggcc ctagagttat aaaattccat ctgccccaag    7680
gaggagctcg atagatttcc acatatgggt gttccctgtg aattggacct ggtctgtgct    7740
gctctctttt ctccaggagc ccaggtttta tttctcagga tgttttcata ccaaagatga    7800 cttctcctt ttcaaccagg gcagggtgag atctctggtg tctgaggtgt gcaagatttc    7860
ttggcaaaga ctcaactttg tggctgttag tggaggagga agtcttgctt gacaaataag    7920
aggccctcct ctccccatct ctggatattc tcccaacatc gctggataaa attggccagt    7980
cagtgctagg caggggagaa tgatgatgtt ggaggtgggg cccctggtgt gtagacttgt    8040
ccttgaacat tgtccagaag ctcatactgc ttgagtcttg ttggacttgc ccgtgcgcca    8100
gctgtcacac tccttttgcag tgtttagact tgtgctgggg ctatggattc catctgcaga    8160
ttgtcagata gaatctgaca gtctggtcat ttctccagca acttgtggcc aggcatcaag    8220
tggagggaga tttacatcct tggatgggag caggctgctt ttgctagcat gaggcctgag    8280
cacttgaact gtagaagaca aacagctgtc ccctgaaccc agagatatga tgacttccag    8340
gcccgtgaga caacagagt ccctagagcc gctggcctcc ccagagtctg ttagctggag    8400
ctgggcatgg gacagaaatg acatggaaga gagggctgag ttggaggaga gggaatgaag    8460
agcgggcttt ttcagagctg acctaccctc tgcatcaagt ggaactgagg gggaacaggc    8520
agaatttggg tacaggagga tgtggggggc tgactttccc agactttctt ctggggaatg    8580
gaggtaggtg caggctgtgg tcctcacggg cagtccctgg gccttagtcc catgctgact    8640
gcatcctcaa ccctaggaga gtaggagcag ctcctctcct ctgtgtgttt ccattgcacc    8700
ctacatggtc ctaggagcac aggggaaggc atgggaatag cgcttcttac tgttttcatc    8760
ttaaaactgc ctagatccag gccttttgaa ggcctcttgg cgaaggtatg tctacacact    8820
gtctgtgttt gggtgtctgt ccagaacggg gaaatgggag cctgccatgg caagcactgc    8880
taatgctctc ccccacacaa caagccctgg gtatagtctg cctttggcca gtgagaagca    8940
gctgaagcat aacatgcaat tcagtttaat ttgaggccga ggtgggcgga ttacctgagg    9000
tcaggagttc gagaccagcc tggccaacat ggcaaaaccc cgtctctact aaaaatacaa    9060
aaattagccg ggcatggtgg tgggtgcctg taatcccagc tacttgggag gctgaggcag    9120
```

```
ggagaatgct tgaacccggg aggcagaggt tgcagtgagc ctagatggca ccactgcact   9180
ccagcctggg caacagagtg agactccatc tcaaaaaaaa aaaaaaaaaa aaaagggaca   9240
aggaaaaaga cagtctcata gaaatcaaat aacttccttg tatcgactct caccccatct   9300
accagattcc aaagtccatt ttctcttctc tatatgcact gcttagaagc agttgtgtga   9360
cactgaacaa gtcacttagc ctttctgact gtttctttgc ctgtgagtca actggagatt   9420
acatgatcac tctactcagc tcatgcaggc tgcttttgaa gacccggtga gacactgtgt   9480
gtgaaagtgg tttggaaact gaaaatgctt ctccggtata aagcggtgaa atcagaatct   9540
ggagcttgga tgagtcccag gtctattata gcagggatcc ccaacccctg ggccgcagac   9600
tgctactggt ctgtggcttg ttaggaactg ggctgcagcg caggaggtga gtggagggca   9660
agcgagcatt aacacgtgag ctccgcctcc tgtcagatct gcggctgcgt tagattctca   9720
ctggagcgcg aatcctaaag tgaactgcac atgtgaggga tctaggttgc atgctctttc   9780
tgagaatcta atgtctgata atctgaggtg gcagctttat cccaaaacca tctccttctc   9840
ccctgtccgt ggaaagattg ccttccacca aaccggtccc ttgtgccaaa aggttgggg   9900 atcactgtct tatagggtct tgctctgttg cccaggctag agttcagggg cacaatcatg   9960
gcttattgca gcctcagcct cctgctcaag tgatcctctt atctcagcct cccaagtggc  10020
caggactaca ggcttgcacc actatgccca gctaattaaa tttattttt tgtgagact  10080 gggtatttct atgttgccca ggctggtctt gagctcctgg gctcaagagt tcctcctgcc  10140
tcagcctccc aaagtgctgg gattatgagc atgatccact gtgcctggcc ctggttttgc  10200
tccctgtata ttcctgtttc tgtcgacagc ctgggtcttg acccacttg tctttggtct  10260 ttgtggacat gccctgcctg gtcttctc tgcaagtttg tactcacctc agactgactg  10320
ctttggtttt ctgtcctggt ctttatacat ctccacctct ggctctgttt ccatgttcag  10380
accctggtct ggcccgatat tttgctcctg gtctggatca ccccatcatt accaatgcaa  10440
catttacaac gagaacaatt ttaagaatgg gtaggccagg cgcagtggct cacgcctgta  10500
atcccagcac tttgggaggc cgaggcgggt ggatcacctg aggtcaggag ttcaagacca  10560
gcctggccaa catggtgaaa tcccatctct actaaaaata caaaagttag ccgggcgtgg  10620
tggcaggcgc ctgtaatcac agctgctcgg gaggctgagg caggagaatc gcttgaaccc  10680
agggaggcag aggttgcagt gagccgagat tgtgccactg cactctcaaa aaaaaaaaa  10740 aaaaaaaaa aagaatgaga agatttagaa cagaaggtac ttctggatct caggacatta  10800
tggtctatta tagtagggg ttcatgagaa tgggacccta aggaaccaga aaggggagag  10860 aagtggcgt atactttgct agggctgcca taacaaatga ctacaaactg ggtggcttaa  10920
cacaggagga actgattctc tcacagtgct ggagactaac agtccaaaat caaggtggca  10980
gcagggctgt gctccctgtg aggcgggagg ggaagatcct tccttgcctc ttctcttatc  11040
ccggtgtttg ctgacaatcc ttgggattgt ttgactggag ctgtatcact ctaacttctc  11100
ccccatcttc acaaggcctt cccctgtctg tctgtgccca catttctctc ctcttataag  11160
gacatcggcc attggatcag ggctcaacct aatccagcat gacctcattt gaacctggtt  11220
acatgtgcaa agaccccatt tccaaataag gtcacattca caagt            11265
```

<210> SEQ ID NO 3
<211> LENGTH: 472
<212> TYPE: DNA
<213> ORGANISM: Homo sapiens

<400> SEQUENCE: 3

```
cttgggtagt gacaaagtat taatttatta ggtgaagtat atgctttttt attagtgata      60
ataaatatat cctctctccc attataaaag tttgtatttc ttcttttaga aattgattct     120
tctgtcattt gcacatttat ctgtataatt ataacagggt atttcccagt ggtggctaat    180
gagagaatta tgggaaagta tagaacacta ttcaaatgca aagcactgta tgatttttat    240
ttaataggaa gacattttgt gcagcgattt ctgattgacc acagtttgat caagtgcatt    300
tgttaatgtg ttctacattt tcaaaaagga aaggagaatt tgttacattc agaacttgct    360
gccactcctt tgctacgtca taaagggtca gttgcccttg ctcatactga cctattcttt    420
accctctctg cttcttcttt gtgccagaag agtagaaatc tgacccttg gg             472
```

```
<210> SEQ ID NO 4
<211> LENGTH: 25
<212> TYPE: DNA
<213> ORGANISM: Artificial
<220> FEATURE:
<223> OTHER INFORMATION: forward primer

<400> SEQUENCE: 4
ggcaacccgg gaacggcagc gcctt                                           25

<210> SEQ ID NO 5
<211> LENGTH: 24
<212> TYPE: DNA
<213> ORGANISM: Artificial
<220> FEATURE:
<223> OTHER INFORMATION: forward primer

<400> SEQUENCE: 5
gcaacccggg aacggcagcg cctt                                            24

<210> SEQ ID NO 6
<211> LENGTH: 23
<212> TYPE: DNA
<213> ORGANISM: Artificial
<220> FEATURE:
<223> OTHER INFORMATION: forward primer

<400> SEQUENCE: 6
caacccggga acggcagcgc ctt                                             23

<210> SEQ ID NO 7
<211> LENGTH: 22
<212> TYPE: DNA
<213> ORGANISM: Artificial
<220> FEATURE:
<223> OTHER INFORMATION: forward primer

<400> SEQUENCE: 7
aacccgggaa cggcagcgcc tt                                              22

<210> SEQ ID NO 8
<211> LENGTH: 21
<212> TYPE: DNA
<213> ORGANISM: Artificial
<220> FEATURE:
<223> OTHER INFORMATION: forward primer

<400> SEQUENCE: 8
acccgggaac ggcagcgcct t                                               21

<210> SEQ ID NO 9
<211> LENGTH: 20
```

```
<212> TYPE: DNA
<213> ORGANISM: Artificial
<220> FEATURE:
<223> OTHER INFORMATION: forward primer

<400> SEQUENCE: 9
cccgggaacg gcagcgcctt                                              20

<210> SEQ ID NO 10
<211> LENGTH: 19
<212> TYPE: DNA
<213> ORGANISM: Artificial
<220> FEATURE:
<223> OTHER INFORMATION: forward primer

<400> SEQUENCE: 10
ccgggaacgg cagcgcctt                                               19

<210> SEQ ID NO 11
<211> LENGTH: 18
<212> TYPE: DNA
<213> ORGANISM: Artificial
<220> FEATURE:
<223> OTHER INFORMATION: forward primer

<400> SEQUENCE: 11
cgggaacggc agcgcctt                                                18

<210> SEQ ID NO 12
<211> LENGTH: 31
<212> TYPE: DNA
<213> ORGANISM: Artificial
<220> FEATURE:
<223> OTHER INFORMATION: reverse primer

<400> SEQUENCE: 12
ccaccaccca cacctcgtcc ctttsctgcg t                                 31

<210> SEQ ID NO 13
<211> LENGTH: 30
<212> TYPE: DNA
<213> ORGANISM: Artificial
<220> FEATURE:
<223> OTHER INFORMATION: reverse primer

<400> SEQUENCE: 13
caccacccac acctcgtccc tttsctgcgt                                   30

<210> SEQ ID NO 14
<211> LENGTH: 29
<212> TYPE: DNA
<213> ORGANISM: Artificial
<220> FEATURE:
<223> OTHER INFORMATION: reverse primer

<400> SEQUENCE: 14
accacccaca cctcgtccct ttsctgcgt                                    29

<210> SEQ ID NO 15
<211> LENGTH: 28
<212> TYPE: DNA
<213> ORGANISM: Artificial
<220> FEATURE:
<223> OTHER INFORMATION: reverse primer

<400> SEQUENCE: 15
ccacccacac ctcgtccctt tsctgcgt                                     28
```

<210> SEQ ID NO 16
<211> LENGTH: 27
<212> TYPE: DNA
<213> ORGANISM: Artificial
<220> FEATURE:
<223> OTHER INFORMATION: reverse primer

<400> SEQUENCE: 16
cacccacacc tcgtccctttt sctgcgt                                       27

<210> SEQ ID NO 17
<211> LENGTH: 26
<212> TYPE: DNA
<213> ORGANISM: Artificial
<220> FEATURE:
<223> OTHER INFORMATION: reverse primer

<400> SEQUENCE: 17
acccacacct cgtcccttts ctgcgt                                         26

<210> SEQ ID NO 18
<211> LENGTH: 25
<212> TYPE: DNA
<213> ORGANISM: Artificial
<220> FEATURE:
<223> OTHER INFORMATION: reverse primer

<400> SEQUENCE: 18
cccacacctc gtcccttsc tgcgt                                           25

<210> SEQ ID NO 19
<211> LENGTH: 24
<212> TYPE: DNA
<213> ORGANISM: Artificial
<220> FEATURE:
<223> OTHER INFORMATION: reverse primer

<400> SEQUENCE: 19
ccacacctcg tcccttsct gcgt                                            24

<210> SEQ ID NO 20
<211> LENGTH: 23
<212> TYPE: DNA
<213> ORGANISM: Artificial
<220> FEATURE:
<223> OTHER INFORMATION: reverse primer

<400> SEQUENCE: 20
cacacctcgt ccctttsctg cgt                                            23

<210> SEQ ID NO 21
<211> LENGTH: 22
<212> TYPE: DNA
<213> ORGANISM: Artificial
<220> FEATURE:
<223> OTHER INFORMATION: reverse primer

<400> SEQUENCE: 21
acacctcgtc cctttsctgc gt                                             22

<210> SEQ ID NO 22
<211> LENGTH: 21
<212> TYPE: DNA
<213> ORGANISM: Artificial
<220> FEATURE:
<223> OTHER INFORMATION: reverse primer

```
<400> SEQUENCE: 22
cacctcgtcc ctttsctgcg t                                              21

<210> SEQ ID NO 23
<211> LENGTH: 20
<212> TYPE: DNA
<213> ORGANISM: Artificial
<220> FEATURE:
<223> OTHER INFORMATION: forward primer

<400> SEQUENCE: 23
ggccaccgtg ggaggcaacc                                                20

<210> SEQ ID NO 24
<211> LENGTH: 19
<212> TYPE: DNA
<213> ORGANISM: Artificial
<220> FEATURE:
<223> OTHER INFORMATION: forward primer

<400> SEQUENCE: 24
gccaccgtgg gaggcaacc                                                 19

<210> SEQ ID NO 25
<211> LENGTH: 18
<212> TYPE: DNA
<213> ORGANISM: Artificial
<220> FEATURE:
<223> OTHER INFORMATION: forward primer

<400> SEQUENCE: 25
ccaccgtggg aggcaacc                                                  18

<210> SEQ ID NO 26
<211> LENGTH: 17
<212> TYPE: DNA
<213> ORGANISM: Artificial
<220> FEATURE:
<223> OTHER INFORMATION: forward primer

<400> SEQUENCE: 26
caccgtggga ggcaacc                                                   17

<210> SEQ ID NO 27
<211> LENGTH: 16
<212> TYPE: DNA
<213> ORGANISM: Artificial
<220> FEATURE:
<223> OTHER INFORMATION: forward primer

<400> SEQUENCE: 27
accgtgggag gcaacc                                                    16

<210> SEQ ID NO 28
<211> LENGTH: 19
<212> TYPE: DNA
<213> ORGANISM: Artificial
<220> FEATURE:
<223> OTHER INFORMATION: reverse primer

<400> SEQUENCE: 28
ggctgcggcc agcgaagtc                                                 19

<210> SEQ ID NO 29
<211> LENGTH: 18
```

```
-continued

<212> TYPE: DNA
<213> ORGANISM: Artificial
<220> FEATURE:
<223> OTHER INFORMATION: reverse primer

<400> SEQUENCE: 29
gctgcggcca gcgaagtc                                              18

<210> SEQ ID NO 30
<211> LENGTH: 17
<212> TYPE: DNA
<213> ORGANISM: Artificial
<220> FEATURE:
<223> OTHER INFORMATION: reverse primer

<400> SEQUENCE: 30
ctgcggccag cgaagtc                                               17

<210> SEQ ID NO 31
<211> LENGTH: 16
<212> TYPE: DNA
<213> ORGANISM: Artificial
<220> FEATURE:
<223> OTHER INFORMATION: reverse primer

<400> SEQUENCE: 31
tgcggccagc gaagtc                                                16

<210> SEQ ID NO 32
<211> LENGTH: 15
<212> TYPE: DNA
<213> ORGANISM: Artificial
<220> FEATURE:
<223> OTHER INFORMATION: reverse primer

<400> SEQUENCE: 32
gcggccagcg aagtc                                                 15

<210> SEQ ID NO 33
<211> LENGTH: 44
<212> TYPE: DNA
<213> ORGANISM: Artificial
<220> FEATURE:
<223> OTHER INFORMATION: forward primer

<400> SEQUENCE: 33
ttatttaata ggaagacatt ttgtgcagcg atttctgatt gacc                 44

<210> SEQ ID NO 34
<211> LENGTH: 43
<212> TYPE: DNA
<213> ORGANISM: Artificial
<220> FEATURE:
<223> OTHER INFORMATION: forward primer

<400> SEQUENCE: 34
tatttaatag gaagacattt tgtgcagcga tttctgattg acc                  43

<210> SEQ ID NO 35
<211> LENGTH: 42
<212> TYPE: DNA
<213> ORGANISM: Artificial
<220> FEATURE:
<223> OTHER INFORMATION: forward primer

<400> SEQUENCE: 35
atttaatagg aagacatttt gtgcagcgat ttctgattga cc                   42
```

```
<210> SEQ ID NO 36
<211> LENGTH: 41
<212> TYPE: DNA
<213> ORGANISM: Artificial
<220> FEATURE:
<223> OTHER INFORMATION: forward primer

<400> SEQUENCE: 36
tttaatagga agacattttg tgcagcgatt tctgattgac c                41

<210> SEQ ID NO 37
<211> LENGTH: 40
<212> TYPE: DNA
<213> ORGANISM: Artificial
<220> FEATURE:
<223> OTHER INFORMATION: forward primer

<400> SEQUENCE: 37
ttaataggaa gacattttgt gcagcgattt ctgattgacc                 40

<210> SEQ ID NO 38
<211> LENGTH: 39
<212> TYPE: DNA
<213> ORGANISM: Artificial
<220> FEATURE:
<223> OTHER INFORMATION: forward primer

<400> SEQUENCE: 38
taataggaag acattttgtg cagcgatttc tgattgacc                  39

<210> SEQ ID NO 39
<211> LENGTH: 38
<212> TYPE: DNA
<213> ORGANISM: Artificial
<220> FEATURE:
<223> OTHER INFORMATION: forward primer

<400> SEQUENCE: 39
aataggaaga cattttgtgc agcgatttct gattgacc                   38

<210> SEQ ID NO 40
<211> LENGTH: 37
<212> TYPE: DNA
<213> ORGANISM: Artificial
<220> FEATURE:
<223> OTHER INFORMATION: forward primer

<400> SEQUENCE: 40
ataggaagac attttgtgca gcgatttctg attgacc                    37

<210> SEQ ID NO 41
<211> LENGTH: 36
<212> TYPE: DNA
<213> ORGANISM: Artificial
<220> FEATURE:
<223> OTHER INFORMATION: forward primer

<400> SEQUENCE: 41
taggaagaca ttttgtgcag cgatttctga ttgacc                     36

<210> SEQ ID NO 42
<211> LENGTH: 35
<212> TYPE: DNA
<213> ORGANISM: Artificial
<220> FEATURE:
<223> OTHER INFORMATION: forward primer
```

<400> SEQUENCE: 42
aggaagacat tttgtgcagc gatttctgat tgacc          35

<210> SEQ ID NO 43
<211> LENGTH: 34
<212> TYPE: DNA
<213> ORGANISM: Artificial
<220> FEATURE:
<223> OTHER INFORMATION: forward primer

<400> SEQUENCE: 43
ggaagacatt tgtgcagcg atttctgatt gacc          34

<210> SEQ ID NO 44
<211> LENGTH: 33
<212> TYPE: DNA
<213> ORGANISM: Artificial
<220> FEATURE:
<223> OTHER INFORMATION: forward primer

<400> SEQUENCE: 44
gaagacattt tgtgcagcga tttctgattg acc          33

<210> SEQ ID NO 45
<211> LENGTH: 32
<212> TYPE: DNA
<213> ORGANISM: Artificial
<220> FEATURE:
<223> OTHER INFORMATION: forward primer

<400> SEQUENCE: 45
aagacatttt gtgcagcgat ttctgattga cc          32

<210> SEQ ID NO 46
<211> LENGTH: 31
<212> TYPE: DNA
<213> ORGANISM: Artificial
<220> FEATURE:
<223> OTHER INFORMATION: forward primer

<400> SEQUENCE: 46
agacattttg tgcagcgatt tctgattgac c          31

<210> SEQ ID NO 47
<211> LENGTH: 30
<212> TYPE: DNA
<213> ORGANISM: Artificial
<220> FEATURE:
<223> OTHER INFORMATION: forward primer

<400> SEQUENCE: 47
gacattttgt gcagcgattt ctgattgacc          30

<210> SEQ ID NO 48
<211> LENGTH: 29
<212> TYPE: DNA
<213> ORGANISM: Artificial
<220> FEATURE:
<223> OTHER INFORMATION: forward primer

<400> SEQUENCE: 48
acattttgtg cagcgatttc tgattgacc          29

<210> SEQ ID NO 49
<211> LENGTH: 28

```
<212> TYPE: DNA
<213> ORGANISM: Artificial
<220> FEATURE:
<223> OTHER INFORMATION: forward primer

<400> SEQUENCE: 49
cattttgtgc agcgatttct gattgacc                                          28

<210> SEQ ID NO 50
<211> LENGTH: 27
<212> TYPE: DNA
<213> ORGANISM: Artificial
<220> FEATURE:
<223> OTHER INFORMATION: forward primer

<400> SEQUENCE: 50
attttgtgca gcgatttctg attgacc                                           27

<210> SEQ ID NO 51
<211> LENGTH: 26
<212> TYPE: DNA
<213> ORGANISM: Artificial
<220> FEATURE:
<223> OTHER INFORMATION: forward primer

<400> SEQUENCE: 51
ttttgtgcag cgatttctga ttgacc                                            26

<210> SEQ ID NO 52
<211> LENGTH: 25
<212> TYPE: DNA
<213> ORGANISM: Artificial
<220> FEATURE:
<223> OTHER INFORMATION: forward primer

<400> SEQUENCE: 52
tttgtgcagc gatttctgat tgacc                                             25

<210> SEQ ID NO 53
<211> LENGTH: 38
<212> TYPE: DNA
<213> ORGANISM: Artificial
<220> FEATURE:
<223> OTHER INFORMATION: reverse primer
<220> FEATURE:
<221> NAME/KEY: misc_feature
<222> LOCATION: (12)..(12)
<223> OTHER INFORMATION: k stands for g or t

<400> SEQUENCE: 53
ccctttatga cktagcaaag gagtggcagc aagttctg                               38

<210> SEQ ID NO 54
<211> LENGTH: 37
<212> TYPE: DNA
<213> ORGANISM: Artificial
<220> FEATURE:
<223> OTHER INFORMATION: reverse primer
<220> FEATURE:
<221> NAME/KEY: misc_feature
<222> LOCATION: (11)..(11)
<223> OTHER INFORMATION: k stands for g or t

<400> SEQUENCE: 54
cctttatgac ktagcaaagg agtggcagca agttctg                                37

<210> SEQ ID NO 55
<211> LENGTH: 36
```

```
<212> TYPE: DNA
<213> ORGANISM: Artificial
<220> FEATURE:
<223> OTHER INFORMATION: reverse primer
<220> FEATURE:
<221> NAME/KEY: misc_feature
<222> LOCATION: (10)..(10)
<223> OTHER INFORMATION: k stands for g or t

<400> SEQUENCE: 55
ctttatgack tagcaaagga gtggcagcaa gttctg                                  36

<210> SEQ ID NO 56
<211> LENGTH: 35
<212> TYPE: DNA
<213> ORGANISM: Artificial
<220> FEATURE:
<223> OTHER INFORMATION: reverse primer
<220> FEATURE:
<221> NAME/KEY: misc_feature
<222> LOCATION: (9)..(9)
<223> OTHER INFORMATION: k stands for g or t

<400> SEQUENCE: 56
tttatgackt agcaaaggag tggcagcaag ttctg                                   35

<210> SEQ ID NO 57
<211> LENGTH: 34
<212> TYPE: DNA
<213> ORGANISM: Artificial
<220> FEATURE:
<223> OTHER INFORMATION: reverse primer
<220> FEATURE:
<221> NAME/KEY: misc_feature
<222> LOCATION: (8)..(8)
<223> OTHER INFORMATION: k stands for g or t

<400> SEQUENCE: 57
ttatgackta gcaaaggagt ggcagcaagt tctg                                    34

<210> SEQ ID NO 58
<211> LENGTH: 33
<212> TYPE: DNA
<213> ORGANISM: Artificial
<220> FEATURE:
<223> OTHER INFORMATION: reverse primer
<220> FEATURE:
<221> NAME/KEY: misc_feature
<222> LOCATION: (7)..(7)
<223> OTHER INFORMATION: k stands for g or t

<400> SEQUENCE: 58
tatgacktag caaaggagtg gcagcaagtt ctg                                     33

<210> SEQ ID NO 59
<211> LENGTH: 32
<212> TYPE: DNA
<213> ORGANISM: Artificial
<220> FEATURE:
<223> OTHER INFORMATION: reverse primer
<220> FEATURE:
<221> NAME/KEY: misc_feature
<222> LOCATION: (6)..(6)
<223> OTHER INFORMATION: k stands for g or t

<400> SEQUENCE: 59
atgacktagc aaaggagtgg cagcaagttc tg                                      32

<210> SEQ ID NO 60
<211> LENGTH: 31
```

```
<212> TYPE: DNA
<213> ORGANISM: Artificial
<220> FEATURE:
<223> OTHER INFORMATION: reverse primer
<220> FEATURE:
<221> NAME/KEY: misc_feature
<222> LOCATION: (5)..(5)
<223> OTHER INFORMATION: k stands for g or t

<400> SEQUENCE: 60
tgacktagca aaggagtggc agcaagttct g                              31

<210> SEQ ID NO 61
<211> LENGTH: 30
<212> TYPE: DNA
<213> ORGANISM: Artificial
<220> FEATURE:
<223> OTHER INFORMATION: reverse primer
<220> FEATURE:
<221> NAME/KEY: misc_feature
<222> LOCATION: (4)..(4)
<223> OTHER INFORMATION: k stands for g or t

<400> SEQUENCE: 61
gacktagcaa aggagtggca gcaagttctg                               30

<210> SEQ ID NO 62
<211> LENGTH: 29
<212> TYPE: DNA
<213> ORGANISM: Artificial
<220> FEATURE:
<223> OTHER INFORMATION: reverse primer
<220> FEATURE:
<221> NAME/KEY: misc_feature
<222> LOCATION: (3)..(3)
<223> OTHER INFORMATION: k stands for g or t

<400> SEQUENCE: 62
acktagcaaa ggagtggcag caagttctg                                29

<210> SEQ ID NO 63
<211> LENGTH: 28
<212> TYPE: DNA
<213> ORGANISM: Artificial
<220> FEATURE:
<223> OTHER INFORMATION: reverse primer
<220> FEATURE:
<221> NAME/KEY: misc_feature
<222> LOCATION: (2)..(2)
<223> OTHER INFORMATION: k stands for g or t

<400> SEQUENCE: 63
cktagcaaag gagtggcagc aagttctg                                 28

<210> SEQ ID NO 64
<211> LENGTH: 27
<212> TYPE: DNA
<213> ORGANISM: Artificial
<220> FEATURE:
<223> OTHER INFORMATION: reverse primer
<220> FEATURE:
<221> NAME/KEY: misc_feature
<222> LOCATION: (1)..(1)
<223> OTHER INFORMATION: k stands for g or t

<400> SEQUENCE: 64
ktagcaaagg agtggcagca agttctg                                  27

<210> SEQ ID NO 65
<211> LENGTH: 26
```

```
<212> TYPE: DNA
<213> ORGANISM: Artificial
<220> FEATURE:
<223> OTHER INFORMATION: reverse primer

<400> SEQUENCE: 65
tagcaaagga gtggcagcaa gttctg                                       26

<210> SEQ ID NO 66
<211> LENGTH: 25
<212> TYPE: DNA
<213> ORGANISM: Artificial
<220> FEATURE:
<223> OTHER INFORMATION: reverse primer

<400> SEQUENCE: 66
agcaaaggag tggcagcaag ttctg                                        25

<210> SEQ ID NO 67
<211> LENGTH: 24
<212> TYPE: DNA
<213> ORGANISM: Artificial
<220> FEATURE:
<223> OTHER INFORMATION: reverse primer

<400> SEQUENCE: 67
gcaaaggagt ggcagcaagt tctg                                         24

<210> SEQ ID NO 68
<211> LENGTH: 23
<212> TYPE: DNA
<213> ORGANISM: Artificial
<220> FEATURE:
<223> OTHER INFORMATION: reverse primer

<400> SEQUENCE: 68
caaaggagtg gcagcaagtt ctg                                          23

<210> SEQ ID NO 69
<211> LENGTH: 26
<212> TYPE: DNA
<213> ORGANISM: Artificial
<220> FEATURE:
<223> OTHER INFORMATION: probe

<400> SEQUENCE: 69
cggcgcatgg cttcyattgg gtgcca                                       26

<210> SEQ ID NO 70
<211> LENGTH: 25
<212> TYPE: DNA
<213> ORGANISM: Artificial
<220> FEATURE:
<223> OTHER INFORMATION: probe

<400> SEQUENCE: 70
ggcgcatggc ttcyattggg tgcca                                        25

<210> SEQ ID NO 71
<211> LENGTH: 24
<212> TYPE: DNA
<213> ORGANISM: Artificial
<220> FEATURE:
<223> OTHER INFORMATION: probe

<400> SEQUENCE: 71
gcgcatggct tcyattgggt gcca                                         24
```

<210> SEQ ID NO 72
<211> LENGTH: 23
<212> TYPE: DNA
<213> ORGANISM: Artificial
<220> FEATURE:
<223> OTHER INFORMATION: probe

<400> SEQUENCE: 72
cgcatggctt cyattgggtg cca                                              23

<210> SEQ ID NO 73
<211> LENGTH: 22
<212> TYPE: DNA
<213> ORGANISM: Artificial
<220> FEATURE:
<223> OTHER INFORMATION: probe

<400> SEQUENCE: 73
gcatggcttc yattgggtgc ca                                               22

<210> SEQ ID NO 74
<211> LENGTH: 21
<212> TYPE: DNA
<213> ORGANISM: Artificial
<220> FEATURE:
<223> OTHER INFORMATION: probe

<400> SEQUENCE: 74
catggcttcy attgggtgcc a                                                21

<210> SEQ ID NO 75
<211> LENGTH: 28
<212> TYPE: DNA
<213> ORGANISM: Artificial
<220> FEATURE:
<223> OTHER INFORMATION: probe

<400> SEQUENCE: 75
ctggtcatcg tggccatcgc ccggactc                                         28

<210> SEQ ID NO 76
<211> LENGTH: 27
<212> TYPE: DNA
<213> ORGANISM: Artificial
<220> FEATURE:
<223> OTHER INFORMATION: probe

<400> SEQUENCE: 76
tggtcatcgt ggccatcgcc cggactc                                          27

<210> SEQ ID NO 77
<211> LENGTH: 26
<212> TYPE: DNA
<213> ORGANISM: Artificial
<220> FEATURE:
<223> OTHER INFORMATION: probe

<400> SEQUENCE: 77
ggtcatcgtg gccatcgccc ggactc                                           26

<210> SEQ ID NO 78
<211> LENGTH: 25
<212> TYPE: DNA
<213> ORGANISM: Artificial
<220> FEATURE:
<223> OTHER INFORMATION: probe

<400> SEQUENCE: 78
gtcatcgtgg ccatcgcccg gactc                                              25

<210> SEQ ID NO 79
<211> LENGTH: 24
<212> TYPE: DNA
<213> ORGANISM: Artificial
<220> FEATURE:
<223> OTHER INFORMATION: probe

<400> SEQUENCE: 79
tcatcgtggc catcgcccgg actc                                               24

<210> SEQ ID NO 80
<211> LENGTH: 23
<212> TYPE: DNA
<213> ORGANISM: Artificial
<220> FEATURE:
<223> OTHER INFORMATION: probe

<400> SEQUENCE: 80
catcgtggcc atcgcccgga ctc                                                23

<210> SEQ ID NO 81
<211> LENGTH: 22
<212> TYPE: DNA
<213> ORGANISM: Artificial
<220> FEATURE:
<223> OTHER INFORMATION: probe

<400> SEQUENCE: 81
atcgtggcca tcgcccggac tc                                                 22

<210> SEQ ID NO 82
<211> LENGTH: 21
<212> TYPE: DNA
<213> ORGANISM: Artificial
<220> FEATURE:
<223> OTHER INFORMATION: probe

<400> SEQUENCE: 82
tcgtggccat cgcccggact c                                                  21

<210> SEQ ID NO 83
<211> LENGTH: 20
<212> TYPE: DNA
<213> ORGANISM: Artificial
<220> FEATURE:
<223> OTHER INFORMATION: probe

<400> SEQUENCE: 83
cgtggccatc gcccggactc                                                    20

<210> SEQ ID NO 84
<211> LENGTH: 19
<212> TYPE: DNA
<213> ORGANISM: Artificial
<220> FEATURE:
<223> OTHER INFORMATION: probe

<400> SEQUENCE: 84
gtggccatcg cccggactc                                                     19

<210> SEQ ID NO 85
<211> LENGTH: 18

```
<212> TYPE: DNA
<213> ORGANISM: Artificial
<220> FEATURE:
<223> OTHER INFORMATION: probe

<400> SEQUENCE: 85
tggccatcgc ccggactc                                               18

<210> SEQ ID NO 86
<211> LENGTH: 17
<212> TYPE: DNA
<213> ORGANISM: Artificial
<220> FEATURE:
<223> OTHER INFORMATION: probe

<400> SEQUENCE: 86
ggccatcgcc cggactc                                                17

<210> SEQ ID NO 87
<211> LENGTH: 31
<212> TYPE: DNA
<213> ORGANISM: Artificial
<220> FEATURE:
<223> OTHER INFORMATION: probe

<400> SEQUENCE: 87
cacagtttga tcgagtgcat ttgttaatgt g                                31

<210> SEQ ID NO 88
<211> LENGTH: 30
<212> TYPE: DNA
<213> ORGANISM: Artificial
<220> FEATURE:
<223> OTHER INFORMATION: probe

<400> SEQUENCE: 88
cacagtttga tcgagtgcat ttgttaatgt                                  30

<210> SEQ ID NO 89
<211> LENGTH: 29
<212> TYPE: DNA
<213> ORGANISM: Artificial
<220> FEATURE:
<223> OTHER INFORMATION: probe

<400> SEQUENCE: 89
cacagtttga tcgagtgcat ttgttaatg                                   29

<210> SEQ ID NO 90
<211> LENGTH: 28
<212> TYPE: DNA
<213> ORGANISM: Artificial
<220> FEATURE:
<223> OTHER INFORMATION: probe

<400> SEQUENCE: 90
cacagtttga tcgagtgcat ttgttaat                                    28

<210> SEQ ID NO 91
<211> LENGTH: 27
<212> TYPE: DNA
<213> ORGANISM: Artificial
<220> FEATURE:
<223> OTHER INFORMATION: probe

<400> SEQUENCE: 91
cacagtttga tcgagtgcat ttgttaa                                     27
```

<210> SEQ ID NO 92
<211> LENGTH: 26
<212> TYPE: DNA
<213> ORGANISM: Artificial
<220> FEATURE:
<223> OTHER INFORMATION: probe

<400> SEQUENCE: 92
cacagtttga tcgagtgcat ttgtta                                    26

<210> SEQ ID NO 93
<211> LENGTH: 25
<212> TYPE: DNA
<213> ORGANISM: Artificial
<220> FEATURE:
<223> OTHER INFORMATION: probe

<400> SEQUENCE: 93
cacagtttga tcgagtgcat ttgtt                                     25

<210> SEQ ID NO 94
<211> LENGTH: 24
<212> TYPE: DNA
<213> ORGANISM: Artificial
<220> FEATURE:
<223> OTHER INFORMATION: probe

<400> SEQUENCE: 94
cacagtttga tcgagtgcat ttgt                                      24

<210> SEQ ID NO 95
<211> LENGTH: 23
<212> TYPE: DNA
<213> ORGANISM: Artificial
<220> FEATURE:
<223> OTHER INFORMATION: probe

<400> SEQUENCE: 95
cacagtttga tcgagtgcat ttg                                       23

<210> SEQ ID NO 96
<211> LENGTH: 22
<212> TYPE: DNA
<213> ORGANISM: Artificial
<220> FEATURE:
<223> OTHER INFORMATION: probe

<400> SEQUENCE: 96
cacagtttga tcgagtgcat tt                                        22

<210> SEQ ID NO 97
<211> LENGTH: 21
<212> TYPE: DNA
<213> ORGANISM: Artificial
<220> FEATURE:
<223> OTHER INFORMATION: probe

<400> SEQUENCE: 97
cacagtttga tcgagtgcat t                                         21

<210> SEQ ID NO 98
<211> LENGTH: 20
<212> TYPE: DNA
<213> ORGANISM: Artificial
<220> FEATURE:
<223> OTHER INFORMATION: probe

```
<400> SEQUENCE: 98
cacagtttga tcgagtgcat                                              20

<210> SEQ ID NO 99
<211> LENGTH: 19
<212> TYPE: DNA
<213> ORGANISM: Artificial
<220> FEATURE:
<223> OTHER INFORMATION: probe

<400> SEQUENCE: 99
cacagtttga tcgagtgca                                               19

<210> SEQ ID NO 100
<211> LENGTH: 18
<212> TYPE: DNA
<213> ORGANISM: Artificial
<220> FEATURE:
<223> OTHER INFORMATION: probe

<400> SEQUENCE: 100
cacagtttga tcgagtgc                                                18

<210> SEQ ID NO 101
<211> LENGTH: 23
<212> TYPE: DNA
<213> ORGANISM: Artificial
<220> FEATURE:
<223> OTHER INFORMATION: probe

<400> SEQUENCE: 101
cgcatggctt ccattgggtg cca                                          23

<210> SEQ ID NO 102
<211> LENGTH: 23
<212> TYPE: DNA
<213> ORGANISM: Artificial
<220> FEATURE:
<223> OTHER INFORMATION: probe

<400> SEQUENCE: 102
cgcatggctt ctattgggtg cca                                          23

<210> SEQ ID NO 103
<211> LENGTH: 26
<212> TYPE: DNA
<213> ORGANISM: Artificial
<220> FEATURE:
<223> OTHER INFORMATION: forward primer

<400> SEQUENCE: 103
gcaacccggg aacggcagcg ccttct                                       26

<210> SEQ ID NO 104
<211> LENGTH: 25
<212> TYPE: DNA
<213> ORGANISM: Artificial
<220> FEATURE:
<223> OTHER INFORMATION: forward primer

<400> SEQUENCE: 104
caacccggga acggcagcgc cttct                                        25

<210> SEQ ID NO 105
<211> LENGTH: 24
```

```
<212> TYPE: DNA
<213> ORGANISM: Artificial
<220> FEATURE:
<223> OTHER INFORMATION: forward primer

<400> SEQUENCE: 105
aacccgggaa cggcagcgcc ttct                                              24

<210> SEQ ID NO 106
<211> LENGTH: 23
<212> TYPE: DNA
<213> ORGANISM: Artificial
<220> FEATURE:
<223> OTHER INFORMATION: forward primer

<400> SEQUENCE: 106
acccgggaac ggcagcgcct tct                                               23

<210> SEQ ID NO 107
<211> LENGTH: 22
<212> TYPE: DNA
<213> ORGANISM: Artificial
<220> FEATURE:
<223> OTHER INFORMATION: forward primer

<400> SEQUENCE: 107
cccgggaacg gcagcgcctt ct                                                22

<210> SEQ ID NO 108
<211> LENGTH: 21
<212> TYPE: DNA
<213> ORGANISM: Artificial
<220> FEATURE:
<223> OTHER INFORMATION: forward primer

<400> SEQUENCE: 108
ccgggaacgg cagcgccttc t                                                 21

<210> SEQ ID NO 109
<211> LENGTH: 20
<212> TYPE: DNA
<213> ORGANISM: Artificial
<220> FEATURE:
<223> OTHER INFORMATION: forward primer

<400> SEQUENCE: 109
cgggaacggc agcgccttct                                                   20

<210> SEQ ID NO 110
<211> LENGTH: 19
<212> TYPE: DNA
<213> ORGANISM: Artificial
<220> FEATURE:
<223> OTHER INFORMATION: forward primer

<400> SEQUENCE: 110
gggaacggca gcgccttct                                                    19

<210> SEQ ID NO 111
<211> LENGTH: 18
<212> TYPE: DNA
<213> ORGANISM: Artificial
<220> FEATURE:
<223> OTHER INFORMATION: forward primer

<400> SEQUENCE: 111
ggaacggcag cgccttct                                                     18
```

<210> SEQ ID NO 112
<211> LENGTH: 19
<212> TYPE: DNA
<213> ORGANISM: Artificial
<220> FEATURE:
<223> OTHER INFORMATION: probe

<400> SEQUENCE: 112
cccaatrgaa gccatgcgc                                                19

<210> SEQ ID NO 113
<211> LENGTH: 18
<212> TYPE: DNA
<213> ORGANISM: Artificial
<220> FEATURE:
<223> OTHER INFORMATION: probe

<400> SEQUENCE: 113
cccaatrgaa gccatgcg                                                 18

<210> SEQ ID NO 114
<211> LENGTH: 17
<212> TYPE: DNA
<213> ORGANISM: Artificial
<220> FEATURE:
<223> OTHER INFORMATION: probe

<400> SEQUENCE: 114
cccaatrgaa gccatgc                                                  17

<210> SEQ ID NO 115
<211> LENGTH: 16
<212> TYPE: DNA
<213> ORGANISM: Artificial
<220> FEATURE:
<223> OTHER INFORMATION: probe

<400> SEQUENCE: 115
cccaatrgaa gccatg                                                   16

<210> SEQ ID NO 116
<211> LENGTH: 15
<212> TYPE: DNA
<213> ORGANISM: Artificial
<220> FEATURE:
<223> OTHER INFORMATION: probe

<400> SEQUENCE: 116
cccaatrgaa gccat                                                    15

<210> SEQ ID NO 117
<211> LENGTH: 17
<212> TYPE: DNA
<213> ORGANISM: Artificial
<220> FEATURE:
<223> OTHER INFORMATION: probe

<400> SEQUENCE: 117
ctcggagtcc gggcgat                                                  17

<210> SEQ ID NO 118
<211> LENGTH: 16
<212> TYPE: DNA
<213> ORGANISM: Artificial
<220> FEATURE:
<223> OTHER INFORMATION: probe

<400> SEQUENCE: 118
ctcggagtcc gggcga                                                          16

<210> SEQ ID NO 119
<211> LENGTH: 15
<212> TYPE: DNA
<213> ORGANISM: Artificial
<220> FEATURE:
<223> OTHER INFORMATION: probe

<400> SEQUENCE: 119
ctcggagtcc gggcg                                                           15

<210> SEQ ID NO 120
<211> LENGTH: 14
<212> TYPE: DNA
<213> ORGANISM: Artificial
<220> FEATURE:
<223> OTHER INFORMATION: probe

<400> SEQUENCE: 120
ctcggagtcc gggc                                                            14

<210> SEQ ID NO 121
<211> LENGTH: 13
<212> TYPE: DNA
<213> ORGANISM: Artificial
<220> FEATURE:
<223> OTHER INFORMATION: probe

<400> SEQUENCE: 121
ctcggagtcc ggg                                                             13

<210> SEQ ID NO 122
<211> LENGTH: 12
<212> TYPE: DNA
<213> ORGANISM: Artificial
<220> FEATURE:
<223> OTHER INFORMATION: probe

<400> SEQUENCE: 122
ctcggagtcc gg                                                              12

<210> SEQ ID NO 123
<211> LENGTH: 17
<212> TYPE: DNA
<213> ORGANISM: Artificial
<220> FEATURE:
<223> OTHER INFORMATION: probe

<400> SEQUENCE: 123
ctcggagtcc aggcgat                                                         17

<210> SEQ ID NO 124
<211> LENGTH: 16
<212> TYPE: DNA
<213> ORGANISM: Artificial
<220> FEATURE:
<223> OTHER INFORMATION: probe

<400> SEQUENCE: 124
ctcggagtcc aggcga                                                          16

<210> SEQ ID NO 125
<211> LENGTH: 15

```
<212> TYPE: DNA
<213> ORGANISM: Artificial
<220> FEATURE:
<223> OTHER INFORMATION: probe

<400> SEQUENCE: 125
ctcggagtcc aggcg                                                      15

<210> SEQ ID NO 126
<211> LENGTH: 14
<212> TYPE: DNA
<213> ORGANISM: Artificial
<220> FEATURE:
<223> OTHER INFORMATION: probe

<400> SEQUENCE: 126
ctcggagtcc aggc                                                       14

<210> SEQ ID NO 127
<211> LENGTH: 13
<212> TYPE: DNA
<213> ORGANISM: Artificial
<220> FEATURE:
<223> OTHER INFORMATION: probe

<400> SEQUENCE: 127
ctcggagtcc agg                                                        13

<210> SEQ ID NO 128
<211> LENGTH: 12
<212> TYPE: DNA
<213> ORGANISM: Artificial
<220> FEATURE:
<223> OTHER INFORMATION: probe

<400> SEQUENCE: 128
ctcggagtcc ag                                                         12

<210> SEQ ID NO 129
<211> LENGTH: 27
<212> TYPE: DNA
<213> ORGANISM: Artificial
<220> FEATURE:
<223> OTHER INFORMATION: primer

<400> SEQUENCE: 129
catgcccacc acccacacct cgtccct                                         27

<210> SEQ ID NO 130
<211> LENGTH: 26
<212> TYPE: DNA
<213> ORGANISM: Artificial
<220> FEATURE:
<223> OTHER INFORMATION: primer

<400> SEQUENCE: 130
atgcccacca cccacacctc gtccct                                          26

<210> SEQ ID NO 131
<211> LENGTH: 25
<212> TYPE: DNA
<213> ORGANISM: Artificial
<220> FEATURE:
<223> OTHER INFORMATION: primer

<400> SEQUENCE: 131
tgcccaccac ccacacctcg tccct                                           25
```

<210> SEQ ID NO 132
<211> LENGTH: 24
<212> TYPE: DNA
<213> ORGANISM: Artificial
<220> FEATURE:
<223> OTHER INFORMATION: primer

<400> SEQUENCE: 132
gcccaccacc cacacctcgt ccct                                    24

<210> SEQ ID NO 133
<211> LENGTH: 23
<212> TYPE: DNA
<213> ORGANISM: Artificial
<220> FEATURE:
<223> OTHER INFORMATION: primer

<400> SEQUENCE: 133
cccaccaccc acacctcgtc cct                                     23

<210> SEQ ID NO 134
<211> LENGTH: 22
<212> TYPE: DNA
<213> ORGANISM: Artificial
<220> FEATURE:
<223> OTHER INFORMATION: primer

<400> SEQUENCE: 134
ccaccaccca cacctcgtcc ct                                      22

<210> SEQ ID NO 135
<211> LENGTH: 21
<212> TYPE: DNA
<213> ORGANISM: Artificial
<220> FEATURE:
<223> OTHER INFORMATION: primer

<400> SEQUENCE: 135
caccacccac acctcgtccc t                                       21

<210> SEQ ID NO 136
<211> LENGTH: 20
<212> TYPE: DNA
<213> ORGANISM: Artificial
<220> FEATURE:
<223> OTHER INFORMATION: primer

<400> SEQUENCE: 136
accacccaca cctcgtccct                                         20

<210> SEQ ID NO 137
<211> LENGTH: 19
<212> TYPE: DNA
<213> ORGANISM: Artificial
<220> FEATURE:
<223> OTHER INFORMATION: primer

<400> SEQUENCE: 137
ccacccacac ctcgtccct                                          19

<210> SEQ ID NO 138
<211> LENGTH: 18
<212> TYPE: DNA
<213> ORGANISM: Artificial
<220> FEATURE:
<223> OTHER INFORMATION: primer

```
<400> SEQUENCE: 138
cacccacacc tcgtccct                                              18

<210> SEQ ID NO 139
<211> LENGTH: 17
<212> TYPE: DNA
<213> ORGANISM: Artificial
<220> FEATURE:
<223> OTHER INFORMATION: probe

<400> SEQUENCE: 139
cacagtttga tcgagtg                                               17

<210> SEQ ID NO 140
<211> LENGTH: 15
<212> TYPE: DNA
<213> ORGANISM: Artificial
<220> FEATURE:
<223> OTHER INFORMATION: probe

<400> SEQUENCE: 140
cacccaatgg aagcc                                                 15

<210> SEQ ID NO 141
<211> LENGTH: 16
<212> TYPE: DNA
<213> ORGANISM: Artificial
<220> FEATURE:
<223> OTHER INFORMATION: probe

<400> SEQUENCE: 141
ccaatggaag ccatgc                                                16

<210> SEQ ID NO 142
<211> LENGTH: 20
<212> TYPE: DNA
<213> ORGANISM: Artificial
<220> FEATURE:
<223> OTHER INFORMATION: probe

<400> SEQUENCE: 142
catggcttcc attgggtgcc                                            20

<210> SEQ ID NO 143
<211> LENGTH: 18
<212> TYPE: DNA
<213> ORGANISM: Artificial
<220> FEATURE:
<223> OTHER INFORMATION: probe

<400> SEQUENCE: 143
catggcttcc attgggtg                                              18

<210> SEQ ID NO 144
<211> LENGTH: 17
<212> TYPE: DNA
<213> ORGANISM: Artificial
<220> FEATURE:
<223> OTHER INFORMATION: probe

<400> SEQUENCE: 144
ggcttccatt gggtgcc                                               17

<210> SEQ ID NO 145
<211> LENGTH: 17
```

```
<212> TYPE: DNA
<213> ORGANISM: Artificial
<220> FEATURE:
<223> OTHER INFORMATION: probe

<400> SEQUENCE: 145
ggcacccaat agaagcc                                                  17

<210> SEQ ID NO 146
<211> LENGTH: 20
<212> TYPE: DNA
<213> ORGANISM: Artificial
<220> FEATURE:
<223> OTHER INFORMATION: probe

<400> SEQUENCE: 146
ccggcgcatg gcttccattg                                               20

<210> SEQ ID NO 147
<211> LENGTH: 15
<212> TYPE: DNA
<213> ORGANISM: Artificial
<220> FEATURE:
<223> OTHER INFORMATION: probe

<400> SEQUENCE: 147
tagaagccat gcgcc                                                    15

<210> SEQ ID NO 148
<211> LENGTH: 17
<212> TYPE: DNA
<213> ORGANISM: Artificial
<220> FEATURE:
<223> OTHER INFORMATION: probe

<400> SEQUENCE: 148
ccaatagaag ccatgcg                                                  17

<210> SEQ ID NO 149
<211> LENGTH: 15
<212> TYPE: DNA
<213> ORGANISM: Artificial
<220> FEATURE:
<223> OTHER INFORMATION: probe

<400> SEQUENCE: 149
ccaatggaag ccatg                                                    15

<210> SEQ ID NO 150
<211> LENGTH: 15
<212> TYPE: DNA
<213> ORGANISM: Artificial
<220> FEATURE:
<223> OTHER INFORMATION: probe

<400> SEQUENCE: 150
tggaagccat gcgcc                                                    15

<210> SEQ ID NO 151
<211> LENGTH: 15
<212> TYPE: DNA
<213> ORGANISM: Artificial
<220> FEATURE:
<223> OTHER INFORMATION: probe

<400> SEQUENCE: 151
caatggaagc catgc                                                    15
```

<210> SEQ ID NO 152
<211> LENGTH: 17
<212> TYPE: DNA
<213> ORGANISM: Artificial
<220> FEATURE:
<223> OTHER INFORMATION: probe

<400> SEQUENCE: 152
cttccattgg gtgccag                                                    17

<210> SEQ ID NO 153
<211> LENGTH: 16
<212> TYPE: DNA
<213> ORGANISM: Artificial
<220> FEATURE:
<223> OTHER INFORMATION: probe

<400> SEQUENCE: 153
ccattgggtg ccagca                                                     16

<210> SEQ ID NO 154
<211> LENGTH: 22
<212> TYPE: DNA
<213> ORGANISM: Artificial
<220> FEATURE:
<223> OTHER INFORMATION: probe

<400> SEQUENCE: 154
cttccattgg gtgccagcaa ga                                              22

<210> SEQ ID NO 155
<211> LENGTH: 20
<212> TYPE: DNA
<213> ORGANISM: Artificial
<220> FEATURE:
<223> OTHER INFORMATION: probe

<400> SEQUENCE: 155
gctggcaccc aatggaagcc                                                 20

<210> SEQ ID NO 156
<211> LENGTH: 18
<212> TYPE: DNA
<213> ORGANISM: Artificial
<220> FEATURE:
<223> OTHER INFORMATION: probe

<400> SEQUENCE: 156
ccaatggaag ccatgcgc                                                   18

<210> SEQ ID NO 157
<211> LENGTH: 20
<212> TYPE: DNA
<213> ORGANISM: Artificial
<220> FEATURE:
<223> OTHER INFORMATION: probe

<400> SEQUENCE: 157
ccaatggaag ccatgcgccg                                                 20

<210> SEQ ID NO 158
<211> LENGTH: 19
<212> TYPE: DNA
<213> ORGANISM: Artificial
<220> FEATURE:
<223> OTHER INFORMATION: probe

<400> SEQUENCE: 158
ccaatggaag ccatgcgcc                                                                    19

<210> SEQ ID NO 159
<211> LENGTH: 18
<212> TYPE: DNA
<213> ORGANISM: Artificial
<220> FEATURE:
<223> OTHER INFORMATION: probe

<400> SEQUENCE: 159
ggcttccatt gggtgcca                                                                     18

<210> SEQ ID NO 160
<211> LENGTH: 22
<212> TYPE: DNA
<213> ORGANISM: Artificial
<220> FEATURE:
<223> OTHER INFORMATION: probe

<400> SEQUENCE: 160
catggcttcc attgggtgcc ag                                                                22

<210> SEQ ID NO 161
<211> LENGTH: 40
<212> TYPE: DNA
<213> ORGANISM: Artificial
<220> FEATURE:
<223> OTHER INFORMATION: DNA

<400> SEQUENCE: 161
cgccttcttg ctggcaccca atagaagcca tgcgccggac                                             40

<210> SEQ ID NO 162
<211> LENGTH: 40
<212> TYPE: DNA
<213> ORGANISM: Artificial
<220> FEATURE:
<223> OTHER INFORMATION: DNA

<400> SEQUENCE: 162
cgccttcttg ctggcaccca atggaagcca tgcgccggac                                             40

<210> SEQ ID NO 163
<211> LENGTH: 40
<212> TYPE: DNA
<213> ORGANISM: Artificial
<220> FEATURE:
<223> OTHER INFORMATION: DNA

<400> SEQUENCE: 163
gtccggcgca tggcttctat tgggtgccag caagaaggcg                                             40

<210> SEQ ID NO 164
<211> LENGTH: 40
<212> TYPE: DNA
<213> ORGANISM: Artificial
<220> FEATURE:
<223> OTHER INFORMATION: DNA

<400> SEQUENCE: 164
gtccggcgca tggcttccat tgggtgccag caagaaggcg                                             40

<210> SEQ ID NO 165
<211> LENGTH: 23

```
<212> TYPE: DNA
<213> ORGANISM: Artificial
<220> FEATURE:
<223> OTHER INFORMATION: primer

<400> SEQUENCE: 165
gggaacggca gcgccttctt gct                                           23

<210> SEQ ID NO 166
<211> LENGTH: 26
<212> TYPE: DNA
<213> ORGANISM: Artificial
<220> FEATURE:
<223> OTHER INFORMATION: primer

<400> SEQUENCE: 166
tggtgaccgt ctgcagacgc tcgaac                                        26
```

PROBES FOR DETECTING OBESITY GENE

TECHNICAL FIELD

The present invention relates to primer sets for amplifying the β2AR gene, the β3AR gene, and the UCP1 gene, which are the obesity gene, reagents for amplifying the obesity gene containing the same, and the uses thereof.

BACKGROUND ART

As polymorphisms of genes involving obesity, polymorphisms of the gene coding for β-2 adrenaline receptor (β2AR) (β2AR gene), the gene coding for β-3 adrenaline receptor (β3AR) (β3AR gene), and the gene coding for uncoupling protein (UCP) (UCP1 gene) are known. β2AR is mainly distributed in the heart and the bronchial smooth muscle. Besides them, β2AR is present in fat tissue and is involved in lipolysis. Further, the β2AR gene coding for β2AR includes a polymorphism (Arg16Gly) in which arginine (Arg) at position 16 of amino acid is changed to glycine (Gly). It has been reported that, as compared to subjects not having the aforementioned polymorphism, a resting metabolism amount of subjects having this polymorphism (16% in Japanese) is increased. Further, β3AR is present in brown adipose tissue and white adipose tissue. Upon binding of noradrenaline, thermogenesis in the brown adipose tissue and lipolysis in the white adipose tissue are started, respectively. The β3AR gene coding for β3AR includes a polymorphism (Trp61Arg) in which tryptophan (Trp) at position 64 of amino acid is changed to arginine (Arg). It has been reported that, as compared to subjects not having the aforementioned polymorphism, a resting metabolism amount of subjects having this polymorphism (34% in Japanese) is decreased. Further, UCP1 is a protein that plays a main role in the thermogenesis in the brown adipose tissue when sympathetic nerve is in an excited state. The UCP1 gene coding for UCP1 includes a polymorphism in which adenine CA) at position −3826 in mRNA (position 3826 at upstream of a translation initiation site of the UCP1 gene in the genome sequence) is changed to guanine (G). It has been reported that, as compared to subjects not having the aforementioned polymorphism, a total body metabolism amount of subjects having this polymorphism (24% in overweight Japanese female) is decreased. On the bases of the relationship between polymorphisms of the aforementioned respective genes and metabolism amounts, the polymorphisms of these genes are analyzed. Analysis results thereof are practically used for treatment and prevention of obesity of the subjects.

On the other hand, detection of a point mutation, a so-called single nucleotide polymorphism (SNP), is employed widely as an analysis method, at the gene level, for example, the causes of all types of diseases and the individual differences in disease liability (susceptibility to diseases) and in drug action. Examples of the common methods of detecting a point mutation include: (1) a direct sequencing method in which the region corresponding to a sequence to be detected in a target DNA of a sample is amplified by a polymerase chain reaction (PCR) and all the gene sequences are analyzed, (2) a RFLP analysis in which the region corresponding to a sequence to be detected in a target DNA of a sample is amplified by PCR, the amplification product thus obtained is cut with a restriction enzyme whose cleaving action differs depending on the presence or absence of the target mutation in the sequence to be detected and is then electrophoresed, and thereby typing is performed, and (3) the ASP-PCR method in which PCR is performed using a primer with a target mutation located at the 3'-end region and the mutation is judged depending on the presence or absence of amplification.

However, since these methods require, for example, purification of DNA extracted from a sample, electrophoresis, and a treatment with a restriction enzyme, they take time and cost. Furthermore, after PCR is performed, it is necessary to open the reaction container once. Accordingly, there is a possibility that the amplification product may contaminate the next reaction system and thereby the analysis accuracy may be deteriorated. Moreover, since it is difficult to automate, multiple samples cannot be analyzed. Further, the aforementioned ASP-PCR method (3) is less specific, which also is a problem.

Because of these problems, recently, a method of analyzing the melting temperature (Tm) of double-stranded nucleic acid formed of a probe and target nucleic acid is used as a method of detecting a point mutation. Since such a method is performed through, for example, Tm analysis or analysis of the melting curve of the double strand, it is referred to as melting curve analysis. This method is described below. That is, first, a probe complementary to a sequence to be detected containing a target point mutation is used to form a hybrid (double-stranded DNA) between the aforementioned probe and a target single-stranded DNA contained in a detection sample. Subsequently, this hybridization product is heat-treated, and dissociation (melting) of the hybrid accompanying the temperature rise is detected by a change in a signal such as absorbance. The Tm value is then determined based on the result of the detection and the presence or absence of any point mutation is judged accordingly. The higher the homology of the hybridization product, the higher the Tm value, and the lower the homology, the lower the Tm value. Therefore the Tm value (reference value for assessment) is determined beforehand with respect to the hybridization product between the sequence to be detected containing a point mutation and a probe complementary thereto, and then the Tm value (measured value) of the hybridization product between the target single-stranded DNA contained in the detection sample and the aforementioned probe is measured. When the measured value is comparable to the reference value, it is considered as matching, that is, it can be judged that a point mutation is present in the target DNA. On the other hand, when the measured value is lower than the reference value, it is considered as mismatching, that is, it can be judged that no point mutation is present in the target DNA. Furthermore, according to this method, it also is possible to automate the gene analysis.

However, such a detection method using Tm analysis also has a problem in that a region including a site to be detected must be able to be amplified specifically and efficiently in PCR. Particularly, many isozymes are present in the β2AR gene, the β3AR gene, and the UCP1 gene, which are important genes among the obesity genes, and the sequences for coding them also are very similar to one another. Accordingly, there is a possibility that genes coding for isozymes other than those desired genes also are amplified in PCR. Furthermore, when other isozyme-coding genes also have been amplified as described above, for example, in analysis in each polymorphism of the β2AR gene, the β3AR gene, and the UCP1 gene (Nonpatent Documents 1-3), it may cause a decrease in reliability of the analysis result. Moreover, as described above, since analysis of one sample is accompanied by a considerable amount of time and energy, it is not practical to analyze multiple samples, which also is a problem.

[Nonpatent Document 1] PMID: 9399966 J Clin Invest. Dec. 15, 1997; 100(12): 3184-8.
[Nonpatent Document 2] PMID: 9049481 Diabetologia. February 1997; 40(2): 200-4.
[Nonpatent Document 3] PMID: 9541178 Diabetologia. March 1998; 41(3): 357-61.

DISCLOSURE OF INVENTION

Hence, the present invention is intended to provide primer sets for specifically amplifying a target region in at least one obesity gene selected from the group consisting of the β2AR gene, the β3AR gene, and the UCP1 gene by a gene amplification method.

In order to achieve the aforementioned object, a primer set of the present invention is a primer set for amplifying the obesity gene by a gene amplification method, wherein the obesity gene is at least one selected from the group consisting of the β2AR gene, the β3AR gene, and the UCP1 gene, and wherein the primer set includes at least one selected from the group consisting of the following primer sets (1) to (3):

Primer Set (1):
a primer set of a pair of primers including a forward primer composed of the following oligonucleotide (F1) and a reverse primer composed of the following oligonucleotide (R1):
(F1): at least one oligonucleotide selected from:
at least one oligonucleotide having a sequence identical to that of a region extending from thymine (T) at base 4248 to be considered as the first base to any one of the $18^{th}$ to $25^{th}$ bases in the direction toward the 5' end in the base sequence of SEQ ID NO: 1, with the thymine (T) being the 3' end, and
at least one oligonucleotide having a sequence identical to that of a region extending from thymine (T) at base 4250 to be considered as the first base to any one of the $18^{th}$ to $26^{th}$ bases in the direction toward the 5' end in the base sequence of SEQ ID NO: 1, with the thymine (T) being the 3' end, and
(R1): at least one oligonucleotide selected from:
at least one oligonucleotide complementary to a region extending from adenine (A) at base 4292 to be considered as the first base to any one of the $21^{st}$ to $31^{st}$ bases in the direction toward the 3' end in the base sequence of SEQ ID NO: 1, with thymine (T) complementary to the adenine (A) at base 4292 being the 3' end, and
at least one oligonucleotide complementary to a region extending from adenine (A) at base 4301 to be considered as the first base to any one of the $18^{th}$ to $27^{th}$ bases in the direction toward the 3' end in the base sequence of SEQ ID NO: 1, with thymine (T) complementary to the adenine (A) at base 4301 being the 3' end, and Primer Set (2):
a primer set of a pair of primers including a forward primer composed of the following oligonucleotide (F2) and a reverse primer composed of the following oligonucleotide (R2):
(F2): at least one oligonucleotide having a sequence identical to that of a region extending from cytosine (C) at base 4110 to be considered as the first base to any one of the $16^{th}$ to $20^{th}$ bases in the direction toward the 5' end in the base sequence of SEQ ID NO: 2, with the cytosine (C) being the 3' end, and
(R2): at least one oligonucleotide complementary to a region extending from guanine (G) at base 4172 to be considered as the first base to any one of the $15^{th}$ to $19^{th}$ bases in the direction toward the 3' end in the base sequence of SEQ ID NO: 2, with cytosine (C) complementary to the guanine (G) at base 4172 being the 3' end, and Primer Set (3):
a primer set of a pair of primers including a forward primer composed of the following oligonucleotide (F3) and a reverse primer composed of the following oligonucleotide (R3):
(F3): at least one oligonucleotide having a sequence identical to that of a region extending from cytosine (C) at base 280 to be considered as the first base to any one of the $25^{th}$ to $44^{th}$ bases in the direction toward the 5' end in the base sequence of SEQ ID NO: 3, with the cytosine (C) being the 3' end, and
(R3): at least one oligonucleotide complementary to a region extending from cytosine (C) at base 350 to be considered as the first base to any one of the $23^{rd}$ to $38^{th}$ bases in the direction toward the 3' end in the base sequence of SEQ ID NO: 3, with guanine (G) complementary to the cytosine (C) at base 350 being the 3' end.

A reagent for amplifying a gene of the present invention is a reagent for amplifying the obesity gene by a gene amplification method, wherein the obesity gene is at least one selected from the group consisting of the β2AR gene, the β3AR gene, and the UCP1 gene, and wherein the reagent includes the primer set for amplifying the obesity gene of the present invention.

A method of manufacturing an amplification product of the present invention is a method of manufacturing an amplification product of the obesity gene by a gene amplification method, wherein the obesity gene is at least one selected from the group consisting of the β2AR gene, the β3AR gene, and the UCP1 gene, and wherein the method includes the following step (I):
(I) amplifying at least one gene selected from the group consisting of the β2AR gene, the β3AR gene, and the UCP1 gene in a reaction solution using a primer set for amplifying the obesity gene according to the present invention, with nucleic acid contained in a sample being used as a template.

A polymorphism analysis method of the present invention is a method of analyzing a polymorphism of a site to be detected in the obesity gene, wherein the obesity gene is at least one selected from the group consisting of the β2AR gene, the β3AR gene, and the UCP1 gene, and wherein the method includes the following steps (i) to (iv):
(i) amplifying a region including a site to be detected in at least one gene selected from the group consisting of the β2AR gene, the β3AR gene, and the UCP1 gene in a reaction solution by a method of manufacturing an amplification product of the present invention,
(ii) preparing a reaction solution that contains the amplification product obtained in step (i) and a probe capable of hybridizing to the site to be detected in at least one gene selected from the group consisting of the β2AR gene, the β3AR gene, and the UCP1 gene,
(iii) measuring signal values that indicate melting states of a hybridization product between the amplification product and the probe while changing the temperature of the reaction solution, and
(iv) determining a polymorphism of the site to be detected in at least one gene selected from the group consisting of the β2AR gene, the β3AR gene, and the UCP1 gene from a change in the signal values accompanying a change in the temperature.

The primer set of the present invention makes it possible to specifically and efficiently amplify a target region in a reaction solution, with the target region including the site where a polymorphism to be detected in at least one obesity gene selected from the group consisting of the β2AR gene, the β3AR gene, and the UCP1 gene is generated. Accordingly, the time and cost can be reduced, which is different from the conventional methods described above. Furthermore, as described above, since a region including a site to be detected where specific polymorphism in the obesity gene is generated can be amplified specifically, for example, further the use of a probe complementary to a sequence to be detected including the site to be detected makes it possible to perform Tm analysis by directly using the aforementioned reaction solution to type the polymorphism. Moreover, since amplification of the target region and typing of the polymorphism can be performed with one reaction solution, it is also possible to automate the operation. Since the use of the primer set of the present invention allows a pretreatment to be omitted even in the case of, for example, a contaminated sample (for instance, whole blood or oral mucosa), the amplification reaction can be carried out quicker and more simply. Furthermore, since the use of the primer set of the present invention allows the amplification reaction to be carried out with higher amplification efficiency as compared to the conventional case, the amplification reaction time also can be shortened. Thus, according to the primer set of the present invention and a reagent including the same as well as the method of manufacturing an amplification product and a polymorphism analysis method, in each of which the primer set and the reagent are used, polymorphism in at least one obesity gene selected from the group consisting of the β2AR gene, the β3AR gene, and the UCP1 gene can be analyzed quickly and simply, and it therefore can be said that they are very effective in the field of medicine.

BEST MODE FOR CARRYING OUT THE INVENTION

Primer Set for Amplifying Obesity Gene

Figure 1:
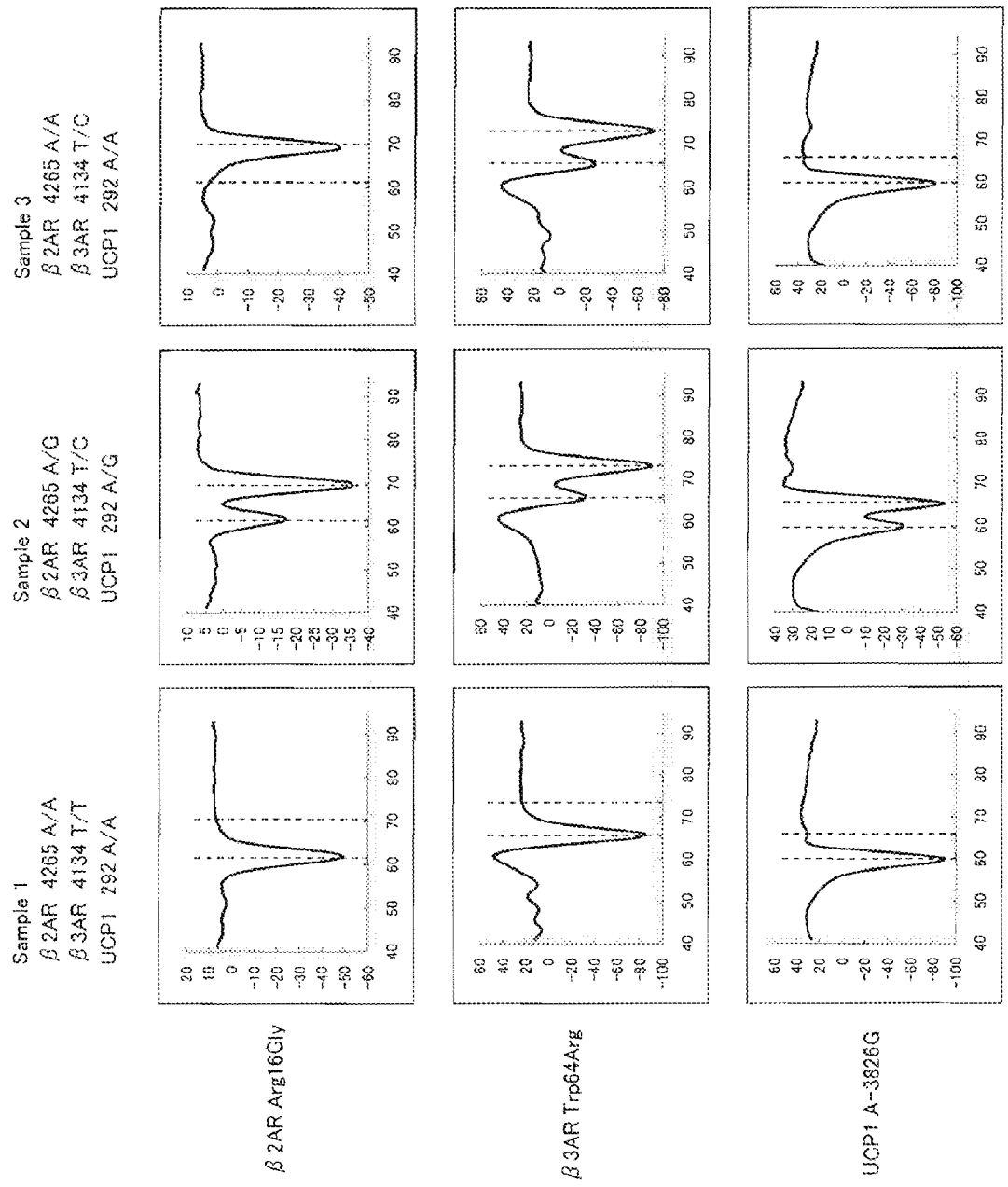
FIG. 1 shows graphs indicating the results of Tm analysis in Example 1 of the present invention.

As described above, the primer set for amplifying the obesity gene of the present invention is characterized by including at least one primer set selected from the group consisting of the aforementioned primer sets (1) to (3). The inclusion of at least one of the primer sets makes it possible, for example, to specifically amplify a specific target region in at least one obesity gene selected from the group consisting of the β2AR gene, the β3AR gene, and the UCP1 gene.

The primer set for amplifying the obesity gene of the present invention may include, for example, one of the aforementioned primer sets (1) to (3) or may include two or all of the primer sets (1) to (3). As described later, the target region that can be amplified specifically with the primer set (1) is a region including a site where the specific polymorphism in the β2AR gene is generated (base 4265 in SEQ ID NO: 1); the target region that can be amplified specifically with the primer set (2) is a region including a site where the specific polymorphism in the β3AR gene is generated (base 4134 in SEQ ID NO: 2); and the target region that can be amplified specifically with the primer set (3) is a region including a site where the specific polymorphism in the UCP1 gene is generated (base 292 in SEQ ID NO: 3).

As described above, each specific polymorphism in the β2AR gene, the β3AR gene, and the UCP1 gene, which are the obesity genes, is known as a polymorphism that affects metabolism. Therefore, it is considered to be important to examine not only a polymorphism of one of the genes but that of two or all of the three genes. However, the conventional methods have a problem in that a plurality of sequences cannot be analyzed in one reaction system. Conceivably, as described above, this is because the many isozymes exist in each obesity gene and thereby genes coding for isozymes other than the aforementioned genes also are amplified in PCR. Accordingly, among the β2AR gene, the β3AR gene, and the UCP1 gene, in order to examine polymorphisms of two or all of the three of them, it is necessary that the regions including the sites where the respective polymorphisms are generated are amplified in separate reaction systems, respectively, and the resultant amplification products are analyzed separately. Thus, with the conventional methods, it is very difficult to use only the specific gene selected from the obesity genes as a template and to specifically amplify only two or three types of target regions including the sites where polymorphisms are generated, respectively, in respective genes. Furthermore, since such analysis of even one sample is accompanied by a considerable amount of time and energy, there is a problem in that the analysis of multiple samples is not practical. On the contrary, according to the primer set for amplifying the obesity gene of the present invention, even in the case where two or all of the three types of the primer sets (1) to (3) are included, the respective target regions can be amplified in the same reaction solution simultaneously and specifically. Accordingly, the time and cost can be reduced, which is different from the aforementioned conventional methods. Furthermore, since two or three target regions are amplified specifically in the same reaction solution as described above, for example, the use of a probe complementary to a sequence to be detected in each target region makes it possible to perform Tm analysis directly using the aforementioned reaction solution to type each of the two or three types of polymorphisms. As described above, among the β2AR gene, the β3AR gene, and the UCP1 gene, since specific polymorphisms of two or three types of them can be analyzed in the same reaction solution, it is suitable for the primer set for amplifying the obesity gene of the present invention not only to include one of the primer sets (1) to (3) but also to include two or three of them. When not only one target region but also two or three target regions are amplified simultaneously using such a primer set for amplifying the obesity gene, polymorphisms in the obesity gene can be analyzed more efficiently as compared to the conventional cases.

Hereinafter, a forward primer also may be referred to as "F primer" and a reverse primer as "R primer".

First, the primer set (1) for amplifying the β2AR gene is explained. As described above, the primer set (1) is a primer set of a pair of primers including a forward primer composed of the following oligonucleotide (F1) and a reverse primer composed of the following oligonucleotide (R1).

(F1): at least one oligonucleotide selected from:

at least one oligonucleotide having a sequence identical to that of a region extending from thymine (T) at base 4248 to be considered as the first base to any one of the $18^{th}$ to $25^{th}$ bases in the direction toward the 5' end in the base sequence of SEQ ID NO: 1, with the thymine (T) being the 3' end, and at least one oligonucleotide having a sequence identical to that of a region extending from thymine (T) at base 4250 to be considered as the first base to any one of the 18$^{th}$ to 26$^{th}$ bases in the direction toward the 5' end in the base sequence of SEQ ID NO: 1, with the thymine (T) being the 3' end, and (R1): at least one oligonucleotide selected from:

at least one oligonucleotide complementary to a region extending from adenine (A) at base 4292 to be considered as the first base to any one of the 21$^{st}$ to 31$^{st}$ bases in the direction toward the 3' end in the base sequence of SEQ ID NO: 1, with thymine (T) complementary to the adenine (A) at base 4292 being the 3' end, and at least one oligonucleotide complementary to a region extending from adenine (A) at base 4301 to be considered as the first base to any one of the 18$^{th}$ to 27$^{th}$ bases in the direction toward the 3' end in the base sequence of SEQ ID NO: 1, with thymine (T) complementary to the adenine (A) at base 4301 being the 3' end.

The base sequence indicated in SEQ ID NO: 1 is a full-length sequence of the ADRβ2 gene coding for homo sapiens adrenergic, beta-2-, receptor, surface; ADRβ2 (β2AR) and, for example, has been registered at NCBI under the accession No. DQ094845.

Hereinafter, this primer set (1) also may be referred to as a "primer set for the β2AR gene". The primer set for the β2AR gene is a primer set for amplifying a DNA strand including a region from base 4249 to base 4291, a region from base 4249 to base 4300, a region from base 4251 to base 4291, or a region from base 4251 to base 4300 in SEQ ID NO: 1, as well as a strand complementary thereto. Base 4265 in this region (i.e. base 4265 in SEQ ID NO: 1) is known for the presence of a point mutation (4265A, 4265G). When the β2AR gene is translated to protein, the amino acid at position 16 is arginine (Arg) in the case where base 4265 is A, and a polymorphism having glycine (Gly) at position 16 of amino acid is indicated in the case where base 4265 is mutated to G. In the present invention, these polymorphisms can be indicated as 4265A/4265A or 4265G/4265G in the case of homozygote and as 4265A/4265G in the case of heterozygote. Further, when it is substituted by amino acid, 4265A/4265A can be expressed as Arg-16/Arg-16, 4265G/4265G can be expressed as Gly-16/Gly-16, and 4265A/4265G can be expressed as Arg-16/Gly-16. This amino acid notation is a general notation for a polymorphism in the target β2AR gene. When only the polymorphism in the β2AR gene is to be analyzed, it is sufficient to use only the primer set for the β2AR gene.

In the present invention, F1 primer and R1 primer of the primer set for the β2AR gene can be any primers, as long as the base located at the 3' end that serves to determine the site from which DNA polymerase starts amplification satisfies the aforementioned condition. Fixation of the base located at the 3' end of each primer in this manner makes it possible to sufficiently prevent the primer set for the β2AR gene from being bound to, for example, another similar isozyme gene (for example, the β1AR gene).

As described above, since the F1 primer and R1 primer each can be any primer as long as the base located at the 3' end is fixed, the length itself of each primer is not particularly limited and can be adjusted suitably to common length. The length of the primers is, for example, in the range of 13- to 50-mers, preferably 14- to 45-mers, and more preferably 15- to 40-mers. Specifically, it is preferable that the F1 primer be: at least one oligonucleotide having a sequence identical to that of a region extending from thymine (T) at base 4248 to be considered as the first base to any one of the 18$^{th}$ to 25$^{th}$ bases (preferably the 19$^{th}$ to 24$^{th}$ bases and more preferably the 19$^{th}$ to 23$^{rd}$ bases) in the direction toward the 5' end in the base sequence of SEQ ID NO: 1; or at least one oligonucleotide having a sequence identical to that of a region extending from thymine (T) at base 4250 to be considered as the first base to any one of the 18$^{th}$ to 26$^{th}$ bases (preferably the 19$^{th}$ to 24$^{th}$ bases and more preferably the 19$^{th}$ to 22$^{nd}$ bases) in the direction toward the 5' end in the base sequence of SEQ ID NO: 1. Furthermore, it is preferable that the R1 primer be: at least one oligonucleotide complementary to a region extending from adenine (A) at base 4292 to be considered as the first base to any one of the 21$^{st}$ to 31$^{st}$ bases (preferably the 22$^{nd}$ to 30$^{th}$ bases and more preferably the 23$^{rd}$ to 28$^{th}$ bases) in the direction toward the 3' end in the base sequence of SEQ ID NO: 1. Since 3' end of the F1 primer and the R1 primer is fixed, the region to be elongated from the primer is, for example, one of a region from base 4249 to base 4291, a region from base 4249 to base 4300, a region from base 4251 to base 4291, or a region from base 4251 to base 4300 in SEQ ID NO: 1 as described above. However, the length of the whole amplification product obtained varies according to the length of the primer to be used.

Furthermore, it is not necessary for the R1 primer and the F1 primer to be oligonucleotides perfectly complementary to the base sequence indicated in SEQ ID NO: 1 and the strand complementary to the base sequence, respectively. In other words, the part excluding the base located at the 3' end in each primer may be different in one to five bases from that of a perfectly complementary oligonucleotide.

With respect to oligonucleotide of the R1 primer, base complementary to base 4298 in SEQ ID NO: 1 may be either cytosine (C) or guanine (G). More preferably, as the R1 primer, both of oligonucleotide having cytosine at base complementary to base 4298 and oligonucleotide having guanine at base complementary to base 4298 are simultaneously used. With respect to base 4298 in SEQ ID NO: 1, the polymorphism (4298C or 4298G) has been known. However, the present invention is not intended to detect polymorphisms at this site. Therefore, use of both the aforementioned oligonucleotides as the R1 primer makes it possible to perform a gene amplification by the primer in either case of 4298C or 4298G. Accordingly, amplification of the target region can sufficiently be prevented from being affected by polymorphisms other than the target polymorphism. The ratio between oligonucleotide having cytosine at base complementary to base 4298 and oligonucleotide having guanine at base complementary to base 4298 is not particularly limited. For example, molar ratio of 1:10 to 10:1 is preferable.

Specific examples of the F1 primer and the R1 primer are indicated below but the present invention is not limited thereto. Base "s" in SEQ ID NOs: 12-22 indicates cytosine (C) or guanine (G) and is a base complementary to base 4298 in SEQ ID NO: 1. The combination of these F1 primer and R1 primer is not limited by any means. Specifically, however, a primer set (1') is particularly preferable, which includes a F1' primer composed of oligonucleotide of SEQ ID NO: 9 or SEQ ID NO: 109, and a R1' primer composed of oligonucleotide of SEQ ID NO: 12, SEQ ID NO: 18, or SEQ ID NO: 134. As described above, the R1' primer composed of oligonucleotide of SEQ ID NO: 12 and SEQ ID NO: 18 preferably includes both the oligonucleotide having cytosine at the base "s" and the oligonucleotide having guanine at the base "s". "Tm (° C.)" indicated below in the table is Tm (° C.) obtained when each sequence indicated below in the table was hybridized with the sequence perfectly complementary thereto. The "Tm (° C.)" is a value calculated by using MELTCALC software (http://www.meltcalc.com/), with parameters including an oligonucleotide concentration of 0.2 μM and a sodium equivalent (Na eq.) of 50 mM (the same applies below). The Tm value can be calculated by using, for example, conventionally known MELTCALC software (http://www.meltcalc.com/) or also can be determined by the nearest neighbor method (the same applies below). In the following table, as an example of the R1 primer, the Tm value in a condition where the R1 primer having guanine at the base "s" complementary to base 4298 in SEQ ID NO: 1 is indicated.

TABLE 1

| Primer | Sequence | Tm (° C.) | SEQ ID NO. |
|---|---|---|---|
| F1 Primer for β2AR gene | 5'-ggcaacccgggaacggcagcgcctt-3' | 71.1 | 4 |
| | 5'-gcaacccgggaacggcagcgcctt-3' | 69.8 | 5 |
| | 5'-caacccgggaacggcagcgcctt-3' | 67.9 | 6 |
| | 5'-aacccgggaacggcagcgcctt-3' | 67.4 | 7 |
| | 5'-acccgggaacggcagcgcctt-3' | 67.5 | 8 |
| | 5'-cccgggaacggcagcgcctt-3' | 66.4 | 9 |
| | 5'-ccgggaacggcagcgcctt-3' | 64.5 | 10 |
| | 5'-cgggaacggcagcgcctt-3' | 62.4 | 11 |
| | 5'-gcaacccgggaacggcagcgccttct-3' | 70.5 | 103 |
| | 5'-caacccgggaacggcagcgccttct-3' | 68.7 | 104 |
| | 5'-aacccgggaacggcagcgccttct-3' | 68.4 | 105 |
| | 5'-acccgggaacggcagcgccttct-3' | 68.5 | 106 |
| | 5'-cccgggaacggcagcgccttct-3' | 67.5 | 107 |
| | 5'-ccgggaacggcagcgccttct-3' | 65.8 | 108 |
| | 5'-cgggaacggcagcgccttct-3' | 64 | 109 |
| | 5'-gggaacggcagcgccttct-3' | 61.7 | 110 |
| | 5'-ggaacggcagcgccttct-3' | 59.5 | 111 |
| R1 Primer for β2AR gene | 5'-ccaccacccacacctcgtccctttsctgcgt-3' | 71.2 | 12 |
| | 5'-caccacccacacctcgtccctttsctgcgt-3' | 70.1 | 13 |
| | 5'-accacccacacctcgtccctttsctgcgt-3' | 69.9 | 14 |
| | 5'-ccacccacacctcgtccctttsctgcgt-3' | 69.1 | 15 |
| | 5'-cacccacacctcgtccctttsctgcgt-3' | 67.8 | 16 |
| | 5'-acccacacctcgtccctttsctgcgt-3' | 67.5 | 17 |
| | 5'-cccacacctcgtccctttsctgcgt-3' | 66.6 | 18 |
| | 5'-ccacacctcgtccctttsctgcgt-3' | 65 | 19 |
| | 5'-cacacctcgtccctttsctgcgt-3' | 63.4 | 20 |
| | 5'-acacctcgtccctttsctgcgt-3' | 62.7 | 21 |
| | 5'-cacctcgtccctttsctgcgt-3' | 61.5 | 22 |
| | 5'-catgccaccacccacacctcgtccct-3' | 68.7 | 129 |
| | 5'-atgccaccacccacacctcgtccct-3' | 68.4 | 130 |
| | 5'-tgccaccacccacacctcgtccct-3' | 68.6 | 131 |
| | 5'-gccaccacccacacctcgtccct-3' | 67.7 | 132 |
| | 5'-ccaccacccacacctcgtccct-3' | 65.6 | 133 |
| | 5'-ccaccacccacacctcgtccct-3' | 63.9 | 134 |
| | 5'-caccacccacacctcgtccct-3' | 62 | 135 |
| | 5'-accacccacacctcgtccct-3' | 61.1 | 136 |
| | 5'-ccacccacacctcgtccct-3' | 59.6 | 137 |
| | 5'-cacccacacctcgtccct-3' | 57.2 | 138 |

Next, the primer set (2) for amplifying the β3AR gene is explained. As described above, the primer set (2) is a primer set of a pair of primers including a forward primer composed of the following oligonucleotide (F2) and a reverse primer composed of the following oligonucleotide (R2).
(F2): at least one oligonucleotide having a sequence identical to that of a region extending from cytosine (C) at base 4110 to be considered as the first base to any one of the 16$^{th}$ to 20$^{th}$ bases in the direction toward the 5' end in the base sequence of SEQ ID NO: 2, with the cytosine (C) being the 3' end, and
(R2): at least one oligonucleotide complementary to a region extending from guanine (G) at base 4172 to be considered as the first base to any one of the 15$^{th}$ to 19$^{th}$ bases in the direction toward the 3' end in the base sequence of SEQ ID NO: 2, with cytosine (C) complementary to the guanine (G) at base 4172 being the 3' end.

The base sequence indicated in SEQ ID NO: 2 is a full-length sequence of the ADRβ2 gene coding for homo sapiens adrenergic, beta-2-, receptor: AD Rβ3 (β2AR) and, for example, has been registered at NCBI under the accession No. DQ104441.

Hereinafter, this primer set (2) also may be referred to as a "primer set for the β3AR gene". The primer set for the β3AR gene is a primer set for amplifying a DNA strand including a region from base 4111 to base 4171 in SEQ ID NO: 2, as well as a strand complementary thereto. Base 4134 in this region (i.e. base 4134 in SEQ ID NO: 2) is known for the presence of a point mutation (4134T, 4134C). When the β2AR gene is translated to protein, the amino acid at position 64 is tryptophan (Trp) in the case where base 4134 is T, and a polymorphism having arginine (Arg) at position 64 of amino acid is indicated in the case where base 4134 is mutated to C. These polymorphisms can be indicated as 4134T/4134T or 4134C/4134C in the case of homozygote and as 4134T/4134C in the case of heterozygote. Further, when it is substituted by amino acid, 4134T/4134T can be expressed as Trp-64/Trp-64, 4134C/4134C can be expressed as Arg-64/Arg-64, and 4134T/4134C can be expressed as Trp-64/Arg-64. This amino acid notation is a general notation for a polymorphism in the target β3AR gene. When only the polymorphism in the β3AR gene is to be analyzed, it is sufficient to use only the primer set for the β3AR gene.

In the present invention, the F2 primer and R2 primer of the primer set for the β3AR gene can be any primers, as long as the base located at the 3' end that serves to determine the site from which DNA polymerase starts amplification satisfies the aforementioned condition. Fixation of the base located at the 3' end of each primer in this manner makes it possible to sufficiently prevent the primer set for the β3AR gene from being bound to, for example, another similar isozyme gene (for example, the β1AR gene).

From the reason similar to that of the primer set for the β2AR gene, F2 primer and R2 primer of the primer set for the β3AR gene can be any primers, as long as the base located at the 3' end that serves to determine the site from which DNA polymerase starts amplification satisfies the aforementioned condition. Therefore, the length itself of the F2 primer and the R2 primer is not particularly limited and can be, for example, as described above. Specifically, it is preferable that the F2 primer be: at least one oligonucleotide having a sequence identical to that of a region extending from cytosine (C) at base 4110 to be considered as the first base to any one of the $16^{th}$ to $20^{th}$ bases (preferably the $17^{th}$ to $20^{th}$ bases and more preferably the $17^{th}$ to $19^{th}$ bases) in the direction toward the 5' end in the base sequence of SEQ ID NO: 2. Furthermore, it is preferable that the R2 primer be: at least one oligonucleotide complementary to a region extending from guanine (G) at base 4172 to be considered as the first base to any one of the $15^{th}$ to $19^{th}$ bases (preferably the $16^{th}$ to $19^{th}$ bases and more preferably the $16^{th}$ to $18^{th}$ bases) in the direction toward the 3' end in the base sequence of SEQ ID NO: 2. Since 3' end of the F2 primer and the R2 primer is fixed, the region to be elongated from the primer is, for example, the region from base 4111 to base 4171 in SEQ ID NO: 2 as described above. However, the length of the whole amplification product obtained varies according to the length of the primer to be used.

Furthermore, it is not necessary for the R2 primer and the F2 primer to be oligonucleotides perfectly complementary to the base sequence indicated in SEQ ID NO: 2 and the strand complementary to the base sequence, respectively. In other words, the part excluding the base located at the 3' end in each primer may be different in one to five bases from that of a perfectly complementary oligonucleotide.

Specific examples of the F2 primer and the R2 primer are indicated below but the present invention is not limited thereto. The combination of these F2 primer and R2 primer is not limited by any means. Specifically, however, a primer set (2') is particularly preferable, which includes a F2' primer composed of oligonucleotide of SEQ ID NO: 24 or SEQ ID NO: 25, and a R2' primer composed of oligonucleotide of SEQ ID NO: 28 or SEQ ID NO: 30.

TABLE 2

| Primer | Sequence | Tm (° C.) | SEQ ID NO. |
|---|---|---|---|
| F2 Primer for β3AR gene | 5'-ggccaccgtgggaggcaacc-3' | 64.3 | 23 |
|  | 5'-gccaccgtgggaggcaacc-3' | 62.3 | 24 |
|  | 5'-ccaccgtgggaggcaacc-3' | 59.4 | 25 |
|  | 5'-caccgtgggaggcaacc-3' | 56.9 | 26 |
|  | 5'-accgtgggaggcaacc-3' | 55.4 | 27 |
| R2 Primer for β3AR gene | 5'-ggctgcggccagcgaagtc-3' | 63 | 28 |
|  | 5'-gctgcggccagcgaagtc-3' | 60.9 | 29 |
|  | 5'-ctgcggccagcgaagtc-3' | 57.9 | 30 |
|  | 5'-tgcggccagcgaagtc-3' | 56.8 | 31 |
|  | 5'-gcggccagcgaagtc-3' | 54.9 | 32 |

Next, the primer set (3) for amplifying the UCP1 gene is explained. As described above, the primer set (3) is a primer set of a pair of primers including a forward primer composed of the following oligonucleotide (F3) and a reverse primer composed of the following oligonucleotide (R3).
(F3): at least one oligonucleotide having a sequence identical to that of a region extending from cytosine (C) at base 280 to be considered as the first base to any one of the $25^{th}$ to $44^{th}$ bases in the direction toward the 5' end in the base sequence of SEQ ID NO: 3, with the cytosine (C) being the 3' end, and
(R3): at least one oligonucleotide complementary to a region extending from cytosine (C) at base 350 to be considered as the first base to any one of the $23^{rd}$ to $38^{th}$ bases in the direction toward the 3' end in the base sequence of SEQ ID NO: 3, with guanine (G) complementary to the cytosine (C) at base 350 being the 3' end.

The base sequence indicated in SEQ ID NO: 3 is a gene sequence coding for human polymorphic region 5' of uncoupling protein; UCP and, for example, has been registered at NCBI under the accession No. U28479.

Hereinafter, this primer set (3) also may be referred to as a "primer set for the UCP1 gene". The primer set for the UCP1 gene is a primer set for amplifying a DNA strand including a region from base 281 to base 349 in SEQ ID NO: 3, as well as a strand complementary thereto. Base 292 in this region (i.e. base 292 in SEQ ID NO: 3) is known for the presence of a point mutation (292A, 292G). In the present invention, these polymorphisms can be indicated as 292A/292A or 292G/292G in the case of homozygote and as 292A/292G in the case of heterozygote. Base 292 in SEQ ID NO: 3 corresponds to base −3826 in mRNA of the UCP1 (base −3826 at upstream of a translation initiation site of the UCP1 gene) and the aforementioned polymorphisms are generally known for −3826A/−3826A, −3826G/−3826G, and −3826A/−3826G. When only the polymorphism in the UCP1 gene is to be analyzed, it is sufficient to use only the primer set for the UCP1 gene.

In the present invention, F3 primer and R3 primer of the primer set for the UCP1 gene can be any primers, as long as the base located at the 3' end that serves to determine the site from which DNA polymerase starts amplification satisfies the aforementioned condition. Fixation of the base located at the 3' end of each primer in this manner makes it possible to sufficiently prevent the primer set for the UCP1 gene from being bound to, for example, another similar isozyme gene (for example, the UCP2 gene, the UCP3 gene, and the UCP4 gene).

From the reason similar to that of the β2AR gene, the F3 primer and the R3 primer of the primer set for the UCP1 gene can be any primers, as long as the base located at the 3' end that serves to determine the site from which DNA polymerase starts amplification satisfies the aforementioned condition. Therefore, the length itself of the F3 primer and the R3 primer is not particularly limited and can be, for example, as described above. Specifically, it is preferable that the F3 primer be: at least one oligonucleotide having a sequence identical to that of a region extending from cytosine (C) at base 280 to be considered as the first base to any one of the $25^{th}$ to $44^{th}$ bases (preferably the $30^{th}$ to $40^{th}$ bases and more preferably the $32^{nd}$ to $37^{th}$ bases) in the direction toward the 5' end in the base sequence of SEQ ID NO: 3. Furthermore, it is preferable that the R3 primer be: at least one oligonucleotide complementary to a region extending from cytosine (C) at base 350 to be considered as the first base to any one of the $23^{rd}$ to $38^{th}$ bases (preferably the $25^{th}$ to $36^{th}$ bases and more preferably the $26^{th}$ to $32^{nd}$ bases) in the direction toward the 3' end in the base sequence of SEQ ID NO: 3. Since 3' end of the F3 primer and the R3 primer is fixed, the region to be elongated from the primer is, for example, the region from base 281 to base 349 in SEQ ID NO: 3 as described above. However, the length of the whole amplification product obtained varies according to the length of the primer to be used.

Furthermore, it is not necessary for the R3 primer and the F3 primer to be oligonucleotides perfectly complementary to the base sequence indicated in SEQ ID NO: 3 and the strand complementary to the base sequence, respectively. In other words, the part excluding the base located at the 3+ end in each primer may be different in one to five bases from that of a perfectly complementary oligonucleotide.

With respect to oligonucleotide of the R3 primer, base complementary to base 376 in SEQ ID NO: 3 may be either guanine (G) or thymine (T). More preferably, as the R3 primer, oligonucleotide having guanine at base complementary to base 376 and oligonucleotide having thymine at base complementary to base 376 are simultaneously used. With respect to base 376 in SEQ ID NO: 3, the polymorphism (376C or 376A) has been known. However, the present invention is not intended to detect polymorphisms at this site. Therefore, use of the aforementioned both oligonucleotides as the R3 primer makes it possible to perform a gene amplification by the primer in either case of 376C or 376A. Accordingly, amplification of the target region can sufficiently be prevented from being affected by polymorphisms other than the target polymorphism. The ratio between oligonucleotide having guanine at base complementary to base 376 and oligonucleotide having thymine at base complementary to base 376 is not particularly limited. For example, molar ratio of 1:10 to 10:1 is preferable.

Specific examples of the F3 primer and the R3 primer are indicated below but the present invention is not limited thereto. Base "k" in SEQ ID NOs: 53-64 indicates guanine (G) or thymine (T). With respect to SEQ ID NOs: 53-64 in the following Table, Tm values of the case where base complementary to base at 376 in SEQ ID NO: 3 being guanine and thymine are indicated, respectively. The combination of these F3 primer and R3 primer is not limited by any means. Specifically, however, a primer set (3') is particularly preferable, which includes a F3' primer composed of oligonucleotide of SEQ ID NO: 43 and a R3' primer composed of oligonucleotide of SEQ ID NO: 63. As described above, the R3' primer composed of oligonucleotide of SEQ ID NO: 63 preferably includes both of the oligonucleotide having guanine at the base "k" and the oligonucleotide having thymine at the base "k".

TABLE 3

| Primer | Sequence | Tm(° C.) | SEQ ID NO. |
|---|---|---|---|
| F3 Primer for UCP1 gene | 5'-ttatttaataggaagacattttgtgcagcgatttctgattgacc-3' | 63 | 33 |
| | 5'-tatttaataggaagacattttgtgcagcgatttctgattgacc-3' | 62.9 | 34 |
| | 5'-atttaataggaagacattttgtgcagcgatttctgattgacc-3' | 63.3 | 35 |
| | 5'-tttaataggaagacattttgtgcagcgatttctgattgacc-3' | 63.3 | 36 |
| | 5'-ttaataggaagacattttgtgcagcgatttctgattgacc-3' | 63.2 | 37 |
| | 5'-taataggaagacattttgtgcagcgatttctgattgacc-3' | 63.2 | 38 |
| | 5'-aataggaagacattttgtgcagcgatttctgattgacc-3' | 63.6 | 39 |
| | 5'-ataggaagacattttgtgcagcgatttctgattgacc-3' | 64.5 | 40 |
| | 5'-taggaagacattttgtgcagcgatttctgattgacc-3' | 63.5 | 41 |
| | 5'-aggaagacattttgtgcagcgatttctgattgacc-3' | 64 | 42 |
| | 5'-ggaagacattttgtgcagcgatttctgattgacc-3' | 63.4 | 43 |
| | 5'-gaagacattttgtgcagcgatttctgattgacc-3' | 62.2 | 44 |
| | 5'-aagacattttgtgcagcgatttctgattgacc-3' | 61.8 | 45 |
| | 5'-agacattttgtgcagcgatttctgattgacc-3' | 61.7 | 46 |
| | 5'-gacattttgtgcagcgatttctgattgacc-3' | 61 | 47 |
| | 5'-acattttgtgcagcgatttctgattgacc-3' | 60.5 | 48 |
| | 5'-cattttgtgcagcgatttctgattgacc-3' | 59.6 | 49 |
| | 5'-attttgtgcagcgatttctgattgacc-3' | 58.8 | 50 |
| | 5'-ttttgtgcagcgatttctgattgacc-3' | 58.7 | 51 |
| | 5'-tttgtgcagcgatttctgattgacc-3' | 58.4 | 52 |
| R3 primer for UCP1 gene | 5'-cccttatgacktagcaaaggagtggcagcaagttctg-3' | 67(g), 65.8(t) | 53 |
| | 5'-cctttatgacktagcaaaggagtggcagcaagttctg-3' | 66.1(g), 64.8(t) | 54 |
| | 5'-ctttatgacktagcaaaggagtggcagcaagttctg-3' | 65(g), 63.7(t) | 55 |
| | 5'-tttatgacktagcaaaggagtggcagcaagttctg-3' | 64.8(g), 63.4(t) | 56 |
| | 5'-ttatgacktagcaaaggagtggcagcaagttctg-3' | 64.8(g), 63.3(t) | 57 |
| | 5'-tatgacktagcaaaggagtggcagcaagttctg-3' | 64.7(g), 63.3(t) | 58 |
| | 5'-atgacktagcaaaggagtggcagcaagttctg-3' | 65.2(g), 63.7(t) | 59 |
| | 5'-tgacktagcaaaggagtggcagcaagttctg-3' | 65.3(g), 63.8(t) | 60 |
| | 5'-gacktagcaaaggagtggcagcaagttctg-3' | 64.5(g), 62.9(t) | 61 |
| | 5'-acktagcaaaggagtggcagcaagttctg-3' | 64.2(g), 62.5(t) | 62 |
| | 5'-cktagcaaaggagtggcagcaagttctg-3' | 63.3(g), 61.6(t) | 63 |
| | 5'-ktagcaaaggagtggcagcaagttctg-3' | 61.7(g), 61.1(t) | 64 |
| | 5'-tagcaaaggagtggcagcaagttctg-3' | 61 | 65 |
| | 5'-agcaaaggagtggcagcaagttctg-3' | 61.4 | 66 |
| | 5'-gcaaaggagtggcagcaagttctg-3' | 60.6 | 67 |
| | 5'-caaaggagtggcagcaagttctg-3' | 58.2 | 68 |

Furthermore, each primer of the aforementioned primer sets (1) to (3) may be, for example, one with the 5' end to which any conventionally known sequence has been added in order to increase the amplification reaction temperature.

Preferably, a primer set for amplifying the obesity gene of the present invention including at least one of the aforementioned primer sets (1) to (3) is used, for example, in amplifying the obesity gene in a biological sample such as a whole blood sample. Particularly, when the primer set for amplifying the obesity gene of the present invention is used in combination with a probe for detecting a polymorphism as described later, it is preferable that the ratio of the whole blood sample to be added to the reaction solution for amplifying a gene be 0.1 to 0.5 vol %. This will be described later.

<Reagent for Amplifying Obesity Gene>

As described above, a reagent for amplifying the obesity gene of the present invention is a reagent for amplifying the obesity gene by a gene amplification method, wherein the obesity gene is at least one selected from the group consisting of the β2AR gene, the β3AR gene, and the UCP1 gene, and wherein the reagent includes a primer set for amplifying the obesity gene of the present invention. The reagent for amplifying the obesity gene of the present invention is characterized by including a primer set of the present invention and, for example, compositions of other than this are not limited by any means.

For example, in order to detect an amplification product obtained by a gene amplification method in which a primer set of the present invention is used, the reagent for amplifying the obesity gene of the present invention further may include a probe that can hybridize to a site to be detected in the obesity gene. As described above, the primer set of the present invention allows specific amplification of each target region in three of the obesity genes by a gene amplification method according to, for example, the type of the primer sets (1) to (3) included therein. Accordingly, when a probe complementary to (i.e., a probe that can hybridize to) a sequence to be detected in each target region in the obesity gene described above is allowed to coexist, for example, the presence or absence of amplification or the genotype (polymorphism) of a site to be detected can be detected by the method described later. Such probes and the method of using them are explained later in the description of the polymorphism analysis method. Furthermore, it is preferable that the reagent for amplifying the obesity gene of the present invention be used in amplifying the obesity gene in a biological sample such as whole blood. Particularly, when the reagent for amplifying the obesity gene of the present invention is used in combination with the probe described above, it is preferable that the ratio of the whole blood sample to be added to the reaction solution for amplifying a gene be 0.1 to 0.5 vol %. In the present invention, the term "sequence to be detected" denotes a sequence including a site (site to be detected) at which a polymorphism is generated.

The form of the reagent for amplifying the obesity gene of the present invention is not particularly limited and it may be, for example, a liquid reagent containing a primer set for amplifying the obesity gene of the present invention or a dry reagent that is to be suspended in a solvent before use. Furthermore, the content of the primer set for amplifying the obesity gene also is not particularly limited.

<Method of Manufacturing Amplification Product>

As described above, the method of manufacturing an amplification product of the present invention is a method of manufacturing an amplification product of the obesity gene by a gene amplification method, wherein the obesity gene is at least one selected from the group consisting of the β2AR gene, the β3AR gene, and the UCP1 gene, and wherein the method includes the following step (I):

(I) amplifying at least one gene selected from the group consisting of the β2AR gene, the β3AR gene, and the UCP1 gene in a reaction solution using a primer set for amplifying the obesity gene of the present invention, with nucleic acid contained in a sample being used as a template.

When a primer set of the present invention is used to perform an amplification reaction in this manner, the target region in the obesity gene can be amplified as described above. Furthermore; when the primer set for amplifying the obesity gene of the present invention includes any two of the primer sets (1) to (3), with respect to any two of the obesity genes, target regions including respective sites to be detected can be amplified simultaneously in the same reaction solution. Moreover, when the primer set for amplifying the obesity gene of the present invention includes all the primer sets (1) to (3), with respect to the all three of obesity genes, target regions including respective sites to be detected can be amplified simultaneously in the same reaction solution. The target regions to be amplified according to the present invention are regions including the sites to be detected at which respective target polymorphisms in respective obesity genes are generated, respectively, as described above. The method of manufacturing an amplification product of the present invention is characterized by using a primer set of the present invention and, for example, the type and conditions of the gene amplification method are not limited by any means.

The gene amplification method is not particularly limited as described above. Examples thereof include the polymerase chain reaction (PCR) method, a nucleic acid sequence based amplification (NASBA) method, a transcription-mediated amplification (TMA) method, and a strand displacement amplification (SDA) method. However, the PCR method is preferable. The present invention is described below using the PCR method as an example but is not limited thereby.

The sample to which the present invention is to be applied is not particularly limited as long as it contains, for example, nucleic acid to serve as a template. However, it is preferable that the present invention be applied to, for example, a contaminated sample. Examples of the contaminated sample include whole blood, cells in the mouth (for example, oral mucosa), somatic cells of nails and hairs, germ cells, expectoration, amniotic fluid, paraffin-embedded tissue, urine, gastric juice (for example, gastric lavage fluid), and suspensions thereof. According to the method of manufacturing an amplification product using a primer set of the present invention, for example, even in the case of a sample (particularly, a biological sample such as whole blood or cells in the mouth) with various contaminants, the method is less subject to the effect thereof and allows respective target regions of three of the obesity genes to be amplified specifically. Thus, according to the present invention, even a highly contaminated sample, which is difficult to use in the conventional methods, can be used as it is, for instance, without being pretreated, for example, without being purified. Therefore, it can be said that an amplification product can be prepared quicker as compared to the conventional method also from the viewpoint of the pretreatment of the sample.

The ratio of the sample to be added to the reaction solution is not particularly limited. Specifically, when the sample is a biological sample (for example, a whole blood sample), the lower limit of the ratio thereof to be added to the reaction solution is, for example, preferably at least 0.01 vol %, more preferably at least 0.05 vol %, and further preferably at least 0.1 vol %. Furthermore, the upper limit of the ratio thereof to be added also is not particularly limited and is, for example, preferably 2 vol % or lower, more preferably 1 vol % or lower, and further preferably 0.5 vol. % or lower.

When an optical detection to be described later is intended to be performed, particularly, when an optical detection is performed using a labeled probe, it is preferable that the ratio of a biological sample, such as a whole blood sample, be set at, for example, 0.1 to 0.5 vol %. Generally, in the PCR reaction, a heat treatment is carried out to denature DNA (i.e. to dissociate it into a single-stranded DNA). This heat treatment may denature, for example, sugar or protein contained in the sample and thereby may generate an insolubilized precipitate or turbidity. Therefore, when the presence or absence of an amplification product or the genotype (polymorphism) of a site to be detected is to be checked by an optical method, the generation of such a precipitate or turbidity may affect measurement accuracy. However, when the ratio of the whole blood sample to be added to the reaction solution is set in the range described above, for example, an effect caused by generation of, for example, a precipitate due to denaturation can be prevented sufficiently and thereby the accuracy of measurement carried out by the optical method can be improved, although the mechanism thereof is unknown. Furthermore, since it also can sufficiently prevent PCR from being inhibited due to the contaminants contained in a whole blood sample, the amplification efficiency can be improved further. Accordingly, when in addition to the use of a primer set of the present invention, the ratio of the sample such as a whole blood sample to be added is set in the aforementioned range, further the need to pretreat the sample can be omitted.

Furthermore, the ratio of the whole blood sample in the reaction solution can be indicated not in the aforementioned volume ratio (for example, 0.1 to 0.5 vol %) but in a weight ratio of hemoglobin (hereinafter referred to as "Hb"). In this case, the ratio of the whole blood sample in the reaction solution is, for example, preferably in the range of 0.565 to 113 g/L, more preferably in the range of 2.825 to 56.5 g/L, and further preferably in the range of 5.65 to 28.25 g/L, in terms of the amount of Hb. The ratio of the whole blood sample to be added to the reaction solution may satisfy, for example, both the volume ratio and the Hb weight ratio, or one of them.

The whole blood may be any one of, for example, hemolyzed whole blood, unhemolyzed whole blood, anticoagulated whole blood, and whole blood containing coagulated fractions.

In the present invention, the target nucleic acid contained in a sample is, for example, DNA. The aforementioned DNA may be DNA contained originally in the sample, such as a biological sample, or an amplification product DNA obtained through amplification by a gene amplification method. In the latter case, an example thereof is cDNA that is generated from RNA (for example, total RNA or mRNA) contained originally in the sample by a reverse transcription reaction (for instance, reverse transcription PCR (RT-PCR)).

In the method of manufacturing an amplification product of the present invention, it is preferable that albumin further be added to the reaction solution before the start of a gene amplification reaction. Such addition of albumin further can reduce the effect of generation of a precipitate or turbidity described above and also further can improve the amplification efficiency. Specifically, it is preferable that albumin be added before the amplification reaction in step (I) or a step of dissociation into a single-stranded DNA.

The ratio of albumin to be added to the reaction solution is, for example, in the range of 0.01 to 2 wt %, preferably 0.1 to 1 wt %, and more preferably 0.2 to 0.8 wt %. The albumin is not particularly limited. Examples thereof include bovine serum albumin (BSA), human serum albumin, rat serum albumin, and horse serum albumin. One of them may be used or two or more of them may be used in combination.

Next, a method of manufacturing an amplification product of the present invention is described using an example in which with respect to a whole blood sample including DNA as target nucleic acid, amplification products of the β2AR gene, the β3AR gene, and the UCP1 gene are produced simultaneously in the same reaction solution by PCR using primer sets for amplifying the obesity gene of the present invention including the aforementioned primer sets (1) to (3). The present invention is characterized by using primer sets of the present invention and other configurations and conditions are not limited by any means.

First, a PCR reaction solution is prepared. The ratio of the primer sets of the present invention to be added is not particularly limited. However, it is preferable that each of the F primers of the primer sets (1) to (3) be added to be 0.1 to 2 µmol/L, more preferably 0.25 to 1.5 µmol/L, and particularly preferably 0.5 to 1 µmol/L. Furthermore, it is preferable that each of the R primers of the primer sets (1) to (3) be added to be 0.1 to 2 µmol/L, more preferably 0.25 to 1.5 µmol/L, and particularly preferably 0.5 to 1 µmol/L. The ratio (F:R, molar ratio) between the F primer and the R primer to be added of each primer set is not particularly limited. It is, for example, preferably 1:0.25 to 1:4 and more preferably 1:0.5 to 1:2.

The ratio of the whole blood sample in the reaction solution is not particularly limited but is preferably in the range described above. The whole blood sample may be added to the reaction solution without being treated or may be added to the reaction solution after being diluted with a solvent such as water or a buffer solution beforehand. When the whole blood sample is diluted beforehand, the dilution ratio is not particularly limited. It can be set so that, for example, the final ratio of the whole blood added to the reaction solution is in the aforementioned range, for example, 1:100 to 1:2000 and preferably 1:200 to 1:1000.

Other composition components in the reaction solution are not particularly limited and can be conventionally known components, whose ratios also are not particularly limited. Examples of the composition components include DNA polymerase, nucleotide (nucleoside triphosphate (dNTP)), and a solvent. Furthermore, as described above, it is preferable that the reaction solution further contain albumin. In the reaction solution, the order of addition of the respective composition components is not limited by any means.

The DNA polymerase is not particularly limited and, for example, a conventionally known thermoduric bacteria-derived polymerase can be used. Specifically, for example, *Thermus aquaticus*-derived DNA polymerase (U.S. Pat. No. 4,889,818 and U.S. Pat. No. 5,079,352) (trade name: Taq polymerase), *Thermus thermophilus*-derived DNA polymerase (WO 91/09950) (rTth DNA polymerase), *Pyrococcus furiosus*-derived DNA polymerase (WO 92/9689) (Pfu DNA polymerase; manufactured by Stratagenes), and *Thermococcus litoralis*-derived DNA polymerase (EP-A 455 430) (Trademark: Vent; manufactured by Biolab New England) are commercially available. Particularly, *Thermus aquaticus*-derived thermostable DNA polymerase is preferable.

The ratio of DNA polymerase to be added to the reaction solution is not particularly limited and is, for example, 1 to 100 U/mL, preferably 5 to 50 U/mL, and more preferably 20 to 30 U/mL. With respect to the unit of activity (U) of DNA polymerase, generally 1 U denotes the activity that allows all 10 nmol of nucleotide to be taken into an acid-insoluble precipitate in 30 minutes at 74° C. in a reaction solution for activity measurement, with an activated salmon sperm DNA being used as a template primer. The composition of the reaction solution for activity measurement is, for example, 25 mM TAPS buffer (pH 9.3, 25° C.), 50 mM KCl, 2 mM $MgCl_2$, 1 mM mercaptoethanol, 200 µM dATP, 200 µM dGTP, 200 µM dTTP, 100 µM [$\alpha^{-32}$P] dCTP, and 0.25 mg/mL activated salmon sperm DNA.

Generally, examples of the nucleoside triphosphate include dNTP (dATP, dCTP, dTTP). The ratio of dNTP to be added to the reaction solution is not particularly limited and is, for example, 0.01 to 1 mmol/L, preferably 0.05 to 0.5 mmol/L, and more preferably 0.1 to 0.3 mmol/L.

Examples of the solvent include buffer solutions such as Tris-HCl, Tricine, MES, MOPS, HEPES, and CAPS. Commercially available PCR buffer solutions or buffer solutions of commercially available PCR kits can be used.

Furthermore, the PCR reaction solution further may contain heparin, betaine, KCl, MgCl$_2$, MgSO$_4$, glycerol, etc. The ratios thereof to be added can be set, for example, in ranges in which the PCR reaction is not inhibited.

The total volume of the reaction solution is not particularly limited and can be determined suitably according to, for example, the equipment (thermal cycler) to be used. It is generally 1 to 500 μL and preferably 10 to 100 μL.

Subsequently, PCR is performed. The cycle conditions in PCR are not particularly limited, and, for example, (1) dissociation of whole blood-derived double-stranded DNA into single-stranded DNA, (2) annealing of a primer, and (3) elongation of a primer (polymerase reaction) are as described below. Furthermore, the number of cycles also is not particularly limited but preferably is at least 30, with the following three steps (1) to (3) being considered as one cycle. The upper limit thereof, in total, is not particularly limited and, for example, 100 cycles or less, preferably 70 cycles or less, and further preferably 50 cycles or less. The change in temperature in each step can be controlled automatically using, for example, a thermal cycler. When primer sets of the present invention are used, since they are excellent in amplification efficiency as described above, 50 cycles can be completed in approximately one hour (preferably within one hour) according to the present invention, while it takes approximately three hours to complete 50 cycles according to the conventional methods.

TABLE 4

| | Temperature (° C.) and Time (sec) |
|---|---|
| (1) Dissociation of single-stranded DNA | For example, 90 to 99° C., 1 to 120 sec Preferably 92 to 95° C., 1 to 60 sec |
| (2) Annealing of primer | For example, 40 to 70° C., 1 to 300 sec Preferably 50 to 70° C., 5 to 60 sec |
| (3) Elongation reaction | For example, 50 to 80° C., 1 to 300 sec Preferably, 50 to 75° C., 5 to 60 sec |

In the manner described above, amplification products of each target region of the β2AR gene, the β3AR gene, and the UCP1 gene can simultaneously be produced in the same reaction solution. When an amplification product complementary to respective target regions of any one or two of the three obesity genes is to be produced, a primer set for amplifying the obesity gene of the present invention containing, for example, one or two of the primer sets (1) to (3) corresponding to the target region(s) can be used.

The method of manufacturing an amplification product of the present invention further may include a step of detecting an amplification product obtained by the aforementioned amplification reaction. This makes it possible to detect the presence or absence of the amplification product or the genotype in the target region in the obesity gene. The presence or absence of the amplification product can be checked by a conventionally known method. Specifically, it can be checked by, for example, further adding a probe (for instance, a fluorescently-labeled probe) that can hybridize to a site to be detected in the β2AR gene, the β3AR gene, or the UCP1 gene to the reaction solution in step (I), and further in step (II), measuring the fluorescence intensity of the fluorescent label in the probe with respect to the reaction solution. Furthermore, when two or three target regions are to be amplified, it can be checked by, for example, further adding two or three probes (for instance, fluorescently-labeled probes) that can hybridize to the respective sites to be detected in the β2AR gene, the β3AR gene, and the UCP1 gene to the reaction solution in step (I), and further in step (II), measuring the fluorescence intensity of the fluorescent label in each probe with respect to the reaction solution. Detection of polymorphism in the obesity gene is described below as an embodiment of the present invention.

<Obesity Gene Polymorphism Analysis Method>

Polymorphism analysis method of the present invention is a method of analyzing the polymorphism of a site to be detected in the obesity gene, wherein the obesity gene is at least one selected from the group consisting of the β2AR gene, the β3AR gene, and the UCP1 gene, and wherein the method includes the following steps (i) to (iv):

(i) amplifying a region including a site to be detected in at least one gene selected from the group consisting of the β2AR gene, the β3AR gene, and the UCP1 gene in a reaction solution by a method of manufacturing an amplification product of the present invention, (ii) preparing a reaction solution that contains the amplification product obtained in step (i) and a probe capable of hybridizing to the site to be detected in at least one gene selected from the group consisting of the β2AR gene, the β3AR gene, and the UCP1 gene, (iii) measuring signal values that indicate melting states of a hybridization product between the amplification product and the probe while changing the temperature of the reaction solution, and (iv) determining a polymorphism of the site to be detected in at least one gene selected from the group consisting of the β2AR gene, the β3AR gene, and the UCP1 gene from a change in the signal values accompanying a change in the temperature.

In this manner, when an amplification product is produced using a primer set of the present invention, it is possible to amplify the target region including a site to be detected of a polymorphism in at least one obesity gene of the β2AR gene, the β3AR gene, and the UCP1 gene as described above and to analyze the polymorphism of the site to be detected in the target region.

The probe to be used in step (i) is not particularly limited. Preferable examples thereof include a probe that hybridizes to a site to be detected in the β2AR gene (hereinafter, also referred to as a "probe for the β2AR gene"), a probe that hybridizes to a site to be detected in the β3AR gene (hereinafter, also referred to as a "probe for the β3AR gene"), and a probe that hybridizes to a site to be detected in the UCP1 gene (hereinafter, also referred to as a "probe for the UCP1 gene"). Preferably, each of these probes is a probe complementary to a sequence to be detected containing the aforementioned site to be detected. Any one of those probes may be used or two or all three of them may be used. This can be determined, for example, according to the type of the target region(s) amplified with a primer set for amplifying the obesity gene of the present invention. When two or three probes are used, for example, the polymorphisms of two sites to be detected or all the three sites to be detected can be analyzed using the same reaction solution.

The probes for the obesity genes are not particularly limited and can be configured by a conventionally known method. For instance, each of them may be designed as a sequence to be detected containing a site to be detected of a polymorphism, based on the sequence of a sense strand or the sequence of an antisense strand of each obesity gene. Furthermore, the base located at the site to be detected of a polymorphism can be determined suitably according to the type of each polymorphism. In other words, in the case of the β2AR gene, since the polymorphisms of "A" and "G" at base 4265 in SEQ ID NO: 1 have been known, examples of the probe include a probe complementary to either a sequence to be detected including A at base 4265 or a sequence to be detected including G at base 4265 (a probe for detecting a sense strand), and a probe complementary to a sequence of an antisense strand thereof (a probe for detecting an antisense strand). Furthermore, in the case of the β3AR gene, since the polymorphisms of "T" and "C" at base 4134 in SEQ ID NO: 2 have been known, examples of the probe include a probe complementary to either a sequence to be detected including T at base 4134 or a sequence to be detected including C at base 4134 (a probe for detecting a sense strand), and a probe complementary to a sequence of an antisense strand thereof (a probe for detecting an antisense strand). Moreover, in the case of the UCP1 gene, since the polymorphisms of "A" and "G" at base 292 in SEQ ID NO: 3 have been known, examples of the probe include a probe complementary to either a sequence to be detected including A at base 292 or a sequence to be detected including G at base 292 (a probe for detecting a sense strand), and a probe complementary to a sequence of an antisense strand thereof (a probe for detecting an antisense strand). As described above, when a probe is designed, with the base located at the site to be detected where a polymorphism is generated being set to be any one of the bases as described above, it is also possible to judge what type of polymorphism is expressed at a target site to be detected in each obesity gene by the method as described later.

The probe can be added to an amplified reaction solution after step (i) i.e. after a target region in the obesity gene is subjected to an amplification reaction. However, it is preferable that the probe be added to a reaction solution before the amplification reaction in step (i) since this allows analysis to be performed easily and quickly.

The ratio of the probe to be added to the reaction solution is not particularly limited. For example, each probe is added to be preferably in the range of 10 to 400 nmol/L and more preferably in the range of 20 to 200 nmol/L. When a fluorescent dye is used as the label for a probe, an unlabeled probe with a sequence identical to that of the labeled probe may be used in combination with the labeled probe, for example, in order to adjust the fluorescence intensity to be detected, and the unlabeled probe may include phosphate group added to the 3' end thereof In this case, the molar ratio between the labeled probe and the unlabeled probe is preferably, for example, 1:10 to 10:1. The length of the probe is not particularly limited. It is, for example, 5- to 50-mers and preferably 10 to 30-mers.

The Tm value is described. When a solution containing double-stranded DNA is heated, the absorbance at 260 nm increases. This is because heating releases the hydrogen bonds between both strands in the double-stranded DNA to dissociate it into single-stranded DNA (i.e. DNA melting). When all double-stranded DNA are dissociated into single-stranded DNA, the absorbance thereof indicates approximately 1.5 times that obtained at the start of heating (i.e. absorbance of only double-stranded DNA), which makes it possible to judge that melting is completed thereby. Based on this phenomenon, the melting temperature Tm generally is defined as a temperature at which the absorbance has reached 50% of the total increase in absorbance.

In the aforementioned step (iii), the measurement of the signal values that indicate the melting states of the hybridization product between the amplification product and the probe may be a measurement of absorbance at 260 nm as described above but may be a measurement of the signal of a labeling substance. Specifically, it is preferable that a labeled probe labeled with a labeling substance be used as the aforementioned probe to perform the measurement of the signal of the labeling substance. The labeled probe can be, for example, a labeled probe that exhibits a signal independently but does not exhibit a signal after hybridization, or a labeled probe that does not exhibit a signal independently but exhibits a signal after hybridization. The former probe does not exhibit a signal when the probe is forming a hybrid (double-stranded DNA) with a sequence to be detected but exhibits a signal when the probe is released by heating. On the other hand, the latter probe exhibits a signal by forming a hybrid (double-stranded DNA) with a sequence to be detected but the signal is reduced (quenched) when the probe is released by heating. Accordingly, when the signal exhibited by the label is detected under a condition (absorption wavelength etc.) specific to the signal, the progress of melting of the hybridization product and the Tm value can be determined as in the case of the measurement of absorbance at 260 nm.

In the present invention, it is also possible to check respective polymorphisms with respect to amplification products of two or three of the obesity genes amplified in the same reaction solution. Accordingly, when two or three types of probes are used, it is preferable that they be labeled with the different labels (for example, fluorescent label) each of which is detected under its own condition. The use of different labels as described above makes it possible to analyze each amplification product separately by changing the detection conditions even in the same reaction solution.

Specific examples of labeling substances in the labeled probes include a fluorescent dye (fluorophore). A specific example of the labeled probes is preferably a probe that, for example, has been labeled with a fluorescent dye, exhibits fluorescence independently, and allows fluorescence to be reduced (for example, quenched) after hybridization. Generally, a probe that utilizes such a fluorescence quenching phenomenon is referred to as a fluorescence quenching probe. Particularly, with respect to the aforementioned probe, it is preferable that the 3' end or 5' end of oligonucleotide be labeled with a fluorescent dye and the base located at the end to be labeled be C. In this case, in the sequence to be detected, to which the labeled probe hybridizes, it is preferable that the base sequence of the labeled probe be designed so that the base to be paired with the end base C of the labeled probe or the base located 1 to 3 bases apart from the base to be paired be G. Generally, such a probe is referred to as a guanine quenching probe and is known as so-called QProbe (registered trademark). When such a guanine quenching probe hybridizes to a sequence to be detected, C located at the end, which has been labeled with a fluorescent dye, approaches G in the DNA to be detected, and thereby a phenomenon occurs that the emission of the fluorescent dye decreases (the fluorescence intensity decreases). The use of such a probe makes it possible to verify hybridization and dissociation easily according to a change in the signal.

The fluorescent dye is not particularly limited. Examples thereof include fluorescein, phosphor, rhodamine, and polymethine dye derivative. Examples of commercially available fluorescent dye include BODIPY FL (brand name, manufactured by Molecular Probe Inc.), FluorePrime (trade name, manufactured by Amersham Pharmacia), Fluoredite (trade name, manufactured by Millipore Corporation), FAM (manufactured by ABI), Cy3 and Cy5 (manufactured by Amersham Pharmacia), and TAMRA (manufactured by Molecular Probe Inc.). The combination of fluorescent dyes to be used for three types of probes is not particularly limited as long as, for example, it allows the respective probes to be detected under different conditions. Examples thereof include a combination of Pacific Blue (with a detection wavelength of 450 to 480 nm), TAMRA (with a detection wavelength of 585 to 700 nm), and BODIPY FL (with a detection wavelength of 515 to 555 nm).

Specific examples of the sequences of aforementioned probes for detecting each polymorphism of the β2AR gene, the β3AR gene, and the UCP1 gene are indicated below, but the present invention is not limited thereto. The following probe (1) is an example of the probe for the β2AR gene, and (1-1) is a probe for detecting a sense strand and (1-2) is a probe for detecting an antisense strand. The following probe (2) is an example of the probe for the β3AR gene, and (2-1) is a probe for detecting an antisense strand and (2-2) is a probe for detecting a sense strand. Furthermore, the following probe (3) is an example of the probe for the UCP1 gene and is a probe for detecting an antisense strand. One of the probes (P1) to (P3) may be used alone or two or more of them may be used in combination, as described later.

Probe (P1)

(1-1) At least one oligonucleotide complementary to a region extending from thymine (T) at base 4254 to be considered as the first base to any one of the 21$^{st}$ to 26$^{th}$ bases in the direction toward the 3' end in SEQ ID NO: 1, with adenine (A) complementary to the thymine being the 3' end, and (1-2) At least one oligonucleotide having a sequence identical to that of a region extending from cytosine (C) at base 4259 to be considered as the first base to any one of the 15$^{th}$ to 19$^{th}$ bases in the direction toward the 3' end in SEQ ID NO: 1, with the cytosine being the 5' end.

Probe (P2)

(2-1) At least one oligonucleotide having a sequence identical to that of a region extending from cytosine (C) at base 4140 to be considered as the first base to any one of the 17$^{th}$ to 28$^{th}$ bases in the direction toward the 5' end in SEQ ID NO: 2, with the cytosine being the 3' end, and (2-2) At least one oligonucleotide complementary to a region extending from guanine (G) at base 4144 to be considered as the first base to any one of the 12$^{th}$ to 17$^{th}$ bases in the direction toward the 5' end in SEQ ID NO: 2, with cytosine (C) complementary to the guanine being the 5' end.

Probe (3)

At least one oligonucleotide having a sequence identical to that of a region extending from cytosine (C) at base 280 to be considered as the first base to any one of the 17$^{th}$ to 31$^{st}$ bases in the direction toward the 3' end in SEQ ID NO: 3, with the cytosine being the 5' end.

In the probe (1-1), base complementary to base 4265 in SEQ ID NO: 1 is indicated with "y", and the "y" is T or C. In the probe (1-2), base 4265 in SEQ ID NO: 1 is indicated with "r", and the "r" is A or G. In the probe (2-1), base 4134 in SEQ ID NO: 2 is indicated with "y" and the "y" is T or C. In the probe (2-2), base complementary to base 4134 in SEQ ID NO: 2 is indicated with "r" and the "r" is A or G. In the probe (3), base 292 in SEQ ID NO: 3 is indicated with "r", and the "r" is A or G.

Specific examples of Probe (1), Probe (2), and Probe (3) are indicated in the following table. "Tm(° C.)" indicated below in the table is Tm(° C.) obtained when each sequence indicated below in the table was hybridized with the sequence perfectly complementary thereto. The "Tm(° C.)" is a value calculated by using MELTCALC software (http://www.meltcalc.com/), with parameters including an oligonucleotide concentration of 0.2 μM and a sodium equivalent (Na eq.) of 50 mM.

TABLE 5

| Probe | Sequence | Tm(° C.) | SEQ ID NO. |
|---|---|---|---|
| Probe (1) | 5'-cggcgcatggcttcyattgggtgcca-3' | | 69 |
| for | 5'-cggcgcatggcttcCattgggtgcca-3' | 69.2 | 69 |
| β2AR gene | 5'-ggcgcatggcttcyattgggtgcca-3' | | 70 |
| | 5'-ggcgcatggcttcCattgggtgcca-3' | 67.7 | 70 |
| | 5'-gcgcatggcttcyattgggtgcca-3' | | 71 |
| | 5'-gcgcatggcttcCattgggtgcca-3' | 66.2 | 71 |
| | 5'-cgcatggcttcyattgggtgcca-3' | | 72 |
| | 5'-cgcatggcttcCattgggtgcca-3' | 64.1 | 72 |
| | 5'-gcatggcttcyattgggtgcca-3' | | 73 |
| | 5'-gcatggcttcCattgggtgcca-3' | 62 | 73 |
| | 5'-catggcttcyattgggtgcca-3' | | 74 |
| | 5'-catggcttcCattgggtgcca-3' | 59.5 | 74 |
| | 5'-cccaatrgaagccatgcgc-3' | | 112 |
| | 5'-cccaatGgaagccatgcgc-3' | 58.7 | 112 |
| | 5'-cccaatrgaagccatgcg-3' | | 113 |
| | 5'-cccaatGgaagccatgcg-3' | 55.6 | 113 |
| | 5'-cccaatrgaagccatgc-3' | | 114 |
| | 5'-cccaatGgaagccatgc-3' | 52.4 | 114 |
| | 5'-cccaatrgaagccatg-3' | | 115 |
| | 5'-cccaatGgaagccatg-3' | 48.4 | 115 |
| | 5'-cccaatrgaagccat-3' | | 116 |
| | 5'-cccaatGgaagccat-3' | 46.1 | 116 |

In Table 5, oligonucleotides of SEQ ID NOs: 69 to 74 are specific examples of the probes (1-1) and the "y" in each base sequence may be either T or C as described below. In Table 5, the probes (1-1) that are expressed with SEQ ID NOs: 69 to 74 and having C at the base "y" are probes complementary to (perfectly matches with) the β2AR gene (a sense strand) having G at base 4265 in SEQ ID NO: 1 and the capitalized base C indicates base complementary to base G at 4265 in SEQ ID NO: 1. In Table 5, as specific examples, sequences of probes having C at the base "y", and Tm values (° C.) in the case where the probes hybridize to the sequences perfectly complementary thereto are indicated.

(SEQ ID NO: 72: y)
5'-cgcatggcttcyattgggtgcca-3'

(SEQ ID NO: 72, 101: y is C)
5'-cgcatggcttccattgggtgcca-3'

(SEQ ID NO: 72, 102: y is T)
5'-cgcatggcttctattgggtgcca-3'

In Table 5, oligonucleotides of SEQ ID NOs: 112 to 116 are specific examples of the probes (1-2) and the "r" in each base sequence may be either A or G as described below. In Table 5, the probes (1-2) that are expressed with SEQ ID NOs: 112 to 116 and having G at the "r" are probes complementary to (perfectly matches with) a strand complementary to the β2AR gene (an antisense strand) having G at base 4265 in SEQ ID NO: 1 and the capitalized base indicates base 4265 in SEQ ID NO: 1. In Table 5, as specific examples, sequences of probes having G at the base "r", and Tm values (° C.) in the case where the probes hybridize to the sequences perfectly complementary thereto are indicated.

TABLE 6

| Probe | Sequence | Tm(° C.) | SEQ ID NO. |
|---|---|---|---|
| Probe (2) for β3AR gene | 5'-ctggtcatcgtggccatcgccCggactc-3' | 69 | 75 |
| | 5'-tggtcatcgtggccatcgccCggactc-3' | 68.9 | 76 |
| | 5'-ggtcatcgtggccatcgccCggactc-3' | 68.1 | 77 |
| | 5'-gtcatcgtggccatcgccCggactc-3' | 66.7 | 78 |
| | 5'-tcatcgtggccatcgccCggactc-3' | 66.3 | 79 |
| | 5'-catcgtggccatcgccCggactc-3' | 65.5 | 80 |
| | 5'-atcgtggccatcgccCggactc-3' | 64.9 | 81 |
| | 5'-tcgtggccatcgccCggactc-3' | 65 | 82 |
| | 5'-cgtggccatcgccCggactc-3' | 64.1 | 83 |
| | 5'-gtggccatcgccCggactc-3' | 61.8 | 84 |
| | 5'-tggccatcgccCggactc-3' | 60.8 | 85 |
| | 5'-ggccatcgccCggactc-3' | 59.3 | 86 |
| | 5'-ctcggagtccGggcgat-3' | 57.5 | 117 |
| | 5'-ctcggagtccGggcga-3' | 57.2 | 118 |
| | 5'-ctcggagtccGggcg-3' | 55.7 | 119 |
| | 5'-ctcggagtccGggc-3' | 51.9 | 120 |
| | 5'-ctcggagtccGgg-3' | 47.1 | 121 |
| | 5'-ctcggagtccGg-3' | 42.8 | 122 |
| | 5'-ctcggagtccAggcgat-3' | 54.6 | 123 |
| | 5'-ctcggagtccAggcga-3' | 54.2 | 124 |
| | 5'-ctcggagtccAggcg-3' | 52.4 | 125 |
| | 5'-ctcggagtccAggc-3' | 48.4 | 126 |
| | 5'-ctcggagtccAgg-3' | 43.3 | 127 |
| | 5'-ctcggagtccAg-3' | 38.6 | 128 |
| Probe (3) for UCP1 gene | 5'-cacagtttgatcGagtgcatttgttaatgtg-P-3' | 59.4 | 87 |
| | 5'-cacagtttgatcGagtgcatttgttaatgt-P-3' | 58.7 | 88 |
| | 5'-cacagtttgatcGagtgcatttgttaatg-P-3' | 57.7 | 89 |
| | 5'-cacagtttgatcGagtgcatttgttaat-P-3' | 56.9 | 90 |
| | 5'-cacagtttgatcGagtgcatttgttaa-P-3' | 56.7 | 91 |
| | 5'-cacagtttgatcGagtgcatttgtta-P-3' | 56.4 | 92 |
| | 5'-cacagtttgatcGagtgcatttgtt-P-3' | 56.7 | 93 |
| | 5'-cacagtttgatcGagtgcatttgt-P-3' | 56.3 | 94 |
| | 5'-cacagtttgatcGagtgcatttg-P-3' | 55 | 95 |
| | 5'-cacagtttgatcGagtgcattt-P-3' | 53.8 | 96 |
| | 5'-cacagtttgatcGagtgcatt-P-3' | 53.2 | 97 |
| | 5'-cacagtttgatcGagtgcat-P-3' | 52.6 | 98 |
| | 5'-cacagtttgatcGagtgca-P-3' | 53.2 | 99 |
| | 5'-cacagtttgatcGagtgc-P-3' | 50.4 | 100 |
| | 5'-cacagtttgatcGagtg-P-3' | 46.7 | 139 |

In Table 6, probes (2-1) that are expressed with SEQ ID NOs: 75 to 86 each composed of a sequence identical to that of a region having C at base 4134 in SEQ ID NO: 2, and the capitalized base indicates base 4134 in SEQ ID NO: 2. In each probe (2-1), the capitalized base can be replaced by "y", and the "y" may be either C or T. In Table 6, the probes (2-2) that are expressed with SEQ ID NOs: 117 to 128 each composed of a sequence complementary to a region having C at base 4134 in SEQ ID NO: 2, and the capitalized base indicates base complementary to base 4134 in SEQ ID NO: 2. In each probe (2-2), the capitalized base can be replaced by "r", and the "r" may be either G or A. In Table 6, the probes (3) that are expressed with SEQ ID NOs: 87 to 100 and 139 each composed of a sequence identical to that of a region having G at base 292 in SEQ ID NO: 3, and the capitalized base indicates base 292 in SEQ ID NO: 3. In each probe (3), the capitalized base can be replaced by "r", and the "r" may be either G or A. As described above, specific examples of the probe according to the present invention may be strands complementary to oligonucleotides indicated in the above table.

The aforementioned probes are examples and the present invention is not limited thereto. With respect to the probe for the β2AR gene, a preferable probe among the probes (1-1) is oligonucleotide consisting of the base sequence of SEQ ID NO: 72, and the base "y" may be either T or C, as described above. Further, a preferable probe among the probes (1-2) is oligonucleotide consisting of the base sequence of SEQ ID NO: 114, and the base "r" may be either A or G. With respect to the probe for the β2AR gene, a so-called wild-type detecting probe is preferably used in combination with a so-called mutation type detecting probe. In this state, the wild-type detecting probe is, for example, a probe for detecting a sequence to be detected having A (or G) at base 4265 in SEQ ID NO:1 (a sense strand) or a strand complementary thereto (an antisense strand), and the mutation type detecting probe is a probe for detecting a sequence to be detected having G (or A) at base 4265 in SEQ ID NO:1 (a sense strand) or a strand complementary thereto (an antisense strand). In the present invention, among the probes (1-1), at least one oligonucleotide consisting of the base sequence of SEQ ID NOs: 69 to 74 having C at the base "y" (the mutation type detecting probe) is preferably used in combination with at least one oligonucleotide consisting of the base sequence of SEQ ID NOs: 69 to 74 having T at the base "y" (the wild-type detecting probe), and more preferably, oligonucleotide consisting of the base sequence of SEQ ID NO: 72 having C at the base "y" (the mutation type detecting probe) is used in combination with oligonucleotide consisting of the base sequence of SEQ ID NO: 72 having T at the base "y" (the wild-type detecting probe).

The inventors of the present invention conducted the study on polymorphism analysis separately. As a result, they found that it was difficult to detect signals by the Tm analysis using probes in the case where the β2AR gene polymorphism (polymorphism of a site coding for position 16 of amino acid in β2AR: polymorphism of base at 4265 in SEQ ID NO: 1) is analyzed. Then, as a result of further keen study, the inventors found that, with respect to the probe (1), particularly with respect to oligonucleotide consisting of the base sequence of SEQ ID NO: 72 (i.e., oligonucleotide of SEQ ID NO: 101 and oligonucleotide of SEQ ID NO: 102), a signal that matches with the amplification product of the β2AR gene and a signal that mismatches with the amplification product of the β2AR gene can separately be detected in a sufficient manner, as described later. The probe that is expressed with SEQ ID NO: 101 is a probe that perfectly matches with a sequence to be detected in the β2AR gene (a sense strand) having G at base 4265 in SEQ ID NO: 1. The probe that is expressed with SEQ ID NO: 102 is a probe that perfectly matches with a sequence to be detected in the β2AR gene (a sense strand) having A at base 4265 in SEQ ID NO: 1. Since the present invention is characterized by simultaneously and specifically amplifying respective target regions of the three of genes in the same reaction solution using the primer set for amplifying the obesity gene, as described above, a sequence of the probe to be used for analyzing the amplification product obtained is not particularly limited.

With respect to the probe for the β3AR gene a preferable probe among the probes (2-1) is oligonucleotide consisting of the base sequence of SEQ ID NO: 83. Further, with respect to the probe (2-2), a so-called wild-type detecting probe is preferably used in combination with a so-called mutation type detecting probe. In this state, the wild-type detecting probe is, for example, a probe for detecting a sequence to be detected having T at base 4134 in SEQ ID NO:2 (a sense strand) or a strand complementary thereto (an antisense strand), and the mutation type detecting probe is a probe for detecting a sequence to be detected having C at base 4134 in SEQ ID NO:2 (a sense strand) or a strand complementary thereto (an antisense strand). In the present invention, for example, at least one oligonucleotide consisting of the base sequence of SEQ ID NOs: 117 to 122 (the mutation type detecting probe) is preferably used in combination with at least one oligonucleotide consisting of the base sequence of SEQ ID NOs: 123 to 128 (the wild-type detecting probe), and more preferably, oligonucleotide consisting of the base sequence of SEQ ID NO: 120 (the mutation type detecting probe) is used in combination with oligonucleotide consisting of the base sequence of SEQ ID NO: 127 (the wild-type detecting probe). In this manner when the wild-type detecting probe is used in combination with the mutation type detecting probe, for example, the Tm value of perfect matching of each probe is preferably set at different values.

With respect to the probe for the UCP1 gene, a preferable probe among the probes (3) is oligonucleotide consisting of the base sequence of SEQ ID NO: 95 or SEQ ID NO: 139.

When two or more of these probes are used, as described above, it is preferable that they be labeled with different fluorescent dyes (fluorescent dyes that are detected at different wavelengths). For instance, when the probes indicated in the above table are quenching probes, it is preferable that in the probe (1-1) and the probe (2-1), the 3' end thereof be labeled with a fluorescent dye (for instance, Pacific Blue, BODIPY FL) as described above and in the probe (1-2), the probe (2-2), and the probe (3), cytosine at the 5' end thereof be labeled with a fluorescent dye (for instance, TAMRA) as described above. Although the 3' end of the probe (1-1) indicated in the above table is adenine (A), since hybridization of adjacent cytosine (C) and guanine (G) makes it possible to confirm quenching, it can be used as a guanine quenching probe. Furthermore, a probe with the 5' end labeled with a fluorescent dye may have the 3' end, to which a phosphate group further may be added, in order to, for example, prevent the probe itself from elongating. Moreover, when the wild-type detecting probe and the mutation type detecting probe are used as described above, each fluorescent dye may be the same or different.

Next, with respect to the detection method of the present invention, a method of detecting polymorphism in the β2AR gene (polymorphism of a base 4265 in SEQ ID NO: 1), polymorphism in the β3AR gene (polymorphism of a base 4134 in SEQ ID NO: 2), and polymorphism in the UCP1 gene (polymorphism of a base 292 in SEQ ID NO: 3) using the following probes is described as an example. However, the present invention is not limited thereto.

<Probes>

```
Probe for β2AR gene
                                          (SEQ ID NO: 72)
5'-cgcatggcttcCattgggtgcca-(Pacific Blue)-3'
or (SEQ ID NO: 114)
5'-(Pacific Blue)-cccaatGgaagccatgc-P-3'

Probe for β3AR gene
                                          (SEQ ID NO: 83)
5'-cgtggccatcgccCggactc-(BODIPY FL)-3'
or;

(SEQ ID NO: 120)
5'-(BODIPY FL)-ctcggagtccGggc-P-3'
and (SEQ ID NO: 127)
5'-(BODIPY FL)-ctcggagtccAggc-P-3'

Probe for UCP1 gene
                                          (SEQ ID NO: 95)
5'-(TAMRA)-cacagtttgatcGagtgcatttg-3'
or (SEQ ID NO: 139)
5'-(TAMRA)-cacagtttgatcGagtg-3'
```

First, using a reaction solution containing the aforementioned three labeled probes added thereto, PCR was performed as described above, and thereby the respective regions of the β2AR gene, the β3AR gene, and the UCP1 gene are amplified at the same time in the same reaction solution.

Next, the amplification products thus obtained are dissociated and then single-stranded DNA obtained through dissociation is hybridized with the labeled probes. This can be carried out through, for example, a change in the temperature of the reaction solution.

The heating temperature in the dissociation step is not particularly limited as long as it allows the amplification products to be dissociated. It is, for example, 85 to 95° C. The heating time also is not particularly limited and generally is 1 second to 10 minutes and preferably 1 second to 5 minutes.

The dissociated single-stranded DNA can be hybridized with the labeled probes by, for example, decreasing the heating temperature employed in the dissociation step after the dissociation step. The temperature condition is, for example, 40 to 50° C.

The temperature of the reaction solution is changed and thereby signal values that indicate the melting states of hybridization products between the amplification products and the labeled probes are measured. Specifically, for example, the reaction solution (the hybridization products between the single-stranded DNA and the labeled probes) is heated, and thereby the change in the signal values accompanying the temperature rise is measured. As described above, when, for example, a guanine quenching probe is used, fluorescence decreases (or quenches) in the state where the probe has been hybridized with the single-stranded DNA, while fluorescence is emitted in the state where the probe has been dissociated. Accordingly, for example, the hybridization product in which the fluorescence has decreased (or quenched) is heated gradually and the increase in fluorescence intensity accompanying the temperature rise may be measured.

The temperature range in which the change in fluorescence intensity is to be measured is not particularly limited. For example, the start temperature is room temperature to 85° C. and preferably 25 to 70° C., while the end temperature is, for example, 40 to 105° C. Furthermore, the rate of temperature rise is not particularly limited and is, for example, 0.1 to 20° C./sec and preferably 0.3 to 5° C./sec.

Next, the Tm value is determined by analyzing a change in the signal. Specifically, the amount of change in the fluorescence intensity per unit time at each temperature (–d fluorescence intensity increase/dt) is calculated from the fluorescence intensity obtained and the temperature at which the lowest value is obtained is determined as the Tm value. It is also possible to determine, as the Tm value, the point at which the amount of increase in the fluorescence intensity per unit time (d fluorescence intensity increase/dt) is the highest. On the contrary, the amount of decrease in the fluorescence intensity is measured when the labeled probe used is not a quenching probe but a probe that does not exhibit a signal independently but exhibits a signal after hybridization.

In the present invention, in order to detect respective polymorphisms of three genes, the respective Tm values are determined under conditions according to the respective labels of the three types of probes. Pacific Blue of a probe for the β2AR gene, can be detected with, for example, a detection wavelength of 450 to 480 nm, BODIPY FL of a probe for the β3AR gene, can be detected with, for example, a detection wavelength of 515 to 555 nm, and TAMRA of a probe for the UCP1 gene, can be detected with, for example, a detection wavelength of 585 to 700 nm.

From such Tm values, the genotypes in the respective sites to be detected of the respective genes are determined. In the Tm analysis, the case of a perfectly complementary hybrid (matching) results in a higher Tm value indicating dissociation than that obtained in the case of a hybrid including a different single base (mismatching). Accordingly, when with respect to the probe, the Tm value obtained in the case of a perfectly complementary hybrid and the Tm value obtained in the case of a hybrid including a different single base are determined beforehand, it can be determined whether the amplification product matches or mismatches with the probe. For example, in the case where the base of the target site located at the sequence to be detected is assumed to be of a mutation type (with, for instance, G at base 4265 in SEQ ID NO: 1), when using a probe complementary to the sequence to be detected containing the base, the polymorphism of the amplification product can be judged as a mutation type if the Tm value of the resultant hybrid is equal to the Tm value of a perfectly complementary hybrid. Furthermore, the polymorphism of the amplification product can be judged as a wild-type (with, for example, A at base 4265 in SEQ ID NO: 1) if the Tm value of the resultant hybrid is equal to the Tm value of the hybrid including a different single base (i.e. a lower value than the Tm value of the perfectly complementary hybrid). Moreover, when both the Tm values are detected, it can be judged as heterozygote. Thus, respective polymorphisms of the β2AR gene, the β3AR gene, and the UCP1 gene can be judged from the Tm values with respect to the respective labeled probes. When the Tm value is confirmed by detecting the fluorescence intensity, in order to sufficiently distinguish the signal of matching and the signal of mismatching, it is preferable that an unlabeled probe with an oligonucleotide sequence identical to that of the labeled probe may be used in combination with the labeled probe. Among the probe for the β2AR gene, the probe for the β3AR gene, and the probe for the UCP1 gene, it is not particularly limited to which the unlabeled probe is added in combination with the labeled probe. For example, it is preferable that the labeled probe and the unlabeled probe are added to the probe for the β3AR gene.

In the present invention, for example, a change in the signal during hybridization may be measured instead of the method in which the temperature of a reaction solution containing the probes is increased (a hybridization product is heated) and a change in the signal accompanying the temperature rise is measured as described above. In other words, when the temperature of the reaction solution containing the aforementioned probes is decreased to form hybridization products, the change in the signal accompanying the temperature decrease may be measured.

Specifically, when using a labeled probe that exhibits a signal independently but does not exhibit a signal after hybridization (for example, a guanine quenching probe), the labeled probe emits fluorescence in the state where single-stranded DNA and the probe are dissociated, but the fluorescence decreases (or quenches) when a hybrid is formed through temperature decrease. Accordingly, for example, the temperature of the reaction solution is decreased gradually and the decrease in fluorescence intensity accompanying the temperature decrease may be measured. On the other hand, when using a labeled probe that does not exhibit a signal independently but exhibits a signal after hybridization, the labeled probe does not emit fluorescence in the state where single-stranded DNA and the probe are dissociated, but the fluorescence is emitted when a hybrid is formed through temperature decrease. Accordingly, for example, the temperature of the reaction solution is decreased gradually and thereby the increase in fluorescence intensity accompanying the temperature decrease may be measured.

When polymorphism of one or two of the three obesity genes (the β2AR gene, the β3AR gene, and the UCP1 gene) is to be analyzed, for instance, a primer set for amplifying the obesity gene of the present invention m ay be used that includes one or two types of primer sets corresponding to the target regions that are selected from the primer sets (1) to (3), and furthermore, one or two probes that hybridize to target sites to be detected may be used.

<Probe for Analyzing β2AR Gene>

A probe for analyzing the obesity gene of the present invention is a probe used for a polymorphism analysis of the obesity gene, wherein the obesity gene is the β2AR gene, and wherein the probe is composed of the following oligonucleotide (P1):

(P1) at least one oligonucleotide of the following (1-1) and (1-2):

(1-1) at least one oligonucleotide complementary to a region extending from thymine (T) at base 4254 to be considered as the first base to any one of the 21$^{st}$ to 26$^{th}$ bases in the direction toward the 3' end in SEQ ID NO: 1, with adenine (A) complementary to the thymine being the 3' end, and (1-2) at least one oligonucleotide having a sequence identical to that of a region extending from cytosine (C) at base 4259 to be considered as the first base to any one of the 15$^{th}$ to 19$^{th}$ bases in the direction toward the 3' end in SEQ ID NO: 1, with the cytosine being the 5' end.

The probe composed of the oligonucleotide indicated in the aforementioned (P1) is a probe for the β2AR gene and is as described above.

The probe for the β2AR gene of the present invention makes it possible to detect a sequence to be detected including a site coding for position 16 of β2AR amino acid in the β2AR gene. Specifically, use of the probe of the present invention makes it possible to perform a melting temperature analysis of the hybridization product between, for example, the probe of the present invention and the sequence to be detected with an excellent reliability. Further, the melting temperature analysis makes it possible to analyze the presence or absence and an amount of the sequence to be detected in a sample, and to determine a polymorphism of the site to be detected in the sequence to be detected (polymorphism of base 4265 in SEQ ID NO: 1) with an excellent reliability. Accordingly, the probe for analyzing the β2AR gene of the present invention can be used for a β2AR gene analysis, as described later. Specifically, the probe for analyzing the β2AR gene of the present invention can be used for, for example, a melting temperature analysis and a polymorphism analysis of the β2AR gene by the melting temperature analysis. Further, the probe can be used for a polymorphism analysis method of the aforementioned three obesity genes. Accordingly, it can be said that the probe for analyzing the β2AR gene and the analysis method of the present invention are very useful tool and analysis method especially in the field of medicine performing treatment and prevention of obesity.

The probe for the β2AR gene may be, for example, an unlabeled probe not labeled with a labeling substance. However, a labeled probe labeled with a labeling substance is preferable. The labeling sites and the labeling substances are as described above.

<Reagent for Analyzing β2AR Gene>

The reagent for analyzing the obesity gene of the present invention is a reagent used for a β2AR gene analysis, wherein the reagent includes a probe for analyzing the β2AR gene of the present invention (hereinafter referred to as "a reagent for analyzing the β2AR gene"). The analysis reagent of the present invention can be used for, as described later, a β2AR gene analysis. Specifically, the analysis reagent of the present invention can be used, for example, for a melting temperature analysis and a polymorphism analysis of the β2AR gene by the melting temperature analysis. Further, the analysis reagent of the present invention can also be used for a polymorphism analysis of two or three types of the obesity genes including the β2AR gene. The reagent for analyzing the β2AR gene of the present invention is characterized by including a probe for analyzing the β2AR gene of the present invention and compositions of other than this are not limited by any means.

Preferably, the reagent for analyzing the β2-AR gene of the present invention further includes a primer for amplifying a sequence to be detected including the site to be detected in the β2AR gene. An example of the primer includes the aforementioned primer set for the β2AR gene. Use of the analysis reagent of the present invention including the primer set for the β2AR gene makes it possible to perform an amplification reaction of the β2AR gene. Further, use of the amplification product obtained by the reaction makes it possible to perform a β2AR gene analysis. A region to be amplified by the primer for the β2AR gene can be any region, as long as it includes the site to be detected in the β2AR gene. A specific example thereof includes a sequence to be detected including the site to be detected in the β2AR gene. In other words, the region may be either the sequence to which the probe of the present invention hybridizes or a region including the aforementioned sequence to be detected. Hereinafter, a region to be amplified by the amplification reaction referred to as "a target region".

It is preferable that the reagent for analyzing the β2AR gene of the present invention be used in analyzing the β2AR gene in a biological sample such as whole blood. Particularly, when the reagent for analyzing the β2AR gene of the present invention includes the primer set for the β2AR gene besides a probe for analyzing the β2AR gene of the present invention and is used for an amplification of a site to be detected, it is preferable that the ratio of the whole blood sample to be added to the reaction solution for the amplification reaction be 0.1 to 0.5 vol %. Regarding this point, it is as described above.

The form of the reagent for analyzing the β2AR gene of the present invention is not particularly limited and it may be, for example, a liquid reagent containing a probe for analyzing the β2AR gene of the present invention or a dry reagent that is to be suspended in a solvent before use. Furthermore, the content of the probe for analyzing the β2AR gene also is not particularly limited.

The reagent for analyzing the β2AR gene of the present invention may further contain a probe and a primer for detecting other genes and other polymorphisms in the same reaction solution. As described above, as same as the β2AR gene, since polymorphisms of the β3AR gene and the UCP1 gene are known for a marker of treatment and prevention of obesity, the reagent may further contain a probe and a primer set for detecting one of or both of the β3AR gene and the UCP1 gene. In this manner, for example, when the target regions of plural genes are amplified to perform detection by the probe, since the target region of the β2AR gene can specifically be amplified, it is preferable that the reagent includes the primer set for the β2AR gene as described above.

<β2AR Gene Analysis Method>

Obesity gene analysis method of the present invention is a method of analyzing the β2AR gene, wherein the method includes the following steps (a) to (c):

(a) preparing a reaction solution that contains a sequence to be detected including a site to be detected of a polymorphism in the β2AR gene and a probe for analyzing the β2AR gene of the present invention, (b) measuring signal values that indicate melting states of a hybridization product between the sequence to be detected and the probe for analyzing the β2AR gene while changing the temperature of the reaction solution, and (c) determining a melting temperature of the hybridization product from a change in the signal values accompanying a change in the temperature.

In this manner, use of the probe for analyzing the β2AR gene of the present invention makes it possible to sufficiently detect a change in the signal values that indicate melting states of a hybridization product between the sequence to be detected and the probe for analyzing the β2AR gene. Therefore, according to the β2AR gene analysis method of the present invention, determination of the melting temperature with respect to a sequence to be detected of the β2AR gene can be performed with a high reliability. Accordingly, for example, when nucleic acid amplification is performed with respect to a region including a site to be detected of the β2AR gene, the presence or absence of the amplification of the target region can be judged by analyzing the melting temperature (Tm) with a high reliability. Further, the Tm value in the case where the sequence to be detected perfectly matches with the probe of the present invention and the Tm value in the case where the sequence to be detected mismatches with the probe of the present invention show difference which can sufficiently be determined. Therefore, it can sufficiently be distinguished whether the β2AR gene to be detected perfectly matches with the probe of the present invention or mismatches with the probe of the present invention. In this manner, when the perfect matching and the mismatching can sufficiently be distinguished, polymorphism of the β2AR gene to be detected can be judged with further excellent reliability. The β2AR gene analysis method of the present invention is characterized by using a probe for analyzing the β2AR gene of the present invention and, for example, types of signals to be measured, method of measurement, and conditions of measurement are not limited by any means.

Since, the β2AR gene analysis method of the present invention can determine the Tm values as described above, the method may further includes the following step (d):
(d) determining polymorphism of the site to be detected in the β2AR gene from the melting temperature determined.

The β2AR gene analysis method of the present invention may further includes the following step (x). Such a method makes it possible to continuously perform, for example, a β2AR gene amplification, a Tm value determination, and a polymorphism analysis using the same reaction solution. The aforementioned primer for the β2AR gene can be used as the following primer.
(x) amplifying the sequence to be detected in a reaction solution using a primer for amplifying the sequence to be detected in the β2AR gene, with nucleic acid contained in a sample being used as a template The gene amplification method in the step (x) is not particularly limited and can apply, for example, the method as described above, and a PCR method is preferable.

The probe for analyzing the β2AR gene can be added to a reaction solution for an amplification reaction after step (x) i.e. after the β2AR gene is subjected to an amplification reaction. However, it is preferable that the probe be added to the reaction solution prior to the amplification reaction in step (x) since this allows analysis to be performed easily and quickly. In this case, the reaction solution after an amplification reaction in the step (x) can be used as a reaction solution in the step (a). Such a method makes it possible to perform a melting temperature analysis directly using a reaction solution used for the amplification reaction.

The ratio of the probe to be added to the reaction solution is not particularly limited. For example, each probe is added to be preferably in the range of 10 to 400 nmol and more preferably in the range of 20 to 200 nmol. When a fluorescent dye is used as the label for a probe, an unlabeled probe with a sequence identical to that of the labeled probe may be used in combination with the labeled probe, for example, in order to adjust the fluorescence intensity to be detected, and the unlabeled probe may include phosphate group added to the 3' end thereof. In this case, the molar ratio between the labeled probe and the unlabeled probe is preferably, for example, 1:10 to 10:1. The length of the probe is not particularly limited. It is, for example, 5- to 50-mers and preferably 10- to 50-mers.

In the aforementioned step (b), the measurement of the signal values that indicate the melting states of the hybridization product between the sequence to be detected and the probe for analyzing the β2AR gene may be, for example, a measurement of absorbance at 260 nm as described above using an unlabeled probe but preferably be a measurement of the signal of a labeling substance using the labeled probe. Specifically, it is preferable that a labeled probe labeled with a labeling substance be used as the probe for analyzing the β2AR gene to perform the measurement of the signal of the labeling substance. The labeled probe can be, for example, as described above and the measurement can be performed, for example, as described above.

The sample to which the present invention is to be applied is not particularly limited as long as it contains, for example, nucleic acid to serve as a template however can be, for example, as described above. Further, a ratio of the sample to be added to the reaction solution is, for example, as described above.

Next, with respect to the β2AR gene analysis method of the present invention, a method, in which the β2AR gene is amplified by PCR from the whole blood sample and a polymorphism of the β2AR gene (polymorphism of base 4265 in SEQ ID NO: 1) is determined using a probe for analyzing the β2AR gene of the present invention, is explained as an example. This can be performed in the same manner as the aforementioned obesity gene polymorphism analysis method of the present invention unless otherwise noted, however is not limited thereto.

First, PCR is performed by preparing a PCR reaction solution. Then, the amplification product thus obtained is disassociated and a single-stranded DNA obtained by the dissociation is hybridized with the probe for analyzing the β2AR gene. Thereafter, the reaction solution is heated (a hybridization product between the single-stranded DNA and the probe for analyzing the β2AR gene is heated) and the signal values of the reaction solution are measured. A measurement of the signal values can be determined suitably according to the presence or absence of a label of a probe for analyzing the β2AR gene to be used and types of the labeling substances, in the same manner as described above.

Next, the Tm value is determined by analyzing a change in the signal values measured. In the case where the probe for analyzing the β2AR gene is a fluorescently-labeled probe, for example, the amount of change in the fluorescence intensity per unit time at each temperature (−d fluorescence intensity change/dt or d fluorescence intensity change/dt) is calculated from the fluorescence intensity obtained and the temperature at which the highest absolute value is obtained is determined as the Tm value. For example, in the case of a guanine quenching probe, the temperature at which the lowest value of −d fluorescence intensity increase/dt is obtained, or the temperature at which the highest value of d fluorescence intensity increase/dt is obtained may be determined as the Tm value. On the contrary the amount of decrease in the fluorescence intensity is measured when the labeled probe used is not a quenching probe but a probe that does not exhibit a signal independently but exhibits a signal after hybridization.

From such Tm values, the genotypes in the site to be detected of the β2AR gene are determined. In the Tm analysis, the case of a perfectly complementary hybrid (perfect matching) results in a higher Tm value indicating dissociation than that obtained in the case of a hybrid including a different single base (mismatching). Accordingly, when with respect to the probe, the Tm value obtained in the case of a perfectly complementary hybrid and the Tm value obtained in the case of a hybrid including a different single base are determined beforehand, it can be determined whether the amplification product matches or mismatches with the probe. For example, in the case where the base of the site to be detected located at the sequence to be detected is assumed to be of a mutation type (with, for instance, guanine at base 4265 in SEQ ID NO:

1), when using a probe complementary to the sequence to be detected containing the base (with cytosine at the base "y" in SEQ ID NO: 2), the polymorphism of the amplification product can be judged as a mutation type if the Tm value of the resultant hybrid is equal to the Tm value of a perfectly complementary hybrid. Furthermore, the polymorphism of the amplification product can be judged as a wild-type (with adenine at base 4265 in SEQ ID NO: 1) if the Tm value of the resultant hybrid is equal to the Tm value of the hybrid including a different single base (i.e. a lower value than the Tm value of the perfectly complementary hybrid). Moreover, when only one of the Tm value is detected, it can be determined as homozygote, and when both of the Tm values are detected, it can be determined as heterozygote. Thus, a polymorphism of the β2AR gene can be judged from the Tm value with respect to the probe for analyzing the β2AR gene.

With respect to the β2AR gene analysis method of the present invention, by using the probe of the present invention, the Tm value in the case where the sequence to be detected perfectly matches with the probe and the Tm value in the case where the sequence to be detected mismatches with the probe show difference which can sufficiently be determined. The difference is, for example, at least 4° C., and preferably, at least 6° C.

In the present invention, for example, a change in the signal during hybridization may be measured instead of the method in which the temperature of a reaction solution containing the probes is increased (a hybridization product is heated) and a change in the signal accompanying the temperature rise is measured as described above.

<Polymorphism Analysis Method>

Polymorphism analysis method of the present invention is a polymorphism analysis method analyzing a polymorphism of a site to be detected in the β2AR gene by analyzing the melting temperature, wherein the method includes the β2AR gene analysis method of the present invention. The polymorphism analysis method of the present invention can be performed in the same manner as the aforementioned β2AR gene analysis method of the present invention.

Next, examples of the present invention are described. However, the present invention is not limited by the following examples.

Example 1

Blood was collected from eight subjects using heparin lithium blood collection tubes (Samples 1 to 8). Subsequently, 10 μL of blood thus obtained and 90 μL of distilled water were mixed together. Further, 10 μL of this mixture and 90 μL of distilled water were mixed together. Thereafter, 10 μL of the mixture was added to 40 μL of PCR reaction solution including the following composition, and then PCR was performed using a thermal cycler. Conditions for PCR were as follows. That is, after treating at 95° C. for 60 seconds, one cycle of treatment at 95° C. for 1 second and at 56° C. for 10 seconds was repeated for 50 cycles, and further it was treated at 95° C. for 1 second and at 40° C. for 60 seconds. Subsequently, the PCR reaction solution was heated from 40° C. to 95° C. at a rate of temperature rise of 1° C./3 seconds, and the change in fluorescence intensity over time was measured. The measurement wavelength was 450 to 480 nm (for detection of the fluorescent dye, Pacific Blue), 515 to 555 nm (for detection of the fluorescent dye, BODIPY FL), and 585 to 700 nm (for detection of the fluorescent dye, TAMRA). The time required for 50 cycles of PCR was approximately one hour.

TABLE 7

<PCR reaction solution; unit: μl>

| | |
|---|---|
| Distilled water | 11 |
| 5% NaN$_3$ | 0.4 |
| 20% BSA | 1 |
| 40% Glycerol | 12.5 |
| 10 × Gene Taq buffer* | 5 |
| 2.5 mM dNTPs | 4 |
| 100 mM MgCl$_2$ | 0.5 |
| 5 μM probe for β2AR gene | 1 |
| 5 μM probe 1 for β3AR gene | 0.5 |
| 5 μM probe 2 for β3AR gene | 0.8 |
| 5 μM probe for UCP1 gene | 0.8 |
| 100 μM β2AR gene F1 primer | 0.5 |
| 100 μM β2AR gene R1 primer mix | 0.25 |
| 100 μM β3AR gene F2 primer | 0.25 |
| 100 μM β3AR gene R2 primer | 0.5 |
| 100 μM UCP1 gene F3 primer | 0.25 |
| 100 μM UCP1 gene R3 primer mix | 0.5 |
| 5 U/μl Gene Taq FP* | 0.25 |
| Total | 40 μL |

*Trade name, Gene Taq FP: manufactured by Nippon Gene Co., Ltd.

<Probes>

```
Probe for β2AR gene
                                (SEQ ID NO: 72)
5'-cgcatggcttcCattgggtgcca-(Pacific Blue)-3'

Probe 1 for β3AR gene
                                (SEQ ID NO: 83)
5'-cgtggccatcgccCggactc-(BODIPY FL)-3'

Probe 2 for β3AR gene
                                (SEQ ID NO: 83)
5'-cgtggccatcgccCggactc-P-3'

Probe for UCP1 gene
                                (SEQ ID NO: 95)
5'-(TAMRA)-cacagtttgatcGagtgcatttg-3'
```

<Primer Set>

```
β2AR gene F1 primer
                                (SEQ ID NO: 9)
5'-cccgggaacggcagcgcctt-3'

β2AR gene R1 primer mix
                                (SEQ ID NO: 18)
5'-cccacacctcgtccctttSctgcgt-3'
S is c or g and the both primers are mixed at 1:1
(molar ratio)

β3AR gene F2 primer
                                (SEQ ID NO: 26)
5'-ccaccgtgggaggcaacc-3'

β3AR gene R2 primer
                                (SEQ ID NO: 31)
5'-ctgcggccagcgaagtc-3'

UCP1 gene F3 primer
                                (SEQ ID NO: 44)
5'-ggaagacattttgtgcagcgatttctgattgacc-3'

UCP1 gene R3 primer mix
                                (SEQ ID NO: 63)
5'-cKtagcaaaggagtggcagcaagttctg-3'
K is g or t and the both primers are mixed at 1:1
(molar ratio)
```

The Tm value of a hybrid that matches with the probe for the β2AR gene is 70.0° C. and that of a hybrid that mismatches therewith is 62.0° C., the Tm value of a hybrid that matches with the probe for the β3AR gene is 73.0° C. and that of a hybrid that mismatches therewith is 66.0° C., and the Tm value of a hybrid that matches with the probe for the UCP1 gene is 65.0° C. and that of a hybrid that mismatches therewith is 60.0° C.

Figure 2:
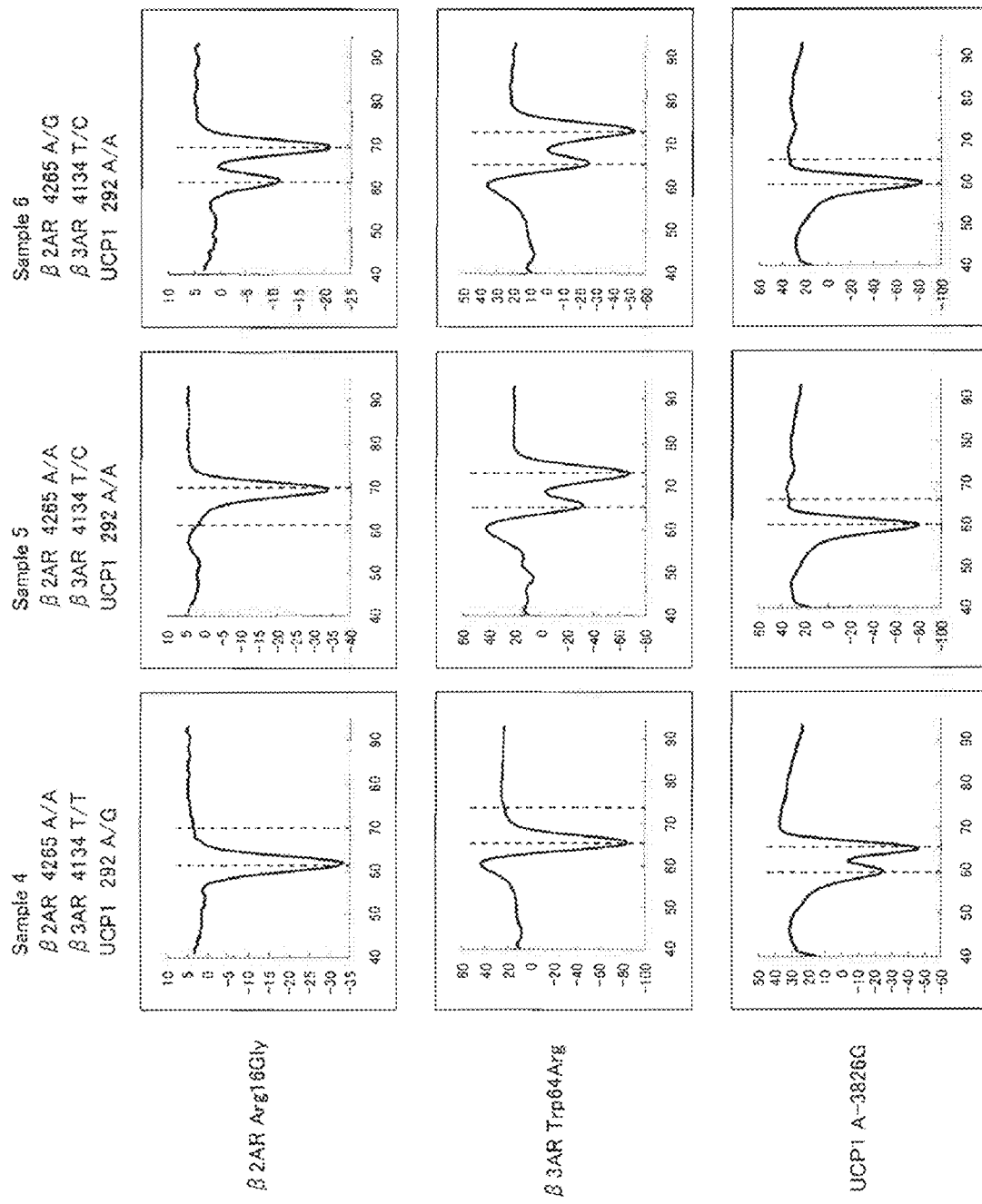
FIG. 2 shows graphs indicating the results of Tm analysis in Example 1 of the present invention described above.
Figure 3:
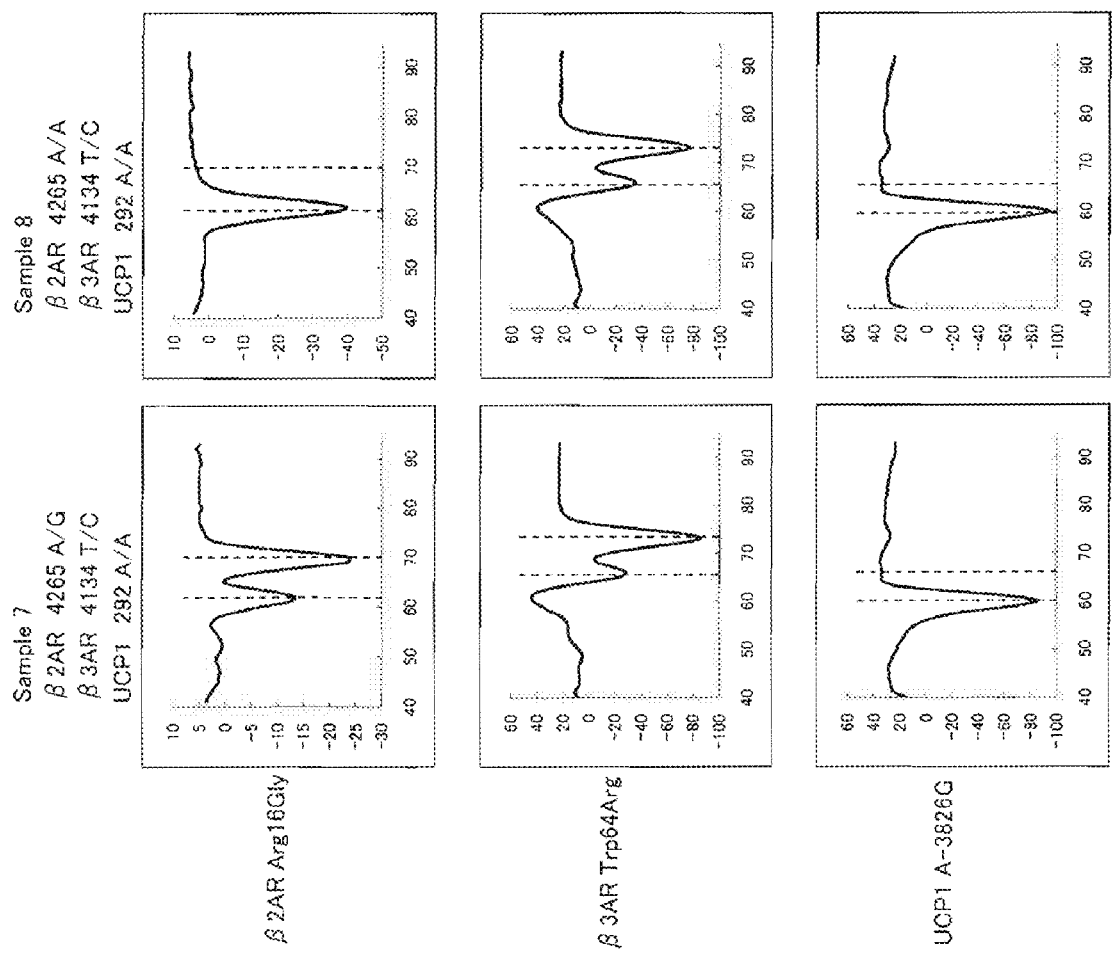
FIG. 3 shows graphs indicating the results of Tm analysis in Example 1 of the present invention described above.

Results of samples 1 to 8 are indicated in FIGS. 1 to 3. These figures show graphs of Tm analysis that indicate the changes in fluorescence intensity accompanying temperature rise. The differential value of the vertical axis indicates "−d fluorescence intensity increase/dt", while the horizontal axis indicates temperature (the same applies below). As shown in these figures, respective polymorphisms of the β2AR gene, the β3AR gene, and the UCP1 gene in each sample were determined from the peaks of the signals. In order to support the results of these examples, with respect to eight subjects, respective polymorphisms of the β2AR gene, the β3AR gene, and the UCP1 gene were confirmed by the RFLP method. As a result, the same results as those obtained in the example were obtained. Accordingly, the use of a primer set of the present invention made it possible to amplify the β2AR gene, the β3AR gene, and the UCP1 gene simultaneously in the same reaction solution using a whole blood sample that had not been pretreated and to analyze respective polymorphisms of the aforementioned genes using the same reaction solution.

Example 2

Blood was collected from three subjects using EDTA blood collection tubes (Samples 1 to 3). Subsequently, 10 µL of blood thus obtained and 70 µL of diluent A described below were mixed together Further, 10 µL of this mixture and 70 µL of diluent B described below were mixed together. Subsequently, 10 µL of the mixture thus obtained was heat-treated at 95° C. for five minutes. Thereafter, this was added to 46 µL of PCR reaction solution having the following composition, and then PCR was performed using a thermal cycler. Conditions for PCR were as follows. That is, after treating at 95° C. for 60 seconds, one cycle of treatment at 95° C. for 1 second and at 64° C. for 15 seconds was repeated for 50 cycles, and further it was treated at 95° C. for 1 second and at 40° C. for 60 seconds. Subsequently, the PCR reaction solution was heated from 40° C. to 75° C. at a rate of temperature rise of 1° C./3 seconds, and the change in fluorescence intensity over time was measured. The measurement wavelength was 450 to 480 nm (for detection of the fluorescent dye, Pacific Blue), 515 to 555 nm (for detection of the fluorescent dye, BODIPY FL), and 585 to 700 nm (for detection of the fluorescent dye, TAMRA).
<Diluent A>
10 mM Tris-HCl (pH 8), 0.1 mM EDTA, 0.05% NaN$_3$, 0.3% SDS
<Diluent B>
10 mM Tris-HCl (pH 8), 0.1 mM EDTA, 0.05% NaN$_3$

TABLE 8

| <PCR reaction solution; unit: µl> | |
|---|---|
| Distilled water | 12.25 |
| 5% NaN$_3$ | 0.5 |
| 20% BSA | 0.5 |
| 40% Glycerol | 15 |
| 10 × Gene Taq buffer* | 5 |
| 2.5 mM dNTPs | 4 |
| 100 mM MgCl$_2$ | 0.25 |
| 5 µM probe for β2AR gene | 2 |
| 5 µM probe 1 for β3AR gene | 1 |
| 5 µM probe 2 for β3AR gene | 1 |
| 5 µM probe for UCP1 gene | 2 |
| 100 µM β2AR gene F1 primer | 0.25 |

TABLE 8-continued

| <PCR reaction solution; unit: µl> | |
|---|---|
| 100 µM β2AR gene R1 primer | 0.5 |
| 100 µM β3AR gene F2 primer | 0.5 |
| 100 µM β3AR gene R2 primer | 0.25 |
| 100 µM UCP1 gene F3 primer | 0.25 |
| 100 µM UCP1 gene R3 primer mix | 0.5 |
| 5 U/µl Gene Taq FP* | 0.25 |
| Total | 46 µL |

*Trade name, Gene Taq FP: manufactured by Nippon Gene Co., Ltd.

<Probes>

```
Probe for β2AR gene
                                    (SEQ ID NO: 114)
5'-(Pacific Blue)-cccaatGgaagccatgc-P-3'

Probe 1 for β3AR gene
                                    (SEQ ID NO: 120)
5'-(BODIPY FL)-ctcggagtccGggcP-3'

Probe 2 for β3AR gene
                                    (SEQ ID NO: 120)
5'-(BODIPY FL)-ctcggagtccAgg-P-3'

Probe for UCP1 gene
                                    (SEQ ID NO: 139)
5'-(TAMRA)-cacagtttgatcGagtg-P-3'
```

<Primer Set>

```
β2AR gene F1 primer
                                    (SEQ ID NO: 109)
5'-cgggaacggcagcgccttct-3'

β2AR gene R1 primer
                                    (SEQ ID NO: 134)
5'-ccaccacccacacctcgtccct-3'

β3AR gene F2 primer
                                    (SEQ ID NO: 24)
5'-gccaccgtgggaggcaacc-3'

β3AR gene R2 primer
                                    (SEQ ID NO: 28)
5'-ggctgcggccagcgaagtc-3'

UCP1 gene F3 primer
                                    (SEQ ID NO: 43)
5'-ggaagacattttgtgcagcgatttctgattgacc-3'

UCP1 gene R3 primer mix
                                    (SEQ ID NO: 63)
5'-cKtagcaaaggagtggcagcaagttctg-3'
K is g or t and the both primers are mixed at 1:1
(molar ratio)
```

The Tm value of a hybrid that matches with the probe for the β2AR gene is 58° C. and that of a hybrid that mismatches therewith is 51° C., the Tm value of a hybrid that matches with the probe for the β3AR gene is 58° C. and that of a hybrid that mismatches therewith is 51° C., and the Tm value of a hybrid that matches with the probe for the UCP1 gene is 56° C. and that of a hybrid that mismatches therewith is 49° C.

Figure 4:
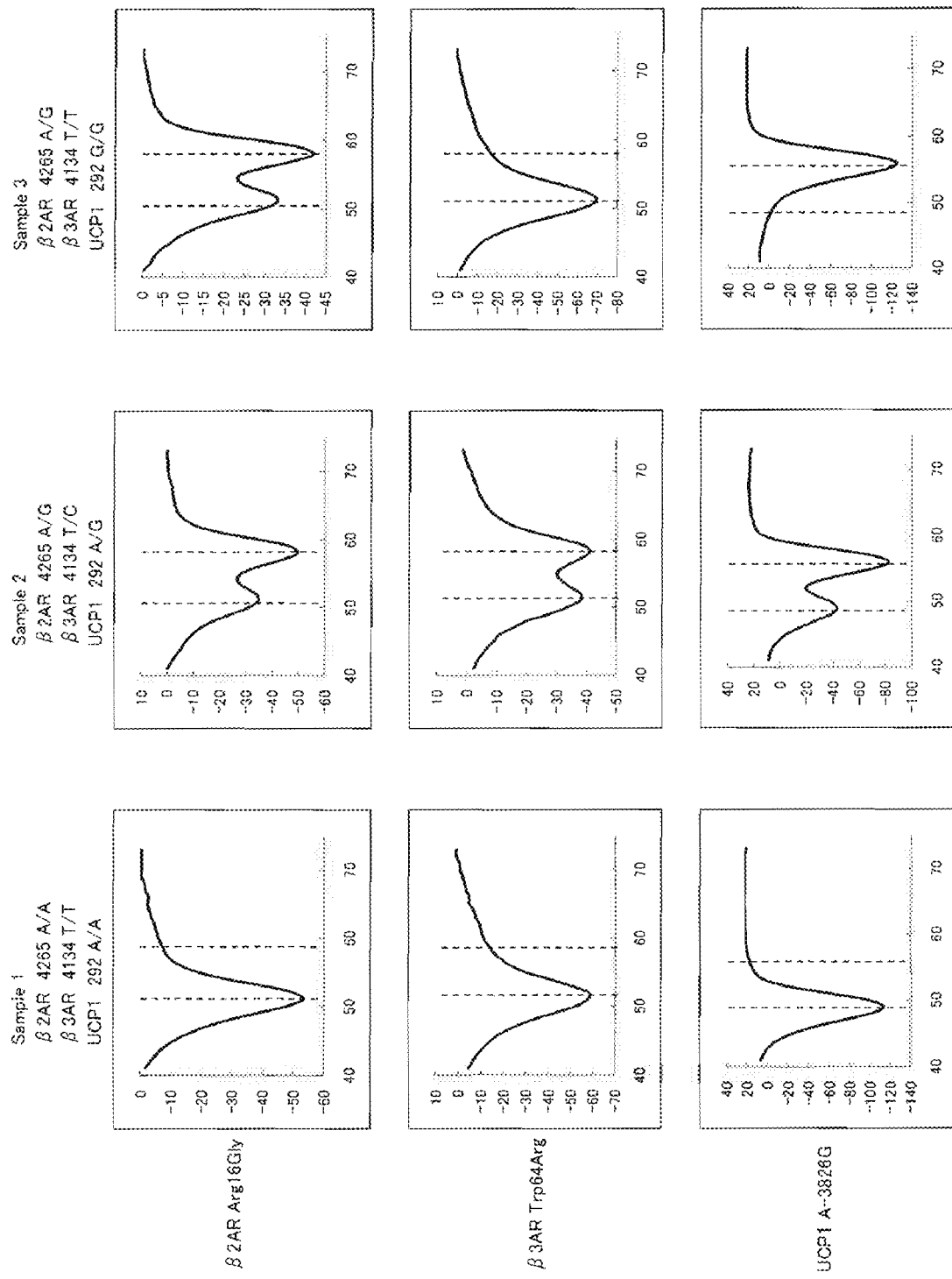
FIG. 4 shows graphs indicating the results of Tm analysis in Example 2 of the present invention.

Results of Samples 1 to 3 are indicated in FIG. 4. FIG. 4 shows graphs of Tm analysis that indicate the changes in fluorescence intensity accompanying temperature rise. The differential value of the vertical axis indicates "−d fluorescence intensity increase/dt", while the horizontal axis indicates temperature. As shown in these graphs, respective polymorphisms of the β2AR gene, the β3AR gene, and the UCP1 gene in each sample were determined from the peaks of the signals. In order to support the results of these examples, with respect to three subjects respective polymorphisms of the β2AR gene, the β3AR gene, and the UCP1 gene were confirmed by the RFLP method. As a result, the same results as those obtained in the example were obtained. Accordingly, the use of a primer set of the present invention made it possible to amplify the β2AR gene, the β3AR gene, and the UCP1 gene simultaneously in the same reaction solution using a whole blood sample that had not been pretreated and to analyze respective polymorphisms of the aforementioned genes using the same reaction solution.

Example 3

Respective types of probes for the β2AR gene were produced and the Tm analysis was performed. First, the probe indicated in Table 9 and oligonucleotide (complementary strand DNA) indicated in Table 10 complementary to the respective probes were synthesized. In the sequences of the respective probes in Table 9, capitalized base indicates base corresponding to base 4265 in SEQ ID NO: 1. These probes are designed for detecting the base (G, A) at 4265 in a sense strand or the base (C or T) in an antisense strand complementary thereto. The respective oligonucleotides indicated in Table 10 are partial sequences of sense strands of the β2AR gene or antisense strands of the β2AR gene, and are the sequences including base 4265 in SEQ ID NO: 1 or the base complementary thereto. Then, a reaction solution was prepared using these probes and complementary strand DNA so that the reaction solution includes the composition indicated in Table 11. In the case where the strand to be detected of the probe was a sense strand, 1A (4265A) and 1B (4265G) were used as the complementary strand DNA, and the reaction solution to which 1A and 1B were respectively added was prepared. In contrast, in the case where the strand to be detected of the probe is an antisense strand, 2A (4265A) and 2B (4265G) were used as the complementary strand DNA, and the reaction solution to which 2A and 2B were respectively added was prepared. These reaction solutions were subjected to a thermal cycler (trade name, Smart Cycler manufactured by Cepheid). The reaction solution was heated from 45° C. to 95° C. at a rate of temperature rise of 1° C./3 seconds, and the change in fluorescence intensity over time was measured. The measurement wavelength was 565 to 605 nm (for detection of TAMRA, ch3).

TABLE 9

| Probe | Sequence | Strand to be Detected | mer | GC content | SEQ ID NO. |
|---|---|---|---|---|---|
| Comparative Example 3-1 | 5'-cacccaatGgaagcc-(TAMRA)-3' | antisense | 15 | 60.0 | 140 |
| Comparative Example 3-2 | 5'-(TAMRA)-ccaatGgaagccatgc-P-3' | antisense | 16 | 56.3 | 141 |
| Comparative Example 3-3 | 5'-catggcttcCattgggtgcc-(TAMRA)-3' | sense | 20 | 60.0 | 142 |
| Comparative Example 3-4 | 5'-(TAMRA)-catggcttcCattgggtg-P-3' | sense | 18 | 55.6 | 143 |
| Comparative Example 3-5 | 5'-ggcttcCattgggtgcc-(TAMRA)-3' | sense | 17 | 64.7 | 144 |
| Comparative Example 3-6 | 5'-ggcacccaatAgaagcc-(TAMRA)-3' | antisense | 17 | 58.8 | 145 |
| Comparative Example 3-7 | 5'-(TAMRA)-ccggcgcatggcttcCattg-P-3' | sense | 20 | 65.0 | 146 |
| Comparative Example 3-8 | 5'-tAgaagccatgcgcc-(TAMRA)-3' | antisense | 15 | 60.0 | 147 |
| Comparative Example 3-9 | 5'-(TAMRA)-ccaatAgaagccatgcg-P-3' | antisense | 17 | 52.9 | 148 |
| Comparative Example 3-10 | 5'-(BODIPY FL)-ccaatGgaagccatg-P-3' | antisense | 15 | 53.3 | 149 |
| Comparative Example 3-11 | 5'-tGgaagccatgcgcc-(TAMRA)-3' | antisense | 15 | 66.7 | 150 |
| Comparative Example 3-12 | 5'-(TAMRA)-caatGgaagccatgc-P-3' | antisense | 15 | 53.3 | 151 |
| Comparative Example 3-13 | 5'-(TAMRA)-cttcCattgggtgccag-P-3' | sense | 17 | 58.8 | 152 |
| Comparative Example 3-14 | 5'-(TAMRA)-cCattgggtgccagca-P-3' | sense | 16 | 62.5 | 153 |
| Comparative Example 3-15 | 5'-(TAMRA)-cttcCattgggtgccagcaaga-P-3' | sense | 22 | 54.5 | 154 |
| Comparative Example 3-16 | 5'-gctggcacccaatGgaagcc-(TAMRA)-3' | antisense | 20 | 65.0 | 155 |

TABLE 9-continued

| Probe | Sequence | Strand to be Detected | mer | GC content | SEQ ID NO. |
|---|---|---|---|---|---|
| Comparative Example 3-17 | 5'-(TAMRA)-ccaatGgaagccatgcgc-P-3' | antisense | 18 | 61.1 | 156 |
| Comparative Example 3-18 | 5'-(TAMRA)-ccaatGgaagccatgcgccg-P-3' | antisense | 20 | 65.0 | 157 |
| Comparative Example 3-19 | 5'-ccaatGgaagccatgcgcc-(TAMRA)-3' | antisense | 19 | 63.2 | 158 |
| Comparative Example 3-20 | 5'-ggcttcCattgggtgcca-(TAMRA)-3' | sense | 18 | 61.1 | 159 |
| Comparative Example 3-21 | 5'-(TAMRA)-catggcttcCattgggtgccag-P-3' | sense | 22 | 59.1 | 160 |
| Example 3-1 | 5'-cgcatggcttcCattgggtgcca-(TAMRA)-3' | sense | 23 | 60.9 | 72 |

TABLE 10

| complementary strand DNA | Sequence | SEQ ID NO. |
|---|---|---|
| 1A: sense strand (4265A) | cgccttcttgctggcacccaatAgaagccatgcgccggac | 161 |
| 1B: sense strand (4265G) | cgccttcttgctggcacccaatGgaagccatgcgccggac | 162 |
| 2A: antisense strand (4265T) | gtccggcgcatggcttcTattgggtgccagcaagaaggcg | 163 |
| 2B: antisense strand (4265C) | gtccggcgcatggcttcCattgggtgccagcaagaaggcg | 164 |

TABLE 11

| | |
|---|---|
| Distilled water | 17 |
| 10 × Gene Taq buffer* | 5 |
| 5 μM probe | 1 |
| 5 μM complementary strand DNA | 2 |
| Total | 25 μL |

*Trade name, Gene Taq FP: manufactured by Nippon Gene Co., Ltd.

Figure 5:
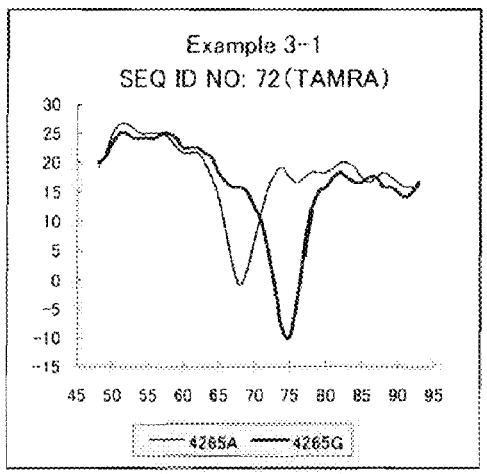
FIG. 5 shows a graph indicating the results of Tm analysis in Example 3 of the present invention.
Figure 6:
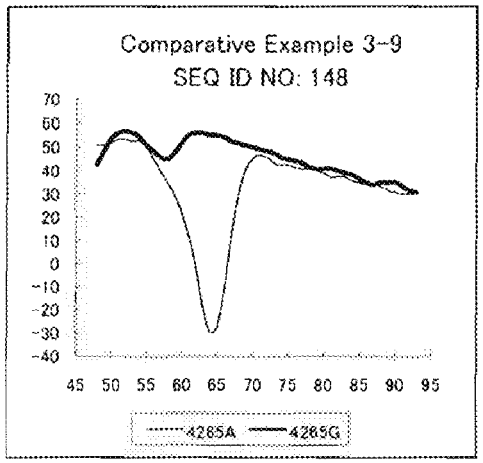
FIG. 6 shows graphs indicating the results of Tm analysis in Comparative Examples.
Figure 6:
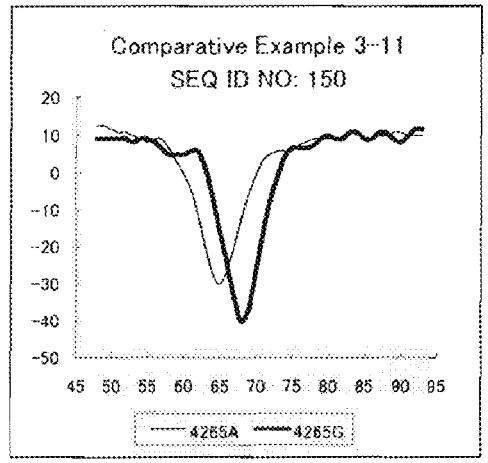

Results using a probe of Example 3-1 and probes of Comparative Examples 3-9 and 3-11 are respectively indicated in FIGS. 5 and 6. These figures show graphs (melting curves) of Tm analysis that indicate the changes in fluorescence intensity accompanying temperature rise. The differential value of the vertical axis indicates "−d fluorescence intensity increase/dt", while the horizontal axis indicates temperature (the same applies below). A melting curve (a thin line) of a system, in which the complementary strand DNA (1A) was added to a reaction solution, and a melting curve (a thick line) of a system, in which the complementary strand DNA (1B) was added to a reaction solution, are indicated together in FIG. 5. A melting curve (a thin line) of a system, in which the complementary strand DNA (2A) was added to a reaction solution, and a melting curve (a thick line) of a system, in which the complementary strand DNA (2B) was added to a reaction solution, are indicated together in FIG. 6.

As shown in FIG. 6, in the case where the probe of Comparative Example 3-9 was used, the signal peak of 4265G was not detected. Further, in the case where the probe of Comparative Example 3-11 was used, the difference between the Tm value (68° C.) of the peak that indicates the perfect matching between the probe and the complementary strand DNA (2B), and the Tm value (65° C.) of the peak that indicates the mismatching between the probe and the complementary strand DNA (2A) was small (3° C.). Accordingly, from the melting curves using the probes of those Comparative Examples, it was difficult to judge whether the perfect matching or the mismatching was indicated, with an excellent reliability. Further, with respect to other Comparative Examples, the melting curves similar to that of Comparative Examples 3-9 and 3-11 shown in FIG. 6 were indicated. In contrast, in the case where the probe of Example 3-1 was used, as shown in FIG. 5, both of the signal peak that indicates the perfect matching between the probe and the complementary strand DNA (1B) and the signal peak that indicates the mismatching between the probe and the complementary strand DNA (1A) could sufficiently be confirmed. Further, the difference between the Tm value (75° C.) of the peak that indicates the aforementioned perfect matching and the Tm value (68° C.) of the peak that indicates the aforementioned mismatching was about 7° C. This difference was sufficient for distinguishing the perfect matching and the mismatching. Therefore, the probe of Example makes it possible to sufficiently judge whether the perfect matching or the mismatching is indicated.

Example 4

Human purified genome that indicates homozygote including 4265A/4265A at base 4265 in SEQ ID NO: 1, and human purified genome that indicates homozygote including 4265G/4265G at base 4265 in SEQ ID NO: 1 were prepared. 1 μL of these purified genomes were respectively added to 24 μL of PCR reaction solution including the following composition. These PCR reaction solutions were subjected to a thermal cycler (trade name, Smart Cycler manufactured by Cepheid) and PCR was performed. Conditions for PCR were as follows. That is, after treating at 95° C. for 60 seconds, one cycle of treatment at 95° C. for 1 second and at 62° C. for 30 seconds was repeated for 50 cycles. Subsequently, the PCR reaction solution was heated from 45° C. to 95° C. at a rate of temperature rise of 1° C./second, and the change in fluorescence intensity over time was measured. The measurement wavelength was 505 to 537 nm (for detection of the fluorescent dye, FAM, 1ch).

TABLE 12

<PCR reaction solution; unit: μl>

| | |
|---|---|
| Distilled water | 6.625 |
| 40% Glycerol | 12.5 |
| 10 × Gene Taq buffer* | 2.5 |
| 10 mM dNTPs | 0.5 |
| 100 mM MgCl₂ | 0.375 |
| 5 μM probe for β2AR gene | 1 |
| 100 μM β2AR gene forward primer | 0.25 |
| 100 μM β2AR gene reverse primer | 0.125 |
| 5 U/μl Gene Taq FP* | 0.125 |
| Total | 24 μL |

*Trade name, Gene Taq FP: manufactured by Nippon Gene Co., Ltd.

<Probe>

```
Probe for analyzing β2AR gene
                              (SEQ ID NO: 72)
5'-cgcatggcttcCattgggtgcca-(BODIPY FL)-3'
```

<Primer Set>

```
β2AR gene forward primer
5'-gggaacggcagcgccttcttgct-3'    (SEQ ID NO: 165)

β2AR gene reverse primer
5'-tggtgaccgtctgcagacgctcgaac-3' (SEQ ID NO: 166)
```

A region amplified by PCR using the aforementioned primer set is a DNA strand of about 200 bases including base 4265 in SEQ ID NO 1. DNA strand having G at base 41265 (C in antisense strand) was amplified from genome that indicates 4265G/4265G, and DNA having A at base 4265 (T in antisense) was amplified from genome that indicates 4265A/4265A.

The Tm value of a hybrid that matches with the probe for analyzing the β2AR gene indicated in the SEQ ID NO: 72 is 69° C. and that of a hybrid that mismatches therewith is 62° C.

Figure 7:
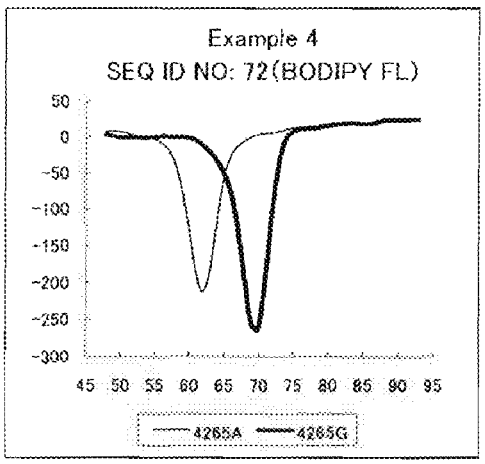
FIG. 7 shows a graph indicating the results of Tm analysis in Example 4 of the present invention.

Results thereof are indicated in FIG. 7. FIG. 7 shows a graph (a melting curve) of Tm analysis that indicates the change in fluorescence intensity accompanying temperature rise. The differential value of the vertical axis indicates "−d fluorescence intensity increase/dt", while the horizontal axis indicates temperature (the same applies below). In FIG. 7, a melting curve (a thin line) of a system, in which human purified genome that indicates 4265A/4265A homozygote was added, and a melting curve (a thick line) of a system, in which human purified genome that indicates 4265G/4265G homozygote was added are indicated together.

Tm analysis was performed by amplifying DNA in the β2AR gene of human purified genome under the coexistence of the probe of Example 4. As a result, as shown in FIG. 7, the base at 4265 could be distinguished. Specifically the difference between the Tm value (69° C.) of the peak that indicates the perfect matching between the probe and the amplification product derived from 4265G/4265G homozygote, and the Tm value (62° C.) of the peak that indicates the mismatching between the probe and the amplification product derived from 4265)A/4265A homozygote was about 7° C. This difference was sufficient for distinguishing the perfect matching and the mismatching. Therefore, the probe of Example makes it possible to sufficiently analyze a polymorphism at base 4265 in the β2AR gene.

INDUSTRIAL APPLICABILITY

As described above, the primer set of the present invention makes it possible to specifically and efficiently amplify a region including a site where a particular polymorphism in the obesity gene (the β2AR gene, the β3AR gene, or the UCP1 gene) is generated. This allows time and cost to be reduced, which is different from the conventional methods as described above. Furthermore, since the region including a site to be detected of a polymorphism is amplified specifically, for example, the use of a probe complementary to a sequence to be detected including the site to be detected makes it possible to perform Tm analysis directly using the aforementioned reaction solution to type the polymorphism. Moreover, since amplification and typing can be carried out using one reaction solution, the operation can be automated. The use of the primer set of the present invention allows a pretreatment to be omitted even in the case of, for example, a contaminated sample (for instance, whole blood or oral mucosa), and therefore the amplification reaction can be carried out quicker and more easily. Furthermore, when the primer set of the present invention is used, the amplification reaction can be carried out with higher amplification efficiency as compared to conventional cases and thus the reaction time can also be shortened. According to the primer set of the present invention, the reagent including the same, as well as the method of manufacturing an amplification product using them, since the polymorphism in the obesity gene can be analyzed quickly and simply it can be said that they are considerably effective in the field of medicine.

The invention claimed is:

1. A probe having a melting temperature sufficient to detect a single nucleotide polymorphism in the β2AR gene (SEQ ID NO: 1) at base 4265, wherein the probe is composed of the following oligonucleotide (P1):
   (P1) at least one oligonucleotide selected from the following (1-1) and (1-2)
   (1-1), at least one oligonucleotide complementary to a region extending from thymine (T) at base 4254 to be considered as the first base to any one of the 21st to 26th bases in the direction toward the 3' end in SEQ ID NO: 1, with adenine (A) complementary to the thymine being the 3' end, and
   (1-2) at least one oligonucleotide having a sequence identical to that of a region extending from cytosine (C) at base 4259 to be considered as the first base to any one of the 15th to 19th bases in the direction toward the 3' end in SEQ ID NO: 1, with the cytosine being the 5' end.

2. The probe according to claim 1, wherein the probe is composed of the following oligonucleotide (P1'):
   (P1') at least one oligonucleotide selected from an oligonucleotide consisting of the base sequence of SEQ ID NO: 72, or an oligonucleotide consisting of the base sequence of SEQ ID NO: 114.

3. The probe according to claim 1, wherein the probe is a labeled probe labeled with a labeling substance.

4. The probe according to claim 3, wherein the labeling substance is a fluorescent dye.

5. The probe according to claim 4, wherein the labeled probe is a probe that exhibits fluorescence independently and allows fluorescence to be quenched after hybridization.

6. The probe according to claim 3, wherein the probe is a labeled probe labeled with the labeling substance at the 3' end of the oligonucleotide (1-1).

7. The probe according to claim 3, wherein the probe is a labeled probe labeled with the labeling substance at the 5' end of the oligonucleotide (1-2).

8. A diagnostic reagent composition comprising the probe according to claim 1.

9. A diagnostic reagent composition according to claim 8, further comprising at least one primer which hybridizes to a sequence of the β2AR flanking the base at 4265 of the β2AR (SEQ ID NO: 1).

10. An obesity gene analysis method, wherein the obesity gene is the β2AR gene, and wherein the method comprises the following processes (a) to (c):

(a) preparing a reaction solution that contains a β2AR gene sequence and a probe according to claim 1,
(b) measuring a signal value that indicates a melting state of a hybridization product between the sequence to be detected and the probe while changing the temperature of the reaction solution, and
(c) determining a melting temperature of the hybridization product from a change in the signal value accompanying a change in the temperature.

11. The method according to claim 10, wherein the probe for analyzing the obesity gene is a labeled probe labeled with a fluorescent dye, and wherein, in the process (b), fluorescence intensity of the fluorescent dye is measured as the signal value.

12. The method according to claim 11, wherein the labeled probe is a probe that exhibits fluorescence independently and allows fluorescence to be quenched after hybridization, and wherein, in the process (b), temperature of the reaction solution is increased and a decrease in fluorescence intensity accompanying the temperature rise is measured.

13. The method according to claim 10, further comprising amplifying the sequence to be detected in a reaction solution using a primer for amplifying the sequence to be detected in the β2AR gene, with nucleic acid contained in a sample being used as a template.

14. The method according to claim 13, wherein the probe for analyzing the obesity gene is added to the reaction solution prior to an amplification reaction and the reaction solution after the amplification reaction is used as a reaction solution in the process (a).

15. The method according to claim 13, wherein the sample is a biological sample.

16. The method according to claim 15, wherein the biological sample is whole blood.

17. The method according to claim 16, wherein a ratio of the whole blood to be added to the reaction solution is 0.1 to 0.5 vol %.

18. The probe according to claim 1, wherein the probe consists of the oligonucleotide sequence of SEQ ID NO: 72.

19. The probe according to claim 1, wherein the probe consists of the oligonucleotide sequence of SEQ ID NO: 114.

20. The method according to claim 10, wherein the probe consists of the oligonucleotide sequence of SEQ ID NO: 72.

21. The method according to claim 10, wherein the probe consists of the oligonucleotide sequence of SEQ ID NO: 114.

* * * * *